United States Patent

Esaki et al.

[11] Patent Number: 6,127,544
[45] Date of Patent: Oct. 3, 2000

[54] INDOLIN-2-ONE DERIVATIVES

[75] Inventors: Toru Esaki; Takashi Emura; Eiichi Hoshino, all of Shizuoka, Japan

[73] Assignee: Chugai Seiyaku Kabushiki Kaisha, Tokyo, Japan

[21] Appl. No.: 09/182,491

[22] Filed: Oct. 30, 1998

Related U.S. Application Data

[62] Division of application No. 08/963,547, Nov. 3, 1997, Pat. No. 5,932,511, which is a continuation of application No. 08/448,579, filed as application No. PCT/JP94/00235, Feb. 17, 1994, abandoned.

[30] Foreign Application Priority Data

Feb. 17, 1993 [JP] Japan ..................................... 5-67297
May 31, 1993 [JP] Japan ..................................... 5-167262

[51] Int. Cl.$^7$ .............................................. C07D 401/12
[52] U.S. Cl. ...................................................... 546/277.7
[58] Field of Search .......................................... 546/277.7

[56] References Cited

U.S. PATENT DOCUMENTS

| | | |
|---|---|---|
| 4,760,083 | 7/1988 | Myers et al. . |
| 4,876,259 | 10/1989 | Myers et al. . |

FOREIGN PATENT DOCUMENTS

| | | |
|---|---|---|
| 0336356A3 | 10/1989 | European Pat. Off. . |
| 62-228072A | 6/1987 | Japan . |
| 62-234080A | 10/1987 | Japan . |
| 62-270576A | 11/1987 | Japan . |
| 62-156771A | 6/1988 | Japan . |
| 63-238069A | 10/1988 | Japan . |
| 51045A | 2/1993 | Japan . |
| 68293B2 | 2/1994 | Japan . |
| WO 92/04038A1 | 3/1992 | WIPO . |
| WO 92/07830A2 | 5/1992 | WIPO . |

OTHER PUBLICATIONS

Skiles et al., *Tetrahedron Letters*, Vol. 31, No. 50, pp. 7277–7280 (1990).

Otomasu et al., *Chem. Pharm. Bull.*, vol. 23, No. 7, pp. 1431–1435 (1975).

Joshi et al., *Heterocycles*, vol. 31, No. 3, pp. 473–477 (1990).

Hino et al., *Chem. Pharm. Bull*, vol. 8, pp. 839–842 (1960).

*Primary Examiner*—Patricia L. Morris
*Attorney, Agent, or Firm*—Birch, Stewart, Kolasch & Birch, LLP.

[57] ABSTRACT

A compound represented by formula (I):

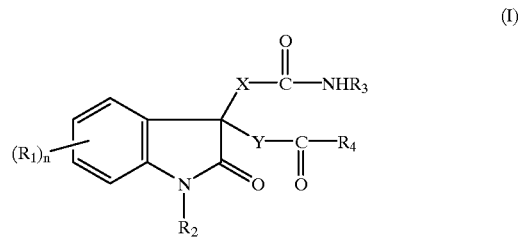

wherein $R_1$ represents a halogen atom, a lower alkyl group, a lower alkoxy group, a hydroxyl group, a nitro group, a trifluoromethyl group, a lower alkylthio group, an acyl group, a carboxyl group, a mercapto group or an amino group; $R_2$ represents a hydrogen atom, a lower alkyl group, a lower alkenyl group, a lower alkynyl group, an alkoxy group, an acyl group, an aryl group or a heterocyclic group; $R_3$ represents a lower alkyl group, a cycloalkyl group, an aryl group, or a heterocyclic group; $R_4$ represents a hydrogen atom, a lower alkyl group, an aryl group, a heterocyclic group, —$OR_5$, —$SR_5$ or —$NR_6R_7$ (wherein $R_5$, $R_6$, and $R_7$ each represent a lower alkyl group, etc.); X and Y each represent —$CH_2$—, —NH— or —O—; and n represents an integer of from 0 to 4, and an intermediate for synthesis thereof are disclosed. The compound of the present invention exhibits selective antagonism against gastrin receptors without causing side effects attributed to CCK-A receptor antagonism and is useful for the treatment and prevention of peptic ulcers, gastritis, reflux esophagitis, and Zollinger-Ellison syndrome, and for the treatment of neoplasm originating in the gastrointestinal system.

1 Claim, No Drawings

INDOLIN-2-ONE DERIVATIVES

This application is a divisional application of application Ser. No. 08/963,547, filed on Nov. 3, 1997, now U.S. Pat. No. 5,932,511; which is a continuation application of application Ser. No. 08/448,579, filed on Jun. 6, 1995, now abandoned; which is the §371 national application of PCT International Application No. PCT/JP94/00235, filed on Feb. 17, 1994. The entire contents of each of the above-identified applications are hereby incorporated by reference.

FIELD OF THE INVENTION

This invention relates to an indolin-2-one derivative which exhibits selective antagonism against gastrin receptors without causing side effects attributed to CCK-A receptor antagonism and is useful for the treatment and prevention of diseases of digestive organs, such as peptic ulcers, gastritis, reflux esophagitis, and Zollinger-Ellison syndrome, and for the treatment of tumours originating in the gastrointestinal system. The compounds also exhibit selective antagonism against CCK-B receptors and are useful for the treatment of CCK-related disorders in the appetite control system, enhancement and prolongation of analgesia through opiate or non-opiate, induction of anesthesia or analgesia, and the treatment and prevention of symptoms of psychotic disorders including anxiety and panic disorder.

BACKGROUND OF THE INVENTION

Gastrin is a typical gastrointestinal hormone, like CCK, secretin, etc. It is known that gastrin accelerates secretion of gastric acid and pepsin and also accelerates growth of gastric mucous cells and especially histamine secretory cells. While gastric acid secretion is stimulated by histamine, acetylcholine, and gastrin, gastrin is the most powerful of these internal substances. Currently known drugs for controlling gastric acid secretion include muscarinic receptor antagonists such as Pirenzepine, histamine $H_2$ receptor antagonists such as Cimetidine, and $H^+$—$K^+$ ATPase inhibitors such as Omeprazole. However, it has been reported that these drugs induce hypergastrinemia during maintained administration due to the potent inhibitory activity on gastric acid secretion, and the high gastrin level induces an increase of histamine content in the gastric mucosa. The reports also reveal that discontinuation of administration of these drugs is followed by an increase of acid secretion, called rebound, and a high rate of relapses.

The study of gastrin has recently been progressed, and participation of gastrin in various diseases has been elucidated. As a result, it has been suggested that a selective antagonist to gastrin receptors would be useful for the treatment and prevention of diseases induced by disorders of physiological functions related to gastrin, i.e., diseases of digestive organs, particularly peptic ulcers, gastritis, reflux esophagitis, and Zollinger-Ellison syndrome; prevention of a relapse following treatment with an $H_2$ receptor antagonist or an $H^+$—$K^+$ ATPase inhibitor; or the treatment and prevention of tumours originating in the gastrointestinal system.

Recently, several gastrin receptor antagonists have been reported. For example, amino acid (glutamic acid) derivatives such as Proglumide and benzodiazepin derivatives such as L-365,260 (Japanese Patent Application Laid-Open No. 238069/88) are known. Proglumide exhibits very weak binding activity to gastrin receptors. L-365,260, while having high binding activity to gastrin receptors, do not exert powerful inhibitory activity on gastric acid secretion when administered in vivo.

On the other hand, CCK is widely distributed through the gastrointestinal system and the central nervous system. It is known that CCK exhibits its activities at the peripheries chiefly via CCK-A receptors accelerating pancreatic secretion, gastrointestinal motility and contractions of the gall bladder, inhibition of gastric emptying, and acceleration of growth of some kinds of tumor cells. It is also known that CCK participates in appetite control, analgesia through opiate, and symptoms of psychotic disorders including anxiety and panic disorder in the central nervous system via CCK-B receptors. Accordingly, drugs having a selective antagonistic action to CCK-B receptors are expected to be useful for the treatment of CCK-related disorders in the appetite control system, enhancement and prolongation of analgesia through opiate or non-opiate, induction of anesthesia or analgesia, and the treatment and prevention of symptoms of psychotic disorders including anxiety and panic disorders.

While amino acid (glutamic acid) derivatives such as Proglumide are reported as a CCK-B receptor antagonist, their binding activity to CCK-B receptors is very weak.

An object of the present invention is to provide a compound which selectively antagonizes to gastrin receptors without causing side effects attributed to the CCK-A receptor antagonism and inhibits gastric acid secretion in vivo and is useful for the treatment and prevention of diseases of digestive organs, such as peptic ulcers, gastritis, reflux esophagitis, and Zollinger-Ellison syndrome, and for the treatment of tumour originating in the gastrointestinal system and which also selectively antagonizes to CCK-B receptors without causing side effects attributed to the CCK-A receptor antagonism and is useful for the treatment of CCK-related disorders in the appetite control system, enhancement and prolongation of analgesia through opiate or non-opiate, induction of anesthesia or analgesia, and the treatment and prevention of symptoms of psychotic disorders including anxiety and panic disorder, and an intermediate useful for the synthesis of the compound.

DISCLOSURE OF THE INVENTION

We have conducted extensive investigations for the purpose of developing a selective gastrin receptor antagonist and a selective CCK-B receptor antagonist. As a result, we have found that the above purpose can be achieved by a compound represented by formula (I):

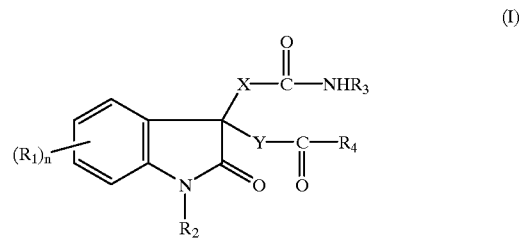

wherein $R_1$ represents a halogen atom, a lower alkyl group, a lower alkoxy group, a hydroxyl group, a nitro group, a trifluoromethyl group, a lower alkylthio group, an acyl group, a carboxyl group, a mercapto group, or a substituted or unsubstituted amino group; $R_2$ represents a hydrogen atom, a substituted or unsubstituted lower alkyl group, a substituted or unsubstituted lower alkenyl group, a substituted or unsubstituted lower alkynyl group, a substituted or unsubstituted lower alkoxy group, a substituted or unsubstituted acyl group, a substituted or unsubstituted aryl group, or a substituted or unsubstituted heterocyclic group; $R_3$ represents a substituted or unsubstituted lower alkyl group, a substituted or unsubstituted cycloalkyl group, a substituted or unsubstituted aryl group, or a substituted or unsubstituted heterocyclic group; $R_4$ represents a hydrogen atom, a substituted or unsubstituted lower alkyl group, a substituted or unsubstituted aryl group, a substituted or unsubstituted heterocyclic group, —$OR_5$, —$SR_5$, or —$NR_6R_7$, wherein $R_5$, $R_6$, and $R_7$, which may be the same or different, each represent a hydrogen atom, a substituted or unsubstituted lower alkyl group, a substituted or unsubstituted cycloalkyl group, a substituted or unsubstituted aryl group, a substituted or unsubstituted heterocyclic group, a lower alkoxy group, or a substituted or unsubstituted amino group; or $R_6$ and $R_7$ are taken together to form —$(CH_2)_m$— or —$(CH_2)_lNR_8(CH_2)_k$— (wherein k, l, and m each represent an integer of from 1 to 8; and $R_8$ represents a hydrogen atom or a lower alkyl group); X and Y, which may be the same or different, each represent —$CH_2$—, —NH— or —O—; and n represents an integer of from 0 to 4, or a salt thereof, thus having reached the present invention. We have also found that a compound represented by formula (II):

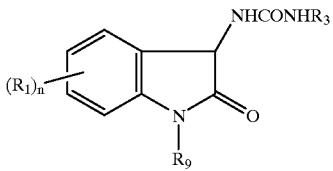

(II)

wherein $R_1$, $R_3$, and n are as defined above; and $R_9$ represents a group represented by formula (III):

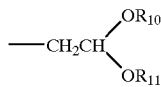

(III)

wherein $R_{10}$ and $R_{11}$ each represent a substituted or unsubstituted lower alkyl group,
or a group represented by formula (IV):

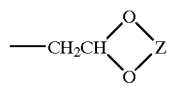

(IV)

wherein Z represents a substituted or unsubstituted lower alkylene group,
and a compound represented by formula (V):

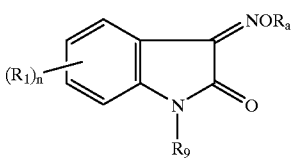

(V)

wherein $R_1$, $R_9$, and n are as defined above, are useful intermediates for the synthesis of compound represented by formula (I).

GENERAL DEFINITIONS OF TERMS USED

In the present invention, the term "lower alkyl group" denotes a straight-chain or branched alkyl group having 1 to 6 carbon atoms, including a methyl group, an ethyl group, a n-propyl group, an isopropyl group, a n-butyl group, a sec-butyl group, a t-butyl group, a pentyl group, and a hexyl group.

The term "lower alkenyl group" denotes a straight-chain or branched alkenyl group having from 2 to 6 carbon atoms, including a vinyl group, an allyl group, a butenyl group, a pentenyl group, and a hexenyl group.

The term "lower alkynyl group" means a straight-chain or branched alkynyl group having 2 to 6 carbon atoms, including an ethynyl group, a propynyl group, and a butynyl group.

The term "lower alkoxy group" denotes a straight-chain or branched alkyloxy group having 1 to 6 carbon atoms, including a methyloxy group, an ethyloxy group, a n-propyloxy group, an isopropyloxy group, a n-butyloxy group, a sec-butyloxy group, a t-butyloxy group, a pentyloxy group, and a hexyloxy group.

The term "acyl group" indicates a carbonyl group attaching a hydrogen atom, a substituted or unsubstituted alkyl group, a substituted or unsubstituted aryl group, a substituted or unsubstituted alkoxy group, a substituted or unsubstituted amino group, etc., including an alkylcarbonyl group, such as an acetyl group, a propionyl group, a pivaloyl group, and a cyclohexanecarbonyl group; and an arylcarbonyl group, such as a benzoyl group, a naphthoyl group and a toluoyl group.

The term "aryl group" means an aromatic hydrocarbon with one hydrogen atom removed therefrom, such as a phenyl group, a tolyl group, a xylyl group, a biphenyl group, a naphthyl group, an anthryl group, or a phenanthryl group.

The term "alkylene group" denotes a straight-chain or branched alkylene group having 1 to 6 carbon atoms, including a methylene group, an ethylene group, a propylene group, a butylene group, a pentylene group, and a hexylene group.

The term "cycloalkyl group" denotes a cyclic saturated hydrocarbon group having 3 to 8 carbon atoms, such as a cyclopropyl group, a cyclobutyl group, a cyclopentyl group, a cyclohexyl group or a cycloheptyl group. The substituted cycloalkyl group includes a menthyl group and an adamantyl group.

The term "aralkyl group" denotes a lower alkyl group substituted with an aryl group, such as a benzyl group, a diphenylmethyl group, a trityl group, a phenethyl group or a naphthylmethyl group, with a benzyl group or phenethyl group being preferred.

The term "heterocyclic group" means an aromatic heterocyclic group having at least one hetero atom, such as a pyridyl group, a furyl group, a thienyl group, an imidazolyl group, a pyrazinyl group or a pyrimidyl group.

The "substituent" includes a halogen atom, a lower alkyl group., a cycloalkyl group, an aryl group, a hydroxyl group, an alkoxy group, an aryloxy group, an alkylthio group, a heterocyclic group, a formyl group (which may be protected with an acetal, etc.), an alkylcarbonyl group, an arylcarbonyl group, a carboxyl group, an alkoxycarbonyl group, a substituted or unsubstituted amino group, an imino group, a thioacetal group, a nitro group, a nitrile group, and a trifluoromethyl group.

$R_1$ is preferably a lower alkyl group or nil (n=0), still preferably nil (n=0).

$R_2$ is preferably an alkoxy-substituted lower alkyl group, still preferably a lower alkyl group having two alkoxy groups or an —O—Z—O— group (wherein Z represents a substituted or unsubstituted lower alkylene group) on one carbon atom thereof. A 2,2-diethoxyethyl group is particularly preferred.

$R_3$ is preferably a substituted or unsubstituted aryl group, still preferably a phenyl group substituted with a lower alkyl group or a lower alkoxy group. A phenyl group substituted with a methyl group or a methoxy group is particularly preferred.

$R_4$ is preferably —$NR_6R_7$ in which one of $R_6$ and $R_7$ is a hydrogen atom with the other being a substituted or unsubstituted aryl group or a substituted or unsubstituted heterocyclic group, still preferably —$NR_6R_7$ in which one of $R_6$ and $R_7$ is a hydrogen atom with the other being a phenyl group substituted with a lower alkyl group, a lower alkoxy group or a substituted or unsubstituted amino group, particularly a phenyl group substituted with a methyl group or an N,N-dimethylamino group.

X is preferably —NH—.

Y is preferably —$CH_2$—.

Of optically active compounds of formula (I) or salts thereof preferred are (+)-compounds.

The compounds of the present invention are novel compounds which have not been reported in any literature and can be synthesized, for example, as follows.

Reaction Route 1:

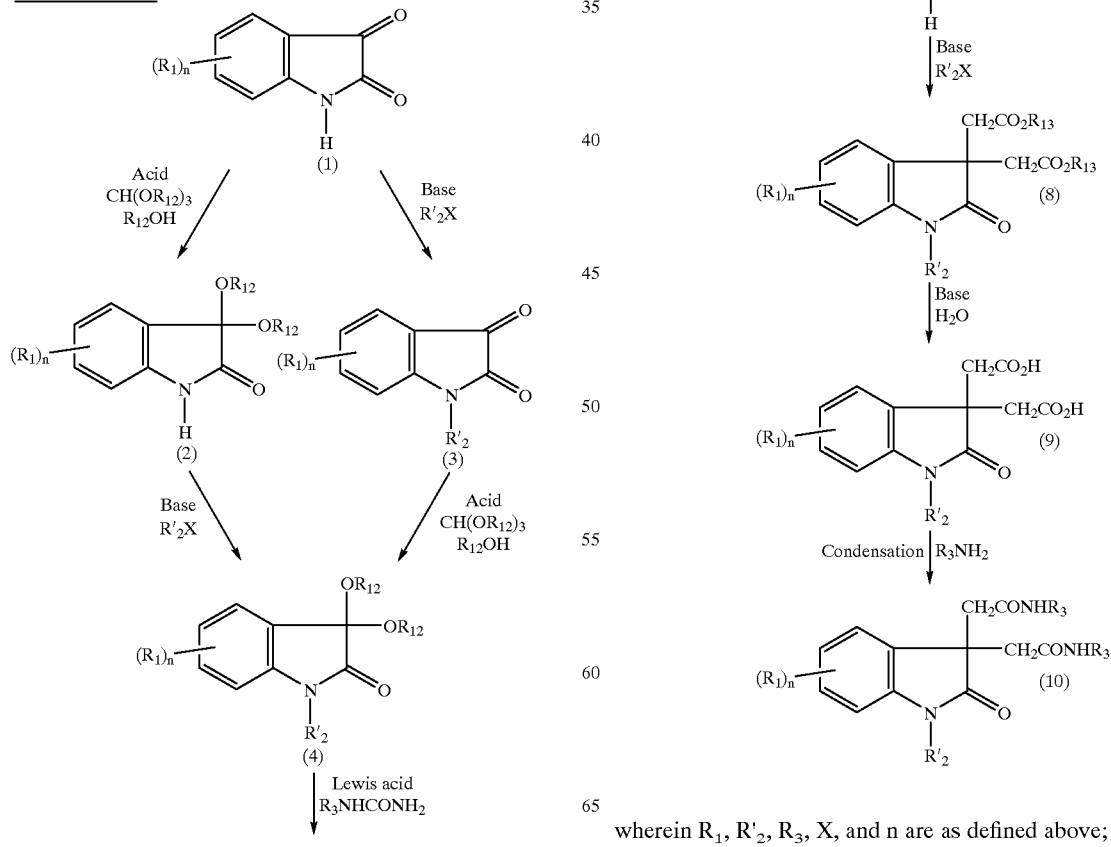

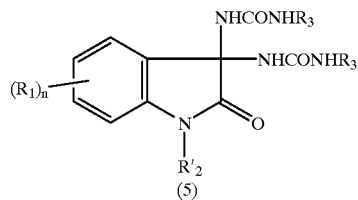

wherein $R_1$, $R_3$, and n are as defined above; $R_{12}$ represents a lower alkyl group; $R'_2$ represents a substituted or unsubstituted lower alkyl group, a substituted or unsubstituted lower alkenyl group, a substituted or unsubstituted lower alkynyl group, a substituted or unsubstituted aryl group, or a substituted or unsubstituted heterocyclic group; and X represents a halogen atom or a trifluoromethanesulfonyloxy group.

Reaction Route 2:

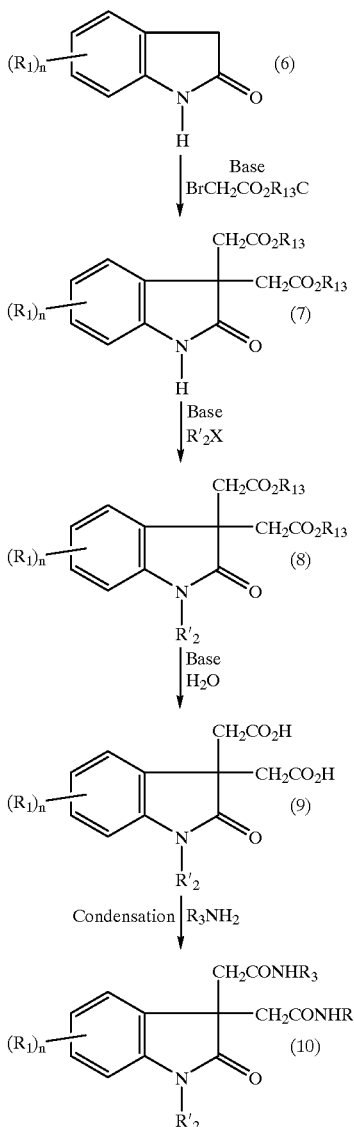

wherein $R_1$, $R'_2$, $R_3$, X, and n are as defined above; and $R_{13}$ represents a lower alkyl group.

Reaction Route 3:
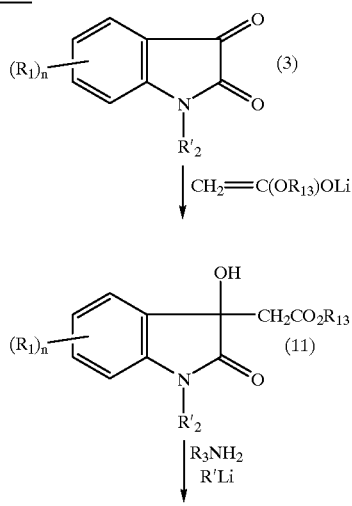
wherein $R_1$, $R'_2$, $R_3$, $R_{13}$, and n are as defined above; R' represents a lower alkyl group; and $R_{14}$ represents a substituted or unsubstituted lower alkyl group, a substituted or unsubstituted cycloalkyl group, a substituted or unsubstituted aryl group, or a substituted or unsubstituted heterocyclic group.
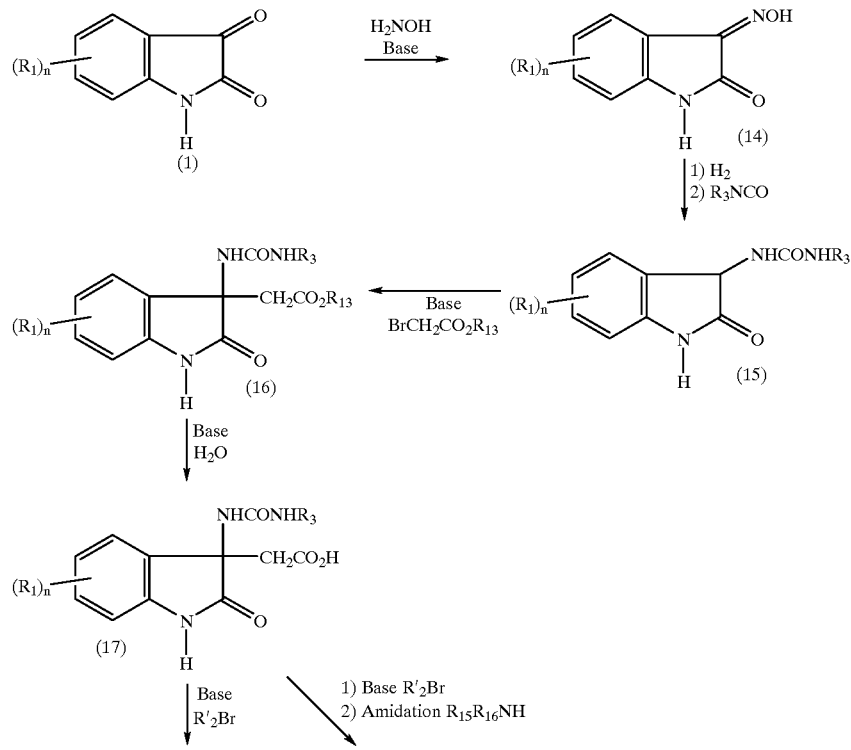

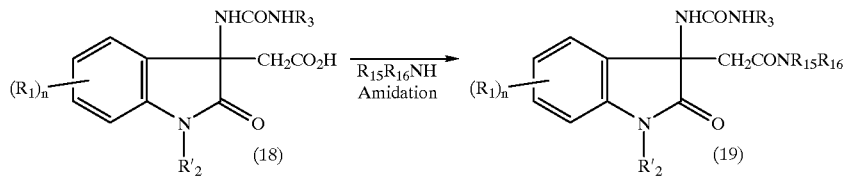

wherein $R_1$, $R'_2$, $R_3$, $R_{13}$, and n are as defined above; and $R_{15}$ and $R_{16}$, which may be the same or different, each represent a hydrogen atom, a substituted or unsubstituted lower alkyl group, a substituted or unsubstituted cycloalkyl group, a substituted or unsubstituted aryl group, a substituted or unsubstituted heterocyclic group, a lower alkoxy group, or a substituted or unsubstituted amino group; or $R_{15}$ and $R_{16}$ are taken together to form $-(CH_2)_m-$ or $-(CH_2)_l NR_8(CH_2)_k-$, wherein k, l, and m each represent an integer of from 1 to 8; and $R_8$ represents a hydrogen atom or a lower alkyl group.

Reaction Route 5:

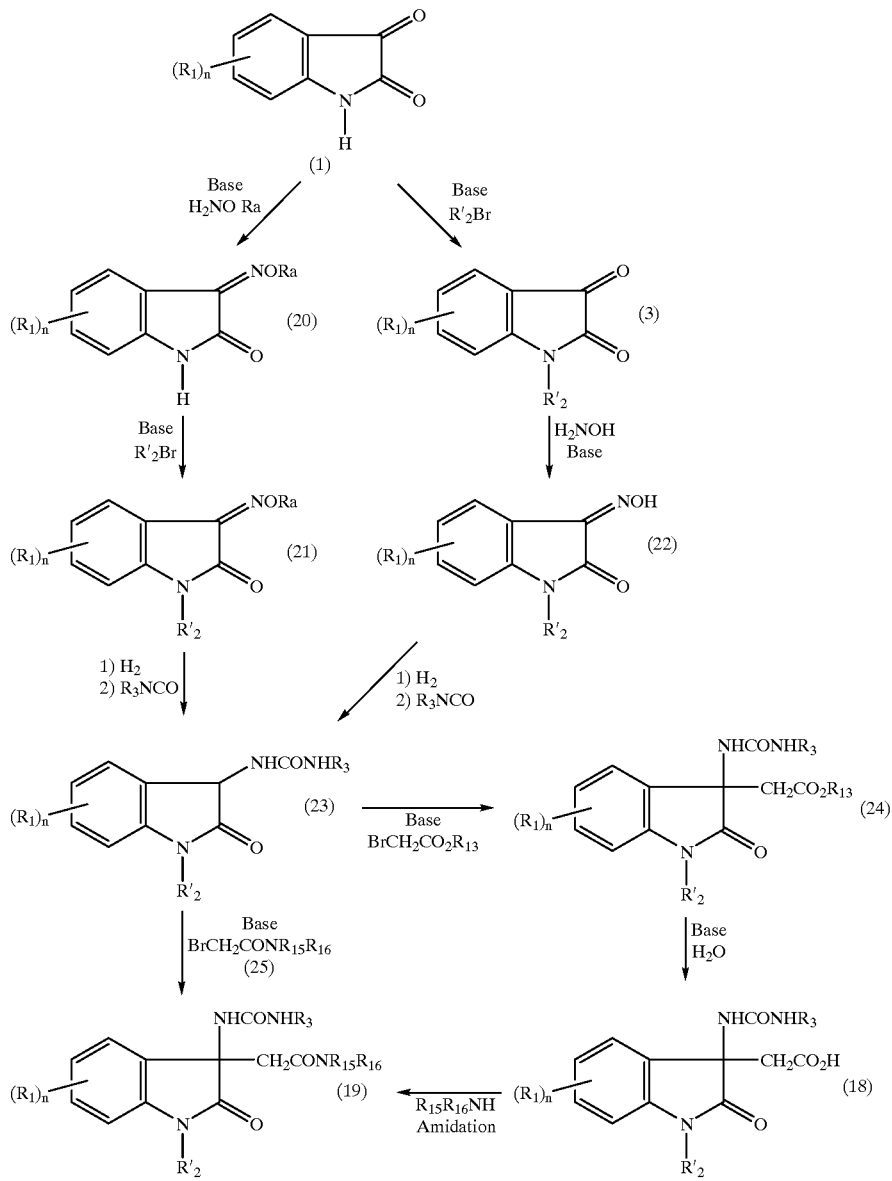

wherein $R_1$, $R'_2$, $R_3$, $R_{13}$, $R_{15}$, $R_{16}$, and n are as defined above; and $R_a$ preferably represents a substituted or unsubstituted lower alkyl group, still preferably a substituted or unsubstituted methyl group, most preferably a methyl group or a benzyl group.

Reaction Route 6:

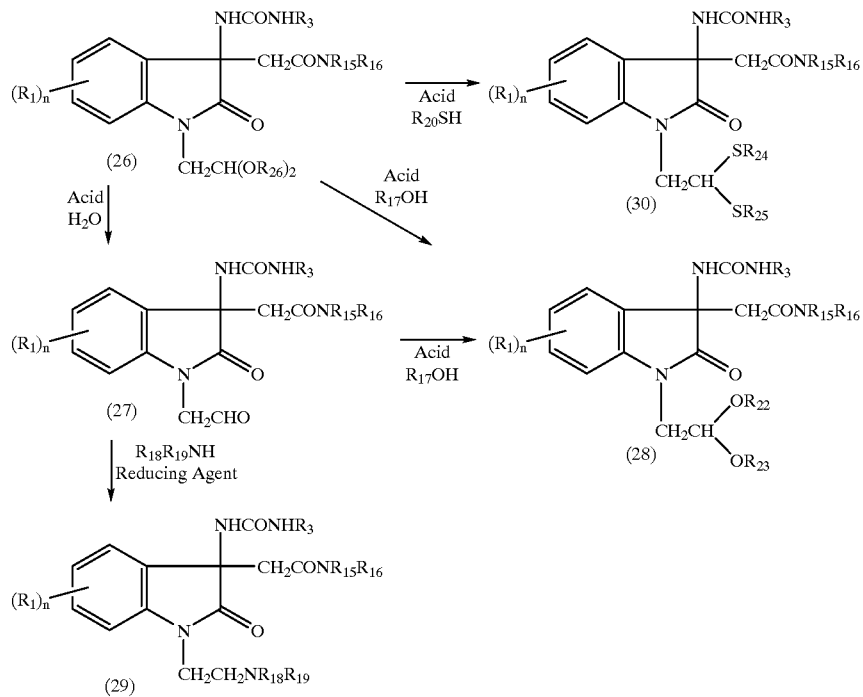

wherein $R_1$, $R_3$, $R_{15}$, $R_{16}$, and n are as defined above; $R_{26}$ represents a lower alkyl group; $R_{17}$ represents a lower alkyl group or a lower hydroxyalkyl group; $R_{18}$ and $R_{19}$ each represent a lower alkyl group, or they are taken together to form an alkylene group; $R_{20}$ represents a lower alkyl group or a lower mercaptoalkyl group; $R_{22}$ and $R_{23}$ each represent a lower alkyl group, or they are taken together to form an alkylene group; and $R_{24}$ and $R_{25}$ each represent a lower alkyl group, or they are taken together to form an alkylene group.

Reaction Route 7:

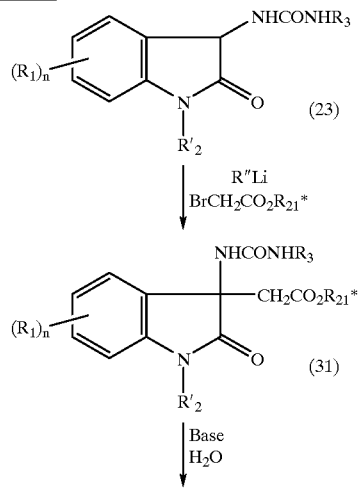

-continued

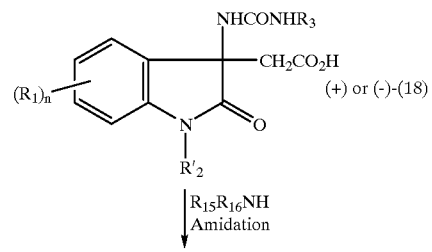

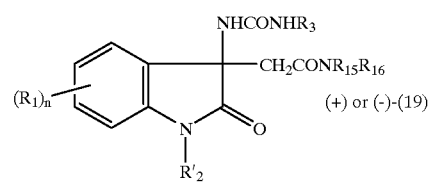

wherein $R_1$, $R'_2$, $R_3$, $R_{15}$, $R_{16}$, and n are as defined above; R" represents a lower alkyl group, a primary amino group, a secondary amino group or an alkoxy group; and $R_{21}*$ represents an optically active group.

Reaction Route 8:

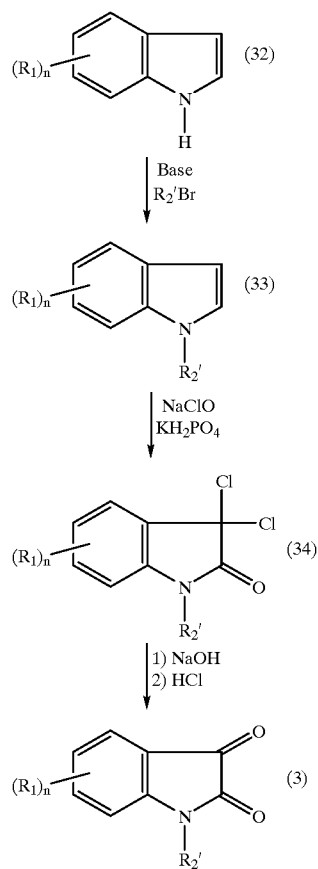

wherein $R_1$, $R'_1$ and n are as defined above.

Diurea derivative (5) can be prepared by substitution reaction between the acetal moiety of acetal intermediate (4) and an urea derivative as shown in Reaction Route 1. Intermediate (4) can be prepared by two reactions, i.e., alkylation and acetal formation, whichever may precede, as shown in Reaction Route 1.

The isatin derivative which can be used as a starting material in this process is a known compound and is commercially available or can easily be synthesized in a conventional manner. Various urea derivatives are also commercially available or can easily be synthesized in a conventional manner (*J. Heterocyclic Chem.*, Vol. 19, p. 1453 (1982)).

The preparation of diurea derivative (5) can preferably be carried out as follows. Isatin derivative (1) is dissolved or suspended in an inert solvent, such as dry N,N-dimethylformamide, dry dimethyl sulfoxide or dry tetrahydrofuran, and a requisite amount of a base, such as a metal hydride or a metal alkoxide, preferably sodium hydride or potassium t-butoxide, is added thereto at a temperature in the range from ice-cooling to room temperature. After stirring the mixture for a while at a temperature in the range from ice-cooling to room temperature, an equimolar amount or a slight excess, with respect to isatin derivative (1), of a halide is added thereto, followed by stirring for 1 to 15 hours at room temperature or under heating. After completion of the reaction, the solvent is removed by evaporation under reduced pressure. Water is added to the residue, and the mixture is extracted with an appropriate solvent, such as chloroform or ethyl acetate, dried, and concentrated under reduced pressure. The resulting crude product is purified by a proper method to obtain N-substituted isatin (3).

Then, N-substituted isatin (3) and an adequate amount of an appropriate trialkyl orthoformate are dissolved or suspended in an appropriate alcohol, and an adequate amount of an acid catalyst, for example, p-toluenesulfonic acid monohydrate, camphorsulfonic acid or sulfuric acid, is added thereto, followed by heating for 4 to 48 hours with stirring. The reaction mixture is concentrated under reduced pressure, and to the residue is added a base, for example, saturated aqueous sodium hydrogencarbonate, followed by extraction with an appropriate solvent, such as chloroform or ethyl acetate. The extract is dried and concentrated under reduced pressure. The resulting crude product is purified by an appropriate method to obtain acetal intermediate (4).

Alternatively, acetal intermediate (4) can be obtained by conducting the above-mentioned two reactions in reverse order, i.e., via intermediate (2) shown in Reaction Route 1. This process is preferred in case where the reaction for synthesizing N-substituted isatin (3) requires heating.

An excess, with reference to acetal intermediate (4), preferably 2 to 3 mol, per mol of acetal intermediate (4), of a Lewis acid, such as anhydrous aluminum chloride, boron trifluoride ethyl etherate, titanium tetrachloride, tin tetrachloride, magnesium bromide ethyl etherate, or zinc bromide, preferably anhydrous aluminum chloride, is dissolved in an inert solvent, such as dry tetrahydrofuran, dichloromethane, toluene, or dry dioxane, preferably dry tetrahydrofuran. To the solution are added successively a solution of acetal intermediate (4) in dry tetrahydrofuran, etc. and an urea derivative in excess, preferably in an amount of 2 mol per mol of acetal intermediate (4) at a temperature in the range from ice-cooling to room temperature, followed by heating for 1 to 8 hours with stirring. After completion of the reaction, an appropriate organic solvent, such as ethyl acetate, is added to the reaction mixture, and the mixture is washed with water, dried, and concentrated under reduced pressure. The residue is purified by a proper method to obtain diurea derivative (5).

Diamide derivative (10) can be prepared by dialkylation of the 3-position of commercially available 2-oxindole (6), followed by alkylation of the 1-position, followed by conversion of ester to amide as illustrated in Reaction Route 2.

The preparation of diamide derivative (10) can preferably be carried out as follows. 2-Oxindole (6) is dissolved in an inert solvent, such as dry dimethyl sulfoxide, dry N,N-dimethylformamide or dry tetrahydrofuran, preferably dry dimethyl sulfoxide, and a solution of an equimolar amount of a base, such as a metal hydride or a metal alkoxide, preferably sodium hydride or potassium t-butoxide, in dry dimethyl sulfoxide is added thereto at a temperature in the range from ice-cooling to room temperature, followed by stirring at a temperature in the range from ice-cooling to room temperature for several minutes. An equimolar amount of an appropriate bromoacetic ester with reference to (6) is then added thereto, followed by stirring at room temperature for several tens of minutes. To the reaction mixture are further added an equimolar amount of the same base as used above and an equimolar amount of the same bromoacetic ester as used above at the same temperature, followed by stirring at room temperature for several tens of minutes. After completion of the reaction, water is added to the residue, and the mixture is extracted with an appropriate solvent, such as diethyl ether. The extract is dried and concentrated under reduced pressure. Since the resulting crude product contains a 1-substituted derivative, it is purified by a proper method, such as silica gel column chromatography, to give both 3,3-bis (alkoxycarbonylmethyl)indolin-2-one (7) and 1,3,3-tris (alkoxycarbonylmethyl)indolin-2-one.

3,3-Bis(alkoxycarbonylmethyl)indolin-2-one (7) is dissolved or suspended in an inert solvent, such as dry N,N-dimethylformamide, dry dimethyl sulfoxide or dry tetrahydrofuran, and a requisite amount of a base, such as a metal hydride or a metal alkoxide, preferably sodium hydride or potassium t-butoxide, is added thereto at a temperature in the range from ice-cooling to room temperature, followed by stirring for several minutes at a temperature in the range from ice-cooling to room temperature. An equimolar amount or a slight excess, with respect to (7), of an appropriate halide is added thereto, followed by stirring for 1 to 15 hours at room temperature or under heating. After completion of the reaction, the solvent is removed by evaporation under reduced pressure. Water is added to the residue, and the mixture is extracted with an appropriate solvent, such as chloroform or ethyl acetate, dried, and concentrated under reduced pressure. The resulting crude product may be either purified by a proper method to obtain 1-substituted 3,3-bis(alkoxycarbonylmethyl) indolin-2-one (8) or be used in the subsequent reaction without further purification.

1-Substituted 3,3-bis(alkoxycarbonylmethyl)indolin-2-one (8) is dissolved in a solvent uniformly miscible with water, such as ethanol or methanol, and an aqueous solution of a moderately excess base, such as potassium hydroxide, sodium hydroxide or potassium carbonate, is added thereto at room temperature, followed by stirring for 1 to 24 hours at room temperature or under heating. After completion of the reaction, the reaction mixture is concentrated under reduced pressure. The concentrate is dissolved in water and washed with an appropriate organic solvent, such as chloroform. The aqueous layer is acidified with an acid, e.g., 2N hydrochloric acid and then extracted with an appropriate organic solvent, such as ethyl acetate, to obtain 1-substituted 3,3-bis(hydroxycarbonylmethyl)indolin-2-one (9). The crude product as obtained may be used in the subsequent reaction either without purification or after being purified by an appropriate method.

1-Substituted 3,3-bis(hydroxycarbonylmethyl)indolin-2-one (9) is converted to an amide compound in a conventional manner to obtain diamide compound (10). For example, 1-substituted 3,3-bis(hydroxycarbonylmethyl)indolin-2-one (9) is dissolved in an inert solvent, such as dry N,N-dimethylformamide or dichloromethane, and 2 to 4 moles, per mol of (9), of dicyclohexylcarbodiimide or 1-ethyl-3-(3-dimethylaminopropyl)carbodiimide hydrochloride is added thereto as a condensing agent. Subsequently, 0 to 4 mol of 1-hydroxybenzotriazole or 4-dimethylaminopyridine as an activating agent and 2 to 4 mol of an amine, each per mol of (9) are preferably added thereto at room temperature. The mixture is stirred at room temperature for 6 to 24 hours. To the reaction mixture, either as obtained or after concentration under reduced pressure, is added dilute hydrochloric acid. The product is extracted with an appropriate organic solvent, and the organic layer is washed with an appropriate base, such as saturated aqueous sodium hydrogencarbonate, dried, and concentrated. The concentrate is purified by an appropriate method to obtain diamide compound (10).

As shown in Reaction Route 3, monocarbamate (13) can be prepared by Aldol reaction of N-substituted isatin derivative (3) as a starting material, conversion of the reaction product to an amide compound, and reaction of the resulting tertiary alcohol (12) with an isocyanate using a catalyst.

The preparation of monocarbamate derivative (13) can preferably be carried out as follows. A lithium enolate of an acetic ester is prepared by mixing a lithium salt of a secondary amine, such as lithium diisopropylamide or lithium hexamethyldisilazide, with an acetic ester at an equimolar ratio in a solvent which gives no adverse influence to the reaction, such as dry tetrahydrofuran, dry diethyl ether or dry dioxane, preferably dry tetrahydrofuran, by stirring under a nitrogen atmosphere at a low temperature for several minutes. To the resulting reaction solution is added 0.5 mol of N-substituted isatin (3) per mol of the lithium enolate at a low temperature, followed by stirring at a low temperature for several tens of minutes, and the reaction mixture is poured into water to quench the reaction. The reaction product is extracted with an appropriate organic solvent, and the extract is dried and concentrated to obtain ester intermediate (11). This crude product (11) may be used in the subsequent reaction either without purification or after purification by a proper method.

An amine is dissolved in a solvent giving no adverse influence to the reaction, such as dry tetrahydrofuran, dry diethyl ether or dry dioxane, preferably dry tetrahydrofuran, and an equimolar amount of an alkyl lithium, preferably n-butyl lithium, is added to the solution under a nitrogen atmosphere at a low temperature, followed by stirring at a low temperature for several minutes. To the resulting solution is added 0.5 mol of ester intermediate (11) per mol of the amine, and the mixture is stirred at a low temperature for several tens of minutes. The reaction mixture is poured into water to quench the reaction, and the product is extracted with an appropriate organic solvent. The extract is dried and concentrated, and the concentrate is purified by a proper method to obtain amide intermediate (12).

Amide intermediate (12) and excess isocyanate compound are dissolved in an inert solvent, such as dry tetrahydrofuran, dichloromethane, acetonitrile or toluene, preferably dry tetrahydrofuran, and a small proportion, with reference to (12), of an acid or a base, such as a titanium tetraalkoxide, a boron trifluoride ethyl etherate, dibutyltin diacetate or diisopropylethylamine, preferably dibutyltin diacetate, is added to the solution, followed by stirring for 10 to 24 hours at room temperature or under heating. The reaction mixture is washed with water, extracted with an appropriate solvent, dried, and concentrated. The concentrate is purified by a proper method to obtain monocarbamate compound (13).

Monourea compound (19) can be prepared through either of the processes illustrated in Reaction Routes 4 and 5.

Some ureido intermediates (15) shown in Reaction Route 4 are known compounds and can be synthesized by starting with isatin derivative (1) in accordance with the process described in patents (Japanese Patent Publication Nos. 6710/92 and 6711/92). An acetic ester is bonded to the thus prepared ureido intermediate (15), and the resulting ester is hydrolyzed to give carboxylic acid (17). The 1-position of (17) is selectively alkylated to give compound (18), which is then converted to monourea compound (19) by amidation. The alkylation and the subsequent amidation of carboxylic acid (17) may be carried out in one step.

Ureido intermediate (23) in Reaction Route 5 can be synthesized by starting with N-substituted isatin (3) in accordance with the process described in patents (Japanese Patent Publication Nos. 6710/92 and 6711/92). Alternatively, it may be prepared by converting isatin derivative (1) to alkyloxime or aralkyloxime (20), for example, methyloxime or benzyloxime, alkylating the 1-position, hydrogenation of oxime, and then leading the product to urea. N-Substituted isatin (3) can also be synthesized by alkylating the 1-position of starting indole (32) to obtain 1-substituted indole (33), followed by oxidizing the indole ring with, for example, sodium hypochlorite to give (34), which is then hydrolyzed as shown in Reaction Route 8. Where a bulky group, such as a secondary alkyl group, a 2,2-dialkoxyethyl group or a 2,2-dialkylethyl group, is to be introduced to the 1-position, the reaction route by way of alkyloxime or aralkyloxime (20) or the route including oxidation of 1-substituted indole (33) are preferred. An acetic ester is bonded to the thus prepared ureido intermediate (23), and the resulting ester is hydrolyzed to give carboxylic acid (18), which is then converted to monourea compound (19) by amidation. Alternatively, an acetamide derivative can directly be added to (23) to prepare (19). Most of bromoacetamide derivatives (25) which can be used in this reaction are known compounds and can easily be synthesized by mixing bromoacetyl bromide and an amine in the presence of a base.

The preparation of monourea compound (19) through Reaction Route 4 can preferably be carried out as follows. Isatin derivative (1) is dissolved in an inert solvent, such as ethanol or methanol, and an equimolar or excessive molar amount, with reference to (1), of a hydroxylamine hydrochloride or a hydroxylamine sulfate, and the same quantity of a base, such as a sodium acetate aqueous solution, are added thereto, followed by stirring for 1 to 10 hours at room temperature or under ice-cooling. The reaction mixture is concentrated, and the concentrate is purified by a proper method to give oxime derivative (14). Oxime derivative (14) is stirred in an inert solvent, such as ethanol, methanol or acetic acid, in the presence of an appropriate catalyst, such as palladium-on-carbon, rhodium-on-carbon, platinum oxide, or Raney nickel, under a hydrogen atmosphere of 1 to 6 atm at room temperature. After removal of the catalyst by filtration, the filtrate is concentrated to give an amine intermediate. Since this compound is susceptible to air oxidation, it is preferably subjected to the subsequent reaction without further purification. The unpurified product is dissolved in an inert solvent, such as dichloromethane, chloroform, N,N-dimethylformamide, or acetonitrile, and an equimolar or slightly excessive amount, with reference to the amine, of an isocyanate is added thereto at a temperature in the range from ice-cooling to room temperature, followed by stirring at a temperature in the range from ice-cooling to room temperature for 1 to 10 hours. The reaction product is purified by a proper method to give ureido intermediate (15).

Ureido intermediate (15) is dissolved in an inert solvent, such as dry N,N-dimethylformamide, dry dimethyl sulfoxide or dry tetrahydrofuran, preferably dry dimethyl sulfoxide, and a solution of an equimolar amount, with reference to ureido intermediate (15), of a base, such as a metal hydride or a metal alkoxide, preferably sodium hydride or potassium t-butoxide, in dry dimethyl sulfoxide is added thereto at a temperature in the range from ice-cooling to room temperature, followed by stirring at a temperature in the range from ice-cooling to room temperature for 10 to 30 minutes. Then, a bromoacetic ester is added thereto in an equimolar amount with reference to ureido intermediate (15), and the mixture is stirred at room temperature for several tens of minutes. After completion of the reaction, water is added to the reaction mixture, and the mixture is extracted with an appropriate solvent, such as diethyl ether. The extract is dried and concentrated under reduced pressure, and the residue is purified by a proper method to obtain ester compound (16).

Ester compound (16) is stirred in a solvent uniformly miscible with water, such as ethanol or methanol, together with an aqueous solution of a moderate excess of a base, such as potassium hydroxide, sodium hydroxide or potassium carbonate, at room temperature for 1 to 24 hours. After completion of the reaction, the reaction mixture is concentrated under reduced pressure. The concentrate is dissolved in water and washed with an appropriate organic solvent, such as chloroform. The aqueous layer is acidified with 2N hydrochloric acid and then extracted with an appropriate organic solvent, such as ethyl acetate, to obtain carboxylic acid (17). The resulting crude product may be used in the subsequent reaction either as it is or after being purified by a proper method.

Carboxylic acid (17) is dissolved in a solvent giving no adverse influence to the reaction, such as dry dimethyl sulfoxide or dry tetrahydrofuran, preferably dry dimethyl sulfoxide, and a solution of 2 mol, per mol of carboxylic acid (17), of a base, such as a metal hydride or a metal alkoxide, preferably sodium hydride or potassium t-butoxide, in dry dimethyl sulfoxide is added thereto at room temperature, followed by stirring at room temperature for 10 to 30 minutes. A halide is added thereto in an equimolar amount with carboxylic acid (17), followed by stirring at room temperature for several tens of minutes. After completion of the reaction, water is added to the reaction mixture, and the mixture is extracted with an appropriate solvent, such as diethyl ether. The extract is dried and concentrated under reduced pressure to obtain 1-alkyl compound (18). The resulting crude product may be used in the subsequent reaction either as it is or after being purified by a proper method.

1-Alkyl compound (18) is dissolved in an inert solvent, such as dry N,N-dimethylformamide or dichloromethane, and 1 to 4 mol, per mol of 1-alkyl compound (18), of a condensing agent, such as dicyclohexylcarbodiimide or 1-ethyl-3-(3-dimethylaminopropyl)carbodiimide hydrochloride, is added to the solution. To the solution are further added successively 0 to 4 mol of 1-hydroxybenzotriazole or 4-dimethylaminopyridine as an activating agent and 1 to 4 mol of an amine, each per mol of 1-alkyl compound (18) at room temperature. The mixture is stirred at room temperature for 1 to 24 hours.

Alternatively, 1-alkyl compound (18) is dissolved in an inert solvent, such as chloroform or dichloromethane, and an equimolar amount or a slight excess, with reference to 1-alkyl compound (18), of a base, such as 4-dimethylaminopyridine, triethylamine, pyridine or a mixture thereof, and an equimolar amount of a halogenating agent, preferably thionyl chloride, are added thereto at 0° C. to room temperature. After stirring the mixture for 30 minutes to 2 hours, an equimolar amount or a slight excess, with reference to 1-alkyl compound (18), of a base, such as 4-dimethylaminopyridine, triethylamine, pyridine or a mixture thereof, and an equimolar amount or a slight excess of an amine are added thereto, followed by stirring at room temperature or under ice-cooling for 30 minutes to 4 hours.

Dilute hydrochloric acid is added to the reaction mixture either as obtained or after being concentrated under reduced pressure, and the mixture is extracted with an appropriate organic solvent. The organic layer is washed with an appropriate base, such as saturated aqueous sodium hydrogencarbonate, dried, and concentrated. The residue is purified by an appropriate method to give monourea compound (19).

Monourea compound (19) can also be prepared from carboxylic acid (17) without isolating (18). Carboxylic acid (17) is dissolved in a solvent giving no adverse influence to the reaction, such as dry N,N-dimethylformamide, dry dimethyl sulfoxide or dry tetrahydrofuran, preferably dry dimethyl sulfoxide. A solution of 2 mol, per mol of carboxylic acid (17), of a base, such as a metal hydride or a metal alkoxide, preferably sodium hydride or potassium t-butoxide, in dry dimethyl sulfoxide is added to the solution at room temperature, followed by stirring at room temperature for 10 to 30 minutes. To the mixture is further added a halide in an equimolar amount with carboxylic acid (17), followed by stirring at room temperature for several tens of minutes. After completion of the reaction, 1 to 3 mol, per mol of carboxylic acid (17), of a condensing agent, such as dicyclohexylcarbodiimide or 1-ethyl-3-(3-dimethylaminopropyl)carbodiimide hydrochloride is added to the reaction mixture. Subsequently, 0 to 3 mol, per mol of 1-alkyl compound (18), of 1-hydroxybenzotriazole or 4-dimethylaminopyridine is preferably added thereto as an activating agent, and then 1 to 3 mol, per mol of 1-alkyl compound (18), of an amine is further added thereto, followed by stirring at room temperature for 6 to 24 hours. Water is added to the reaction mixture, and the mixture is extracted with an appropriate solvent, such as diethyl ether. The extract is dried, concentrated under reduced pressure, and purified by an appropriate method to give monourea compound (19).

The preparation of monourea compound (19) through Reaction Route 5 can preferably be carried out as follows. First of all, ureido intermediate (23) with its 1-position alkylated is prepared by starting with N-substituted isatin (3), which is synthesized by the process shown in Reaction Route 8 or by alkylation of isatin derivative (1), in the same manner as in the preparation of ureido intermediate (15) shown in Reaction Route 4. Alternatively, ureido intermediate (23) may be prepared as follows. Isatin derivative (1) is dissolved or suspended in an inert solvent, such as ethanol or methanol, and to the solution or suspension are added an equimolar or excess molar amount, with reference to (1), of an O-alkylhydroxylamine or an O-aralkylhydroxylamine, such as O-methyl or benzylhydroxylamine hydrochloride, and an aqueous solution of excess base, such as sodium acetate, and the mixture is stirred at room temperature for 1 to 10 hours. The reaction mixture is concentrated and purified by a proper method to obtain alkyloxime (e.g., methyloxime) or aralkyloxime (e.g., benzyloxime) derivative (20). Then, an equimolar amount or a slight excess, with reference to (20), of a base, such as sodium hydride or potassium t-butoxide, is dissolved or suspended in an inert solvent, such as dry N,N-dimethylformamide, dry dimethyl sulfoxide or dry tetrahydrofuran. Alkyloxime derivative or aralkyloxime derivative (20) is added to the solution or suspension at room temperature or under ice-cooling. After stirring at the same temperature for 30 minutes to 1 hour, an equimolar amount or a slight excess, with reference to (20), of a halide is added thereto, followed by further stirring at room temperature or under heating for 1 to 15 hours. After completion of the reaction, the solvent was evaporated under reduced pressure, water is added to the residue, and the mixture is extracted with an appropriate solvent. The extract is dried and concentrated under reduced pressure. The resulting crude product is purified by a proper method to obtain N-substituted compound (21), which is hydrogenated and reacted with isocyanate in the same manner as for the preparation of ureido intermediate (15) shown in Reaction Route 4 to thereby obtain ureido intermediate (23) with the 1-position alkylated.

The thus obtained ureido intermediate (23) is subjected to acetic ester addition reaction and ester hydrolysis reaction as shown in Reaction Route 5 in the same manner as in the preparation of carboxylic acid (17) shown in Reaction Route 4 to give intermediate (18) common to both reaction routes, which is converted to monourea compound (19) in the same manner as in Reaction Route 4.

Alternatively, monourea compound (18) can be prepared from ureido intermediate (23) in one step as described below. Ureido intermediate (23) is dissolved in an inert solvent, such as dry N,N-dimethylformamide, dry dimethyl sulfoxide or dry tetrahydrofuran, preferably dry dimethyl sulfoxide. To the solution is added a solution of an equimolar amount, with reference to ureido intermediate (23), of a base, such as a metal hydride or a metal alkoxide, preferably sodium hydride or potassium t-butoxide, in dried dimethyl sulfoxide at a temperature in the range from ice-cooling to room temperature, followed by stirring at a temperature in the range from ice-cooling to room temperature for 10 to 30 minutes. To the solution is further added an equimolar amount or a slight excess, with reference to ureido intermediate (23), of a bromoacetamide derivative (25), followed by stirring at room temperature for several tens of minutes. After completion of the reaction, water is added to the reaction mixture, and the mixture is extracted with an appropriate solvent, such as diethyl ether. The extract is dried and concentrated under reduced pressure. The residue is purified by a proper method to give monourea compound (19).

The preparation of N-substituted isatin (3) according to Reaction Route 8 can preferably be carried out as follows. Indole (32) is dissolved in a solvent giving no adverse influence to the reaction, such as dry N,N-dimethylformamide or dry tetrahydrofuran, preferably dry dimethyl sulfoxide, and a solution of an equimolar amount or an excess, with reference to indole (32), of a base, such as sodium hydride or potassium t-butoxide, in dry dimethyl sulfoxide, is added thereto at room temperature, followed by stirring at room temperature for 10 minutes to 1 hour. An equimolar amount or an excess molar amount, with reference to indole (32), of a halide is then added thereto, followed by stirring at room temperature or under heating for several tens of minutes to 10 hours. After completion of the reaction, water is added to the reaction mixture, followed by extraction with an appropriate solvent, such as diethyl ether. The extract is dried and concentrated under reduced pressure to give 1-substituted indole (33). The resulting crude product may be used in the next reaction or may be purified by a proper method. Then, 1-substituted indole (33) and, as a proton source, excess potassium dihydrogenphosphate or sodium dihydrogenphosphate are suspended in an appropriate solvent, such as ethyl acetate, and an aqueous solution of excess sodium hypochlorite is added thereto at room temperature or under ice-cooling, followed by stirring at that temperature for 5 to 30 minutes. After completion of the reaction, the reaction mixture is washed successively with water and a base, dried, and concentrated to give dichloro compound (34). The resulting crude product may be used in the subsequent reaction or may be purified by a proper method. Dichloro compound (34) is dissolved in an appropriate solvent, such as dimethyl sulfoxide, and excess base suitable for hydrolysis, for example, an aqueous solution of sodium hydroxide, is added thereto dropwise, followed by stirring for 10 minutes to 1 hour. To the mixture is slowly added an acid, e.g., concentrated hydrochloric acid, in excess over the base previously added, followed by stirring at room temperature for several hours. To the reaction mixture is added ethyl acetate, and the mixture is washed successively with water and a base. The organic layer is dried and concentrated to give N-substituted isatin (3). The resulting crude product can be used as an intermediate in Reaction Route 5 either without purification or after being purified by a proper method.

Of monourea compounds (19), those containing an acetal group or an amino group in the substituent at the 1-position can be prepared by the processes shown in Reaction Routes 4 and 5. In addition, monourea compound (19) containing acetal at the 1-substituent, i.e., monourea compound (28) can be prepared by acetal exchange from another acetal compound or by hydrolyzing the another acetal compound to once give aldehyde compound (27) which is then converted to acetal compound (28). Monourea compound (19) containing an amino group at the 1-substituent, i.e., monourea compound (29) can be prepared by reductive amination reaction of aldehyde compound (27).

The preparation of monourea compound (28) containing acetal at the 1-substituent can preferably be carried out as follows. Acetal compound (26) prepared by the process shown in Reaction Route 4 or 5 is dissolved in an alcohol for acetal exchange and stirred for 6 hours to 2 days while heating in the presence of an appropriate acid, such as p-toluenesulfonic acid, sulfuric acid or camphorsulfonic acid, as a catalyst. The reaction mixture is concentrated, and an appropriate base, for example, an aqueous solution of sodium hydrogencarbonate, is added thereto, followed by extraction with an appropriate organic solvent. The extract is dried and concentrated under reduced pressure. The residue is purified by a proper method to obtain (28). Alternatively, (26) is dissolved or suspended in an inert solvent, such as acetone, an alcohol, water or a mixture thereof, and an adequate amount of an appropriate acid, such as p-toluenesulfonic acid, sulfuric acid or camphorsulfonic acid, is added thereto, followed by stirring at room temperature or under heating for 1 to 18 hours. The reaction mixture is concentrated, an appropriate base, e.g., a sodium hydrogencarbonate aqueous solution, is added thereto, the mixture is extracted with an appropriate organic solvent, and the extract is dried and concentrated under reduced pressure to give aldehyde compound (27). This crude product may be used in the subsequent reaction without purification or after being purified by a proper method. Aldehyde compound (27) and an appropriate alcohol or diol in excess over aldehyde compound (27) are dissolved or suspended in an inert solvent, preferably toluene or benzene, and stirred in the presence of an appropriate acid catalyst, such as p-toluenesulfonic acid, sulfuric acid or camphorsulfonic acid, for 6 to 48 hours under heating while azeotropically removing produced water together with the solvent. The reaction mixture is washed with an appropriate base, such as an aqueous solution of sodium hydrogencarbonate, dried, and concentrated. The concentrate is purified by a proper method to give acetal compound (28).

The preparation of monourea compound (28) containing an amino group at the 1-substituent can preferably be carried out as follows. Aldehyde compound (27) and an equivalent or excess of an amine or an aqueous solution thereof are dissolved in an inert solvent, such as methanol. After neutralizing the solution with an appropriate acid, such as acetic acid, trifluoroacetic acid or hydrochloric acid, an equivalent or excess, with reference to (27), of a hydrogenating agent, such as sodium cyanoborohydride, is added to the solution, followed by stirring at room temperature for 4 to 48 hours. The reaction mixture is concentrated, water is added thereto, the mixture is extracted with an appropriate organic solvent. The extract is dried and concentrated, and the residue is purified by a proper method to give amino compound (29).

The preparation of monourea compound (30) containing thioacetal in the 1-substituent can preferably be carried out as follows. Acetal compound (26) prepared by the process shown in Reaction Route 4 or 5 is dissolved in an inert solvent, such as dry tetrahydrofuran, acetonitrile or dichloromethane, preferably dichloromethane. A mercaptan in an amount of 2 mol per mol of (26) or in excess over (26) and 2 equivalents, with reference to acetal (26), of an appropriate Lewis acid, such as boron trifluoride ethyl etherate, are added to the solution at room temperature or a low temperature, followed by stirring at room temperature for 10 minutes to 2 hours. The reaction mixture is concentrated, an appropriate base, such as 1N sodium hydroxide, is added thereto, and the mixture is extracted with an appropriate organic solvent. The extract is dried and concentrated under reduced pressure, and the residue is purified by a proper method to give (30).

Each enantiomer of monourea compound (19) can be prepared by stereospecifically bonding an optically active acetic ester to racemic ureido intermediate (23) to give (31), which is recrystallized to give a single diastereomer, hydrolyzing the diastereomer, and converting the resulting carboxylic acid to an amide as shown in Reaction Route 7. The single diastereomer of (31) can also be obtained by once preparing a diastereomer mixture of (31) by nonselective addition of an optically active acetic ester to racemic ureido intermediate (23) or by esterification of racemic carboxylic acid intermediate (18) and then resolving the mixture by recrystallization from an appropriate solvent.

The preparation of each enantiomer of monourea compound (19) by Reaction Route 7 can preferably be carried out as follows. Ureido intermediate (23) is dissolved in a solvent giving no adverse influence to the reaction, preferably dry tetrahydrofuran or dry dioxane, under a nitrogen atmosphere, and an equivalent, with reference to (23), of a lithium agent, such as an alkyl lithium, lithium amide or a lithium alkoxide, is added thereto at a low temperature, followed by stirring at a low temperature for 1 to 30 minutes. Additionally, an equivalent, with reference to (23), of an optically active bromoacetic ester, preferably L- or D-menthyl bromoacetate is added thereto at a low temperature, followed by stirring at −10° C. to room temperature for 4 to 24 hours. Water is added to the reaction mixture, and the mixture is extracted with an appropriate organic solvent. The extract is dried and concentrated, and the residue is recrystallized 1 to 5 times from an appropriate solvent, such as ethyl ether, isopropyl ether, hexane, an alcohol, water or a mixture thereof, to give a single diastereomer of (31). The optical purity of (31) can be analyzed by high performance liquid chromatography, high resolution nuclear magnetic resonance spectrum, and the like. Subsequently, the single diastereomer of (31) is hydrolyzed in the same manner as in the preparation of carboxylic acid (17) in Reaction Route 4 to obtain optically active intermediate (18) common to both reaction routes, which is then led to optically active monourea compound (19) in the same manner as in Reaction Route 4.

The present invention will now be illustrated in greater detail by way of Examples, but it should be understood that the present invention is not deemed to be limited thereto.

REFERENCE EXAMPLE 1

3,3-Dimethoxyindolin-2-one

In 500 ml of methanol were dissolved 14.7 g of isatin and 10.6 g of trimethyl orthoformate, and 100 mg of p-toluenesulfonic acid was added thereto. The mixture was heated under reflux for 7 hours, followed by concentration. To the residue was added chloroform, and the mixture was washed with saturated aqueous sodium hydrogencarbonate. The organic layer was dried over anhydrous sodium sulfate and concentrated. The resulting crude product was purified by silica gel column chromatography (eluent: chloroform/ethyl acetate=10/1) to give 14.7 g (76%) of the title compound as an oil.

Rf=0.38 (chloroform/methanol=20/1)
IR (CCl$_4$): 1735, 1629, 1475 cm$^{-1}$
NMR (CDCl$_3$) δ: 8.16 (br, 1H), 7.42–7.26 (m,2H), 7.07 (ddd, J=1.0, 7.3, 7.8 Hz, 1H), 6.88 (d, J=7.8 Hz, 1H), 3.58 (s, 6H).
MS (m/e): 193 (M$^+$), 165, 162, 120, 92

REFERENCE EXAMPLE 2

3,3-Diethoxyindolin-2-one

In 500 ml of ethanol were dissolved 14.7 g of isatin and 10.6 g of triethyl orthoformate, and 100 mg of camphorsulfonic acid was added thereto. The mixture was heated under reflux for 12 hours, followed by concentration. To the residue was added chloroform, and the mixture was washed with saturated aqueous sodium hydrogencarbonate. The organic layer was dried over anhydrous sodium sulfate and concentrated. The resulting crude product was purified by silica gel column chromatography (chloroform/ethyl acetate=10/1) to give 20.4 g (92%) of the title compound as an oil.

Rf=0.50 (chloroform/methanol=20/1)
NMR (CDCl$_3$) δ: 8.40 (br, 1H), 7.46–6.81 (m, 4H), 4.09–3.53 (m, 4H), 1.26 (t, J=7 Hz, 6H).

REFERENCE EXAMPLE 3

N-Benzylisatin

A solution of 44 g of isatin in 200 ml of N,N-dimethylformamide was added dropwise to a suspension of 16.0 g of sodium hydride (60%) in 100 ml of N,N-dimethylformamide at 0° C. in a nitrogen stream. After the mixture was stirred at that temperature for 30 minutes, a solution of 61.5 g of benzyl bromide in 100 ml of N,N-dimethylformamide was added thereto. The whole mixture was stirred for 1 hour and then concentrated. Chloroform was added to the residue, and the mixture was washed with saturated aqueous sodium hydrogencarbonate. The organic layer was dried over anhydrous sodium sulfate and concentrated. The resulting crude product was washed with hexane and recrystallized from ethanol to give 47.3 g (67%) of the title compound as red needles.

Rf=0.22 (n-hexane/ethyl acetate=5/1)
NMR (CDCl$_3$) δ: 7.59–8.27 (m, 7H), 7.11–7.04 (m, 1H), 6.75 (d, J=7.8 Hz, 1H), 5.93 (s, 2H).

REFERENCE EXAMPLE 4

1-Benzyl-3,3-dimethoxyindolin-2-one

The title compound was obtained in the same manner as in Reference Example 1, except for starting with N-benzylisatin.

Rf=0.33 (n-hexane/ethyl acetate=5/1).
NMR (CDCl$_3$) δ: 7.41 (d, J=6.8 Hz, 1H), 7.28–7.19 (m, 6H), 7.04 (t, J=7.8 Hz, 1H), 6.70 (d, J=7.8 Hz, 1H), 4.86 (s, 2H), 3.60 (s, 6H).
MS (m/e): 283 (M$^+$), 252, 210, 192, 132, 91

REFERENCE EXAMPLE 5

3,3-Dimethoxy-5-nitroindolin-2-one

The title compound was obtained in the same manner as in Reference Example 1, except for starting with 5-nitroisatin.

Rf=0.32 (chloroform/methanol=20/1)
NMR (CDCl$_3$) δ: 8.32 (s, 1H), 7.36–7.26 (m, 2H), 7.01 (d, J=9.2 Hz, 1H), 3.62 (s, 6H).
MS (m/e): 238 (M$^+$), 210, 180, 165

REFERENCE EXAMPLE 6

3,3-Dimethoxy-1-phenylindolin-2-one

The title compound was obtained in the same manner as in Reference Example 1, except for starting with N-phenylisatin.

Rf=0.38 (n-hexane/ethyl acetate=5/1)
NMR (CDCl$_3$) δ: 7.60–6.72 (m, 9H), 3.64 (s, 6H).
MS (m/e): 269 (M$^+$), 241, 208, 195, 180, 166

REFERENCE EXAMPLE 7

1-Allyl-3,3-dimethoxyindolin-2-one

A solution of 3.86 g of 3,3-dimethoxyindolin-2-one in 30 ml of N,N-dimethylformamide was added dropwise to a suspension of 1.2 g of sodium hydride (60%) in 40 ml of N,N-dimethylformamide at 0° C. in a nitrogen stream. After the mixture was stirred at that temperature for 30 minutes, 2.60 ml of allyl bromide was added thereto. The resulting mixture was stirred for 1 hour and then concentrated. Chloroform was added to the residue, and the mixture was washed with an aqueous solution of sodium chloride. The organic layer was dried over anhydrous sodium sulfate and concentrated. The resulting crude product was purified by silica gel column chromatography (chloroform/hexane=1/1) to give 4.19 g (90%) of the title compound.

Rf=0.85 (chloroform/methanol=20/1)
NMR (CDCl$_3$) δ: 7.52–6.71 (m, 4H), 6.20–5.55 (m, 1H), 5.41–5.00 (m, 2H), 4.30 (d, J=5 Hz, 2H), 3.57 (s, 6H).

REFERENCE EXAMPLE 8

3,3-Dimethoxy-1-(2,2-dimethoxyethyl)indolin-2-one

A solution of 34.3 g of 3,3-dimethoxyindolin-2-one in 400 ml of N,N-dimethylformamide was added dropwise to a suspension of 8.56 g of sodium hydride (60%) in 100 ml of N,N-dimethylformamide at 0° C. in a nitrogen stream. After the mixture was stirred at that temperature for 30 minutes, 36.2 g of bromoacetaldehyde dimethyl acetal was added thereto. The resulting mixture was stirred at 80° C. for 1 day and then concentrated. Ethyl acetate was added to the residue, and the mixture was washed with an aqueous solution of sodium chloride. The organic layer was dried over anhydrous sodium sulfate and concentrated. The resulting crude product was recrystallized from isopropyl alcohol/hexane to give 25.1 g (50%) of the title compound.

Rf=0.43 (n-hexane/ethyl acetate=2/1)
NMR (CDCl$_3$) δ: 7.51–6.90 (m, 4H), 4.59 (t, J=5.5 Hz, 1H), 3.77 (d, J=5.5 Hz, 2H), 3.55 (s, 6H), 3.40 (s, 6H).

REFERENCE EXAMPLE 9

1-(2,2-Diethoxyethyl)-3,3-dimethoxyindolin-2-one

The title compound was obtained in the same manner as in Reference Example 8, except for using bromoacetaldehyde diethyl acetal as a reactant.

Rf=0.71 (chloroform/methanol=20/1)
NMR (CDCl$_3$) δ: 7.48–6.70 (m, 4H), 4.66 (t, J=5 Hz, 1H), 3.78–3.28 (m, 6H), 3.52 (s, 6H), 1.12 (t, J=7 Hz, 6H).
MS (m/e): 309 (M$^+$), 232, 178, 132, 103

REFERENCE EXAMPLE 10

3,3-Diethoxy-1-(2,2-diethoxyethyl)indolin-2-one

The title compound was obtained in the same manner as in Reference Example 8, except for using 3,3-diethoxyindolin-2-one as a starting material and bromoacetaldehyde diethyl acetal as a reactant.

NMR (CDCl$_3$) δ: 7.39–7.26 (m, 2H), 7.09–7.01 (m, 2H), 4.71 (t, J=5.4 Hz, 1H), 3.95–3.67 (m, 8H), 3.57–3.43 (m, 2H), 1.22 (t, J=7.4 Hz, 6H), 1.12 (t, J=7.4 Hz, 6H).

REFERENCE EXAMPLE 11

3,3-Di-n-propoxy-1-(2,2-di-n-propoxyethyl)indolin-2-one

To a solution of 7.18 g of 3,3-dimethoxy-1-(2,2-dimethoxyethyl)indolin-2-one in 200 ml of n-propanol was added 0.1 g of camphorsulfonic acid, and the mixture was heat-refluxed for 4 days. The reaction mixture was concentrated, dichloromethane was added to the residue, and the mixture was washed with saturated aqueous sodium hydrogencarbonate. The organic layer was dried over anhydrous sodium sulfate and concentrated. The residue was purified by silica gel column chromatography (hexane/ethyl acetate=10/1) to yield 9.35 g (93%) of the title compound as a colorless oil.

NMR (CDCl$_3$) δ: 7.45–6.85 (m, 4H), 4.67 (t, J=5 Hz, 1H), 3.85–3.18 (m, 10H), 1.82–1.16 (m, 8H), 1.10–0.67 (m, 12H).

MS (m/e): 393 (M$^+$), 334, 232, 162, 131, 89

Example 1

1-Benzyl-3,3-bis(N'-(4-methylphenyl)ureido)indolin-2-one

To a solution of 0.80 g of anhydrous aluminum chloride in 20 ml of dry tetrahydrofuran were added successively a solution of 0.57 g of 1-benzyl-3,3-dimethoxyindolin-2-one in 10 ml of dry tetrahydrofuran and 0.60 g of p-tolylurea at 0° C. under a nitrogen atmosphere, and the mixture was heated under reflux for 2 hours. Ethyl acetate was added to the reaction mixture, and the mixture was washed twice with an aqueous solution of sodium chloride. The organic layer was dried over anhydrous sodium sulfate, followed by concentration. The residue was purified by silica gel column chromatography (chloroform/ethyl acetate=4/1) to obtain 0.24 g (23%) of 1-benzyl-3,3-bis(N'-(4-methylphenyl)ureido)indolin-2-one as a white powder.

Rf=0.49 (chloroform/methanol=20/1)

NMR (DMSO-d$_6$) δ: 8.71 (s, 2H), 7.82 (d, J=7.8 Hz, 1H), 7.44–7.13 (m, 17H), 6.76 (d, J=7.8 Hz, 1H), 4.96 (s, 2H), 2.21 (s, 6H).

FAB MS: 520 (M+H)$^+$, 370, 263, 237, 147, 107

Example 2

3,3-Bis(N'-(4-methylphenyl)ureido)-5-nitroindolin-2-one

The title compound was prepared in the same manner as in Example 1, except for replacing 1-benzyl-3,3-dimethoxyindolin-2-one used in Example 1 as a starting material with 3,3-dimethoxy-5-nitroindolin-2-one.

NMR (DMSO-d$_6$) δ: 11.32 (br, 1H), 8.69 (s, 2H), 8.64 (d, J=2.4 Hz, 1H), 8.18 (dd, J=2.4, 8.8 Hz, 1H), 7.38 (s, 2H), 7.29–6.99 (m, 9H), 2.21 (s, 6H).

EXAMPLES 3 TO 7

The following compounds were prepared in the same manner as in Example 1, except for replacing 1-benzyl-3,3-dimethoxyindolin-2-one used in Example 1 as a starting material with 3,3-dimethoxyindolin-2-one having a different substituent at the 1-position thereof.

Example 3

1-Allyl-3,3-bis(N'-(4-methylphenyl)ureido)indolin-2-one

NMR (DMSO-d$_6$) δ: 8.70 (s, 2H), 7.83 (d, J=6.8 Hz, 1H), 7.27–6.89 (m, 13H), 5.90–5.81 (m, 1H), 5.38 (d, J=16.1 Hz, 1H), 5.20 (d, J=8.8 Hz, 1H), 4.37 (br, 2H), 2.21 (s, 6H).

Example 4

3,3-Bis(N'-(4-methylphenyl)ureido)-1-phenylindolin-2-one

Rf=0.37 (CHCl$_3$/AcOEt=5/1)

NMR (DMSO-d$_6$) δ: 8.74 (s, 2H), 7.91 (d, J=6.3 Hz, 1H), 7.65–7.01 (m, 17H), 6.68 (d, J=7.8 Hz, 1H), 2.21 (s, 6H).

Example 5

1-(2,2-Dimethoxyethyl)-3,3-bis(N'-(4-methylphenyl)ureido)indolin-2-one

NMR (DMSO-d$_6$) δ: 8.72 (s, 2H), 7.84 (d, J=7.3 Hz, 1H), 7.26–6.98 (m, 13H), 4.63 (t, J=4.9 Hz, 1H), 3.81 (d, J=4.9 Hz, 2H), 3.36 (s, 6H), 2.20 (s, 6H).

Example 6

3,3-Bis(N'-(4-methylphenyl)ureido)-1-(2,2-di-n-propoxyethyl)indolin-2-one

Rf=0.29 (CHCl$_3$/MeOH=20/1)

NMR (CDCl$_3$) δ: 7.82 (br, 2H), 7.63 (d, J=7.3 Hz, 1H), 7.26 (t, J=4.4 Hz, 1H), 7.11 (d, J=8.3 Hz, 4H), 7.03–6.91 (m, 2H), 6.89 (d, J=8.3 Hz, 4H), 6.68 (br, 2H), 4.76 (t, J=5.4 Hz, 1H), 3.85 (d, J=5.4 Hz, 2H), 3.69–3.42 (m, 4H), 2.20 (s, 6H), 1.52 (q, J=7.3 Hz, 4H), 0.82 (t, J=7.3 Hz, 6H).

Example 7

(RS)-1-(2-Ethoxy-2-methoxyethyl)-3,3-bis(N'-(4-methylphenyl)ureido)indolin-2-one NMR (CDCl$_3$) δ: 7.79 (br, 2H), 7.76 (d, J=8.2 Hz, 1H), 7.26–6.82 (m, 13H), 4.77 (t, J=5.6 Hz, 1H), 3.87–3.53 (m, 4H), 3.41 (s, 3H), 2.16 (s, 6H), 1.13 (t, J=7.1 Hz, 3H).

Example 8

3,3-Bis(N'-(4-methylphenyl)ureido)indolin-2-one

To a solution of 12.0 g of anhydrous aluminum chloride in 150 ml of dry tetrahydrofuran were added successively a solution of 5.79 g of isatin-3,3-dimethylacetal in 150 ml of dry tetrahydrofuran and 9.0 g of p-tolylurea at 0° C. under a nitrogen atmosphere, and the mixture was heated under reflux for 40 minutes. Ethyl acetate was added to the reaction mixture, and the mixture was washed twice with an aqueous solution of sodium chloride. The organic layer was dried over anhydrous sodium sulfate, followed by concentration. To the residue was added 150 ml of ethyl ether, and insoluble matter was removed by filtration. The filtrate was concentrated and recrystallized from acetone to yield 4.61 g (36%) of the title compound as a white powder.

Rf=0.38 (chloroform/ethyl acetate=1/2)

NMR (DMSO-d$_6$) δ: 10.57 (s, 1H), 8.68 (s, 2H), 7.77 (d, J=7.8 Hz, 1H), 7.21–7.14 (m, 7H), 7.02–6.79 (m, 6H), 2.21 (s, 6H).

FAB MS: 430 (M+H)$^+$, 280, 147

IR (KBr): 3350, 1730, 1675, 1652, 1607, 1548, 1515, 1314, 1242 cm$^{-1}$

Example 9

3,3-Bis(N'-phenylureido)indolin-2-one

The title compound was prepared in the same manner as in Example 8, except for starting with phenylurea in place of p-tolylurea used in Example 8. Yield: 28%.

Rf=0.31 (chloroform/ethyl acetate=1/2)

NMR (DMSO-d$_6$) δ: 10.61 (s, 1H), 8.80 (s, 2H), 7.78 (d, J=7.8 Hz, 1H), 7.33–7.16 (m, 11H), 6.94–6.79 (m, 4H).

Example 10

1-(2,2-Diethoxyethyl)-3,3-bis(N'-(4-methylphenyl)ureido)indolin-2-one

To a solution of 4.00 g of anhydrous aluminum chloride in 30 ml of dry tetrahydrofuran were added successively a solution of 3.37 g of N-(2,2-diethoxyethyl)isatin-3,3-diethylacetal in 30 ml of dry tetrahydrofuran and 3.01 g of p-tolylurea at 0° C. in a nitrogen stream, and the mixture was heated under reflux for 2 hours. Ethyl acetate was added to the reaction mixture, and the mixture was washed twice with an aqueous solution of sodium chloride. The organic layer was dried over anhydrous sodium sulfate, followed by concentration. The residue was chromatographed on silica gel (chloroform/methanol=50/1) and recrystallized from ethyl ether to afford 0.744 g (14%) of the title compound as a white powder.

Rf=0.44 (chloroform/methanol=20/1)

NMR (CDCl$_3$) δ: 7.79 (br, 2H), 7.76 (d, J=8.2 Hz, 1H), 7.26–6.82 (m, 13H), 4.77 (t, J=4.9 Hz, 1H), 3.82–3.57 (m, 6H), 2.16 (s, 6H), 1.13 (t, J=7.1 Hz, 6H).

EXAMPLES 11 TO 21

The following compounds were prepared in the same manner as in Example 10, except for replacing p-tolylurea used in Example 10 with various arylureas.

Example 11

1-(2,2-Diethoxyethyl)-3,3-bis(N'-(4-methoxyphenyl)ureido)indolin-2-one

Rf=0.33 (CHCl$_3$/MeOH=20/1)

NMR (CDCl$_3$) δ: 7.73 (br, 2H), 7.70 (d, J=7.3 Hz, 1H), 7.28 (t, J=7.8 Hz, 1H), 7.12 (d, J=9.2 Hz, 4H), 7.08–6.96 (m, 2H), 6.67 (br, 2H), 6.64 (d, J=9.2 Hz, 4H), 4.77 (t, J=4.8 Hz, 1H), 3.86 (d, J=4.8 Hz, 2H), 3.81–3.49 (m, 4H), 3.68 (s, 6H), 1.12 (t, J=7.3 Hz, 6H).

Example 12

1-(2,2-Diethoxyethyl)-3,3-bis(N'-(4-methoxycarbonylphenyl)ureido)indolin-2-one

Rf=0.15 (CHCl$_3$/MeOH=20/1)

NMR (CDCl$_3$) δ: 8.17 (s, 2H), 7.83 (d, J=7.8 Hz, 1H), 7.63 (d, J=8.3 Hz, 4H), 7.33–7.17 (m, 7H), 7.10–6.97 (m, 2H), 4.84 (t, J=4.9 Hz, 1H), 3.81 (s, 6H), 3.85–3.60 (m, 6H), 1.16 (t, J=6.8 Hz, 6H).

Example 13

3,3-Bis(N'-(4-cyanophenyl)ureido)-1-(2,2-diethoxyethyl)indolin-2-one

Rf=0.16 (CHCl$_3$/MeOH=20/1)

NMR (DMSO-d$_6$) δ: 9.30 (s, 2H), 7.84 (d, J=7.4 Hz, 1H), 7.67–7.46 (m, 10H), 7.29 (t, J=7.4 Hz, 1H), 7.12 (d, J=7.8 Hz, 1H), 7.01 (t, J=7.8 Hz, 1H), 4.73 (t, J=5.4 Hz, 1H), 3.80 (d, J=5.4 Hz, 2H), 3.73–3.49 (m, 4H), 1.08 (t, J=7.4 Hz, 6H).

Example 14

1-(2,2-Diethoxyethyl)-3,3-bis(N'-(4-fluorophenyl)ureido)indolin-2-one

Rf=0.22 (CHCl$_3$/MeOH=20/1)

NMR (CDCl$_3$) δ: 7.88 (s, 2H), 7.79 (d, J=6.8 Hz, 1H), 7.31 (t, J=6.8 Hz, 1H), 7.17–6.97 (m, 8H), 6.75 (t, J=8.8 Hz, 4H), 4.79 (t, J=5.3 Hz, 1H), 3.85 (d, J=5.3 Hz, 2H), 3.79–3.56 (m, 4H), 1.13 (t, J=7.8 Hz, 6H).

Example 15

1-(2,2-Diethoxyethyl)-3,3-Bis(N'-(3-fluorophenyl)ureido)indolin-2-one

Rf=0.27 (CHCl$_3$/MeOH=20/1)

NMR (CDCl$_3$) δ: 8.01 (s, 2H), 7.82 (d, J=7.3 Hz, 1H), 7.35–6.90 (m, 10H), 6.82 (d, J=7.3 Hz, 1H), 6.57 (t, J=7.3 Hz, 2H), 4.82 (t, J=4.8 Hz, 1H), 3.88 (d, J=4.8 Hz, 2H), 3.83–3.60 (m, 4H), 1.15 (t, J=6.8 Hz, 6H).

Example 16

1-(2,2-Diethoxyethyl)-3,3-bis(N'-(4-nitrophenyl)ureido)indolin-2-one

Rf=0.21 (CHCl$_3$/MeOH=20/1)

NMR (CDCl$_3$-DMSO-d$_6$) δ: 9.24 (s, 2H), 8.07 (d, J=9.5 Hz, 4H), 7.95 (d, J=6.3 Hz, 1H), 7.50 (d, J=9.5 Hz, 4H), 7.45 (s, 2H), 7.30 (t, J=7.8 Hz, 1H), 7.12–7.02 (m, 2H), 4.82 (t, J=5.4 Hz, 1H), 3.91 (d, J=5.4 Hz, 2H), 3.81–3.65 (m, 4H), 1.17 (t, J=6.8 Hz, 6H).

Example 17

1-(2,2-Diethoxyethyl)-3,3-bis(N'-(4-trifluoromethylphenyl)ureido)indolin-2-one

Rf=0.29 (CHCl$_3$/MeOH=20/1)

NMR (CDCl$_3$) δ: 8.03 (br, 2H), 7.86 (d, J=7.8 Hz, 1H), 7.46–6.95 (m, 13H), 4.84 (t, J=5.4 Hz, 1H), 3.90–3.61 (m, 6H), 1.27–1.12 (m, 6H).

Example 18

1-(2,2-Diethoxyethyl)-3,3-bis(N'-(2-fluorophenyl)ureido)indolin-2-one

Rf=0.35 (n-hexane/ethyl acetate=2/1)

NMR (CDCl$_3$) δ: 7.89–7.82 (m, 3H), 7.71 (s, 2H), 7.28 (t, J=6.1 Hz, 1H), 7.18 (br, 2H), 7.10–6.98 (m, 2H), 6.89–6.78 (m, 6H), 4.82 (t, J=5.3 Hz, 1H), 3.91 (d, J=5.3 Hz, 2H), 3.82–3.71 (m, 2H), 3.67–3.58 (m, 2H), 1.13 (t, J=6.9 Hz, 6H).

Example 19

3,3-Bis(N'-(2-cyanophenyl)ureido)-1-(2,2-diethoxyethyl)indolin-2-one

Rf=0.25 (n-hexane/ethyl acetate=2/1)

NMR (CDCl$_3$-DMSO-d$_6$) δ: 8.79 (s, 2H), 8.30 (s, 2H), 8.17 (d, J=8.3 Hz, 2H), 7.98 (d, J=5.6 Hz, 1H), 7.49–7.38 (m, 4H), 7.27 (dt, J=1.3, 6.3 Hz, 1H), 7.09–6.95 (m, 4H), 4.79 (t, J=5.3 Hz, 1H), 3.89 (d, J=5.3 Hz, 2H), 3.79–3.73 (m, 2H), 3.63–3.53 (m, 2H), 1.17 (t, J=6.9 Hz, 6H).

Example 20

3,3-Bis(N'-(4-bromophenyl)ureido)-1-(2,2-diethoxyethyl)indolin-2-one

Rf=0.48 (CHCl$_3$/MeOH=20/1)

NMR (CDCl$_3$-DMSO-d$^6$) δ: 8.65 (s, 2H), 7.84 (d, J=7.3 Hz, 1H), 7.30–7.25 (m, 10H), 7.10–6.96 (m, 3H), 4.79 (t, J=5.3 Hz, 1H), 3.88 (d, J=5.3 Hz, 2H), 3.81–3.48 (m, 4H), 1.17–1.12 (m, 6H).

Example 21

3,3-Bis(N'-(3-bromophenyl)ureido)-1-(2,2-diethoxyethyl)indolin-2-one

Rf=0.48 (CHCl$_3$/MeOH=20/1)

NMR (CDCl$_3$) δ: 7.99 (br, 2H), 7.82 (d, J=7.6 Hz, 1H), 7.57 (s, 2H), 7.33–7.24 (m, 3H), 7.09–6.93 (m, 6H), 6.96–6.80 (m, 2H), 4.86 (t, J=5.0 Hz, 1H), 3.88 (d, J=5.0 Hz, 2H), 3.84–3.62 (m, 4H), 1.19–1.12 (m, 6H).

REFERENCE EXAMPLE 12

3,3-Bis(ethoxycarbonylmethyl)indolin-2-one

To a solution of 1.33 g of oxindole in 20 ml of dry dimethyl sulfoxide was added 10 ml of a 1M solution of potassium t-butoxide in dry dimethyl sulfoxide at room temperature under a nitrogen atmosphere, followed by stirring for 10 minutes. To the resulting mixture was added dropwise 1.11 ml of ethyl bromoacetate, followed by stirring at the same temperature for 20 minutes. To the mixture was further added 10 ml of a 1M solution of potassium t-butoxide in dry dimethyl sulfoxide, followed by stirring for 10 minutes. To the mixture was added dropwise 1.11 ml of ethyl bromoacetate. The resulting mixture was stirred at the same temperature for 20 minutes. The reaction mixture was treated with a sodium chloride aqueous solution and extracted with ethyl ether. The ethyl ether layer was dried over anhydrous magnesium sulfate and concentrated. The residue was purified by silica gel column chromatography (hexane/ethyl acetate=2/1) to afford 0.79 g (26%) of the title compound.

Rf=0.22 (hexane/ethyl acetate=2/1)

NMR (CDCl$_3$) δ: 7.87 (s, 1H), 7.30–7.18 (m, 2H), 7.04–6.86 (m, 2H), 4.03–3.91 (m, 4H), 3.03 (d, J=16.1 Hz, 2H), 2.88 (d, J=16.1 Hz, 2H), 1.07 (t, J=7.3 Hz, 6H).

MS (m/e): 305 (M$^+$), 232, 186, 174, 146, 130

REFERENCE EXAMPLE 13

3,3-Bis((1,1-dimethylethoxy)carbonylmethyl)indolin-2-one

The title compound was prepared in the same manner as in Reference Example 12, except for starting with t-butyl bromoacetate in place of ethyl bromoacetate used in Reference Example 12.

Rf=0.29 (hexane/ethyl acetate=2/1)

NMR (CDCl$_3$) δ: 9.03 (br, 1H), 7.42–6.80 (m, 4H), 2.83 (s, 4H), 1.19 (s, 18H).

MS (m/e): 361 (M$^+$), 249, 204, 191, 145

REFERENCE EXAMPLE 14

3,3-Bis(hydroxycarbonylmethyl)indolin-2-one

To a solution of 0.73 g of 3,3-bis(ethoxycarbonylmethyl)indolin-2-one in 40 ml of ethanol was added a solution of 1.25 g of potassium hydroxide (85%) in 5 ml of water at room temperature, and the mixture was stirred at that temperature for 15 hours, followed by concentration. The concentrate was dissolved in water, washed with chloroform, adjusted to pH 2 with 10% hydrochloric acid, and concentrated. Ethyl acetate was added to the residue, and any insoluble matter was removed by filtration. The filtrate was concentrated and purified by LH-20 column chromatography (eluent: methanol). Yield: 86%.

Rf=0.27 (chloroform/methanol 1/1)

NMR (DMSO-d$_6$) δ: 12.14 (br, 2H), 10.35 (s, 1H), 7.27 (d, J=7.2 Hz, 1H), 7.17–7.09 (m, 1H), 6.92–6.76 (m, 2H), 2.88 (d, J=16.0 Hz, 2H), 2.64 (d, J=16.0 Hz, 2H).

Example 22

3,3-Bis((4-methylphenyl)carbamoylmethyl)indolin-2-one

To a solution of 0.25 g of 3,3-bis(hydroxycarbonylmethyl)indolin-2-one and 1.24 g of dicyclohexylcarbodiimide in 30 ml of N,N-dimethylformamide were added successively 0.92 g of 1-hydroxybenzotriazole and 0.64 g of p-toluidine at room temperature. The resulting mixture was stirred at room temperature for 12 hours and concentrated. Ethyl acetate was added to the residue, and the mixture was washed successively with dilute hydrochloric acid and saturated aqueous sodium hydrogencarbonate. The organic layer was dried over anhydrous sodium sulfate and concentrated. The crude product was applied on silica gel column chromatography (chloroform/methanol 50/1) and then recrystallized from benzene to give 0.54 g (63%) of the title compound as a white powder.

NMR (DMSO-d$_6$) δ: 10.32 (s, 1H), 9.77 (s, 2H), 7.33–6.81 (m, 12H), 3.09 (d, J=14.9 Hz, 2H), 2.72 (d, J=14.9 Hz, 2H), 2.21 (s, 6H).

MS (m/e): 427 (M$^+$), 321, 293, 172, 159, 107

Example 23

1-Benzyl-3,3-bis((4-methylphenyl)carbamoylmethyl)indolin-2-one

To a suspension of 0.05 g of sodium hydride (60%) in 5 ml of N,N-dimethylformamide was added dropwise a solution of 0.36 g of 3,3-bis((1,1-dimethylethoxy)carbonylmethyl)indolin-2-one in 5 ml of N,N-dimethylformamide at 0° C. in a nitrogen stream. After stirring the mixture at that temperature for 30 minutes, 0.12 ml of benzyl bromide was added thereto. The whole mixture was stirred for 1 hour and then concentrated. Chloroform was added to the concentrate, and the mixture was washed with an aqueous solution of sodium chloride. The organic layer was dried over anhydrous sodium sulfate and concentrated to obtain 1-benzyl-3,3-bis((1,1-dimethylethoxy)carbonylmethyl)indolin-2-one.

Rf=0.66 (hexane/ethyl acetate=2/1)

NMR (CDCl$_3$) δ: 7.35–6.50 (m, 9H), 4.89 (s, 2H), 3.04–2.78 (m, 4H), 1.17 (s, 18H).

The above-prepared 1-benzyl-3,3-bis((1,1-dimethylethoxy)carbonylmethyl)indolin-2-one was dissolved in 15 ml of ethanol, and to the solution was added a solution of 0.66 g of potassium hydroxide (85%) in 2 ml of water at room temperature. The resulting mixture was heated under reflux for 5 hours, followed by concentration. The residue was dissolved in water, washed with chloroform, and adjusted to pH 2 with 10% hydrochloric acid. The resulting product was extracted with ethyl acetate, and the organic layer was dried over anhydrous sodium sulfate and concentrated. The residue was dissolved in 10 ml of chloroform, and 0.62 g of dicyclohexylcarbodiimide, 0.46 g of 1-hydroxybenzotriazole, and 0.32 g of p-toluidine were successively added to the solution, followed by stirring at room temperature for 5 hours. The resulting precipitates were removed by filtration, and the filtrate was washed successively with dilute hydrochloric acid and saturated aqueous sodium hydrogencarbonate. The organic layer was dried over anhydrous sodium sulfate, and concentrated. The crude product was purified by silica gel column chromatography (hexane/ethyl acetate=1/1) to obtain 0.29 g (57%) of the title compound as a white powder.

Rf=0.26 (hexane/ethyl acetate=1/1)

NMR (CDCl$_3$) δ: 9.83 (s, 2H), 7.46–6.61 (m, 17H), 4.92 (s, 2H), 3.20 (d, J=15.1 Hz, 2H), 2.83 (d, J=15.1 Hz, 2H), 2.21 (s, 6H).

MS (m/e): 517 (M$^+$), 411, 383, 369, 262, 107, 91

EXAMPLES 24 TO 26

The following compounds were prepared in the same manner as in Example 23, except for replacing benzyl bromide used in Example 23 with various alkyl halides.

Example 24

1-Methyl-3,3-bis((4-methylphenyl)carbamoylmethyl)indolin-2-one

Rf=0.16 (n-hexane/ethyl acetate=1/1)

NMR (DMSO-d$_6$) δ: 9.77 (s, 2H), 7.31–6.88 (m, 12H), 3.16 (s, 3H), 3.11 (d, J=15.1 Hz, 2H), 2.74 (d, J=15.1 Hz, 2H), 2.21 (s, 6H).

MS (m/e): 441 (M$^+$), 335, 307, 186, 107

Example 25

3,3-Bis((4-methylphenyl)carbamoylmethyl)-1-(phenylcarbonylmethyl)indolin-2-one

Rf=0.41 (n-hexane/ethyl acetate=1/1)

NMR (DMSO-d$_6$) δ: 9.91 (s, 2H), 8.14 (d, J=7.3 Hz, 2H), 7.73–6.86 (m, 15H), 5.35 (s, 2H), 3.30 (d, J=16.1 Hz, 2H), 2.78 (d, J=16.1 Hz, 2H), 2.22 (s, 6H).

MS (m/e): 545 (M$^+$), 439, 411, 333, 290, 107

Example 26

3,3-Bis((4-methylphenyl)carbamoylmethyl)-1-(2-pyridylmethyl)indolin-2-one

NMR (DMSO-d$_6$) δ: 9.83 (s, 2H), 8.55 (d, J=4.9 Hz, 1H), 7.66–7.50 (m, 2H), 7.38–7.01 (m, 11H), 6.89 (t, J=7.3 Hz, 1H), 6.68 (d, J=7.8 Hz, 1H), 4.98 (s, 2H), 3.20 (d, J=15.1 Hz, 2H), 2.84 (d, J=15.1 Hz, 2H), 2.21 (s, 6H).

MS (m/e): 518 (M$^+$), 412, 384, 237, 107, 92

REFERENCE EXAMPLE 15

(RS)-1-Benzyl-3-(ethoxycarbonylmethyl)-3-hydroxyindolin-2-one

To a solution of 2.4 ml of 1,1,1,3,3,3-hexamethyldisilazane in 10 ml of dry tetrahydrofuran was added dropwise 6.4 ml of a 1.59M hexane solution of n-butyl lithium at −78° C. under a nitrogen atmosphere, followed by stirring at that temperature for 10 minutes. To the mixture was slowly added 0.976 ml of ethyl acetate, followed by stirring at −78° C. for 30 minutes. To the mixture was further added a solution of 2.00 g of 1-benzylisatin in 10 ml of dry tetrahydrofuran, followed by stirring at that temperature for 1 hour. Water was added to the reaction mixture, and the product was extracted with ethyl acetate. The organic layer was dried over anhydrous sodium sulfate to give 2.23 g (81%) of the title compound.

NMR (CDCl$_3$) δ: 7.45–6.55 (m, 9H), 4.84 (s, 2H), 4.12 (q, J=6.9 Hz, 2H), 2.97 (s, 2H), 1.40 (br, 1H), 1.13 (t, J=6.9 Hz, 3H).

REFERENCE EXAMPLE 16

(RS)-1-Benzyl-3-hydroxy-3-((4-methylphenyl)aminocarbonylmethyl)indolin-2-one

To a solution of 0.254 g of p-toluidine in 10 ml of dry tetrahydrofuran was added dropwise 1.3 ml of a 1.59M hexane solution of n-butyl lithium at −78° C. under a nitrogen atmosphere, followed by stirring at that temperature for 10 minutes. To the mixture was added a solution of 0.299 g of 1-benzyl-3-(ethoxycarbonylmethyl)-3-hydroxyindolin-2-one in 5 ml of dry tetrahydrofuran at −78° C., followed by stirring at that temperature for 30 minutes. Water was added to the reaction mixture, and the product was extracted with chloroform. The organic layer was dried over anhydrous sodium sulfate and concentrated. The residue was purified by silica gel column chromatography (hexane/ethyl acetate=5/1) to give 0.161 g (44%) of the title compound.

NMR (CDCl$_3$) δ: 8.38 (s, 1H), 7.47–6.92 (m, 12H), 6.67 (d, J=8.6 Hz, 1H), 5.38 (s, 1H), 4.88 (d, J=16.0 Hz, 1H), 4.74 (d, J=16.0 Hz, 1H), 3.06 (d, J=14.9 Hz, 1H), 2.69 (d, J=14.9 Hz, 1H), 2.29 (s, 3H).

Example 27

(RS)-1-Benzyl-3-((4-methylphenyl)aminocarbonylmethyl)-3-((4-methylphenyl)aminocarbonyloxa)indolin-2-one To a solution of 0.155 g of 1-benzyl-3-hydroxy-3-((4-methylphenyl)aminocarbonylmethyl)indolin-2-one and 0.097 ml of p-tolyl isocyanate in 10 ml of dry tetrahydrofuran was added 10 mg of dibutyltin diacetate at room temperature under a nitrogen atmosphere, and the mixture was stirred at that temperature for 18 hours. Water was added to the reaction mixture, and the product was extracted with dichloromethane. The organic layer was dried over anhydrous sodium sulfate and concentrated. The residue was purified by silica gel column chromatography (hexane/ethyl acetate=3/1) to give 0.178 g (89%) of the title compound.

NMR (CDCl$_3$) δ: 9.42–9.12 (br, 1H), 7.60–6.88 (m, 17H), 6.68 (d, J=7.8 Hz, 1H), 5.04 (d, J=14.8 Hz, 1H), 4.94 (d, J=14.8 Hz, 1H), 3.14 (d, J=15.2 Hz, 1H), 2.99 (d, J=15.2 Hz, 1H), 2.28 (s, 3H), 2.21 (s, 3H).

REFERENCE EXAMPLE 17

1-Benzyl-3-(hydroxyimino)indolin-2-one

To a suspension of 7.11 g of N-benzylisatin in 75 ml of ethanol was added a solution of 3.84 g of hydroxylamine hydrochloride and 3.84 g of sodium acetate in 500 ml of water. The mixture was stirred at room temperature for 1 hour, followed by concentration. The residue was washed with water and recrystallized from ethanol to give 6.11 g (81%) of the title compound as yellow crystals.

Rf=0.33 (chloroform/methanol=20/1)

NMR (DMSO-$d_6$) δ: 13.51 (br, 1H), 8.00 (d, J=7.3 Hz, 1H), 7.39–7.26 (m, 6H), 7.10–6.96 (m, 2H), 4.94 (s, 2H).

MS (m/e): 252 (M$^+$), 235, 207, 91

REFERENCE EXAMPLE 18

(RS)-3-(N'-(4-Methylphenyl)ureido)indolin-2-one

To a suspension of 73.6 g of isatin in 1.2 l of ethanol was added a solution of 64.1 g of hydroxylamine hydrochloride and 64.1 g of sodium acetate in 500 ml of water. The mixture was stirred at room temperature for 30 minutes and concentrated. The residue was washed with water and recrystallized from ethanol to give 51.8 g (64%) of 3-(hydroxyimino) indolin-2-one as yellow crystals.

Rf=0.41 (chloroform/methanol=10/1)

NMR (CDCl$_3$/DMSO-$d_6$) δ: 12.52 (s, 1H), 7.39–6.81 (m, 4H).

MS (m/e): 162 (M$^+$), 145, 117

A suspension of 4.86 g of 3-(hydroxyimino)indolin-2-one and 100 mg of 5% Rh/C in 300 ml of ethanol was stirred at room temperature under a hydrogen atmosphere for 1 day. The reaction mixture was filtered through Cerite, and the filtrate was concentrated. The concentrate was dissolved in 300 ml of dichloromethane, and 4.16 ml of p-tolyl isocyanate was added thereto at 0° C. The mixture was stirred at that temperature for 2 hours, whereupon a precipitate formed. The precipitate was collected by filtration and washed with ethanol to obtain 7.59 g (90%) of the title compound.

NMR (DMSO-$d_6$) δ: 10.30 (s, 1H), 8.61 (s, 1H), 7.27–6.77 (m, 9H), 4.95 (d, J=7.3 Hz, 1H), 2.21 (s, 3H).

MS (m/e): 281 (M$^+$), 174, 148, 132, 107

REFERENCE EXAMPLE 19

(RS)-3-((4-Methylbenzyl)carbonylamino)indolin-2-one

A solution of 4.86 g of 3-(hydroxyimino)indolin-2-one and 100 mg of 5% Rh/C in 300 ml of ethanol was stirred at room temperature under a hydrogen atmosphere for 1 day. The reaction mixture was filtered through Cerite, and the filtrate was concentrated. The concentrate was dissolved in 50 ml of N,N-dimethylformamide, and 5.15 g of dicyclohexylcarbodiimide, 3.83 g of 1-hydroxybenzotriazole, and 3.75 g of p-tolylacetic acid were added thereto successively. The mixture was stirred at the same temperature for 12 hours, whereupon a precipitate formed. The precipitate was filtered off, and the filtrate was concentrated. The concentrate was diluted with ethyl acetate and washed successively with dilute hydrochloric acid and saturated aqueous sodium hydrogencarbonate. The organic layer was dried over anhydrous sodium sulfate and concentrated. The residue was purified by silica gel column chromatography (chloroform/methanol=40/1) to afford 1.01 g (18%) of the title compound.

Rf=0.32 (chloroform/methanol=20/1)

NMR (DMSO-$d_6$) δ: 10.39 (s, 1H), 8.80 (d, J=8.3 Hz, 1H), 7.21–7.02 (m, 6H), 6.91 (dd, J=1.0, 6.3 Hz, 1H), 6.79 (d, J=6.3 Hz, 1H), 5.08 (d, J=8.3 Hz, 1H), 3.44 (s, 2H), 2.27 (s, 3H).

MS (m/e): 280 (M$^+$), 262, 148, 132, 105

REFERENCE EXAMPLE 20

(RS)-1-Benzyl-3-(methylcarbonylamino)indolin-2-one

A suspension of 2.52 g of 1-benzyl-3-(hydroxyimino) indolin-2-one and 100 mg of 5% Rh/C in 200 ml of methanol was stirred under a hydrogen atmosphere at room temperature for 1 day. The reaction mixture was filtered through Cerite, and the filtrate was concentrated. The residue was dissolved in 200 ml of dichloromethane, and 2.79 ml of triethylamine and 0.85 ml of acetyl chloride were successively added thereto at room temperature. The mixture was stirred at that temperature for 1 hour, and then was washed successively with dilute hydrochloric acid and saturated aqueous sodium hydrogencarbonate. The organic layer was dried over anhydrous sodium sulfate and concentrated. Recrystallization of the residue from chloroform-hexane gave 1.28 g (45%) of the title compound.

Rf=0.30 (chloroform/methanol=20/1)

NMR (DMSO-$d_6$) δ: 8.79 (d, J=7.8 Hz, 1H), 7.41–7.13 (m, 7H), 6.98 (dd, J=6.8, 7.8 Hz, 1H), 6.76 (d, J=7.3 Hz, 1H), 5.22 (d, J=7.8 Hz, 1H), 4.97 (d, J=15.8 Hz, 1H), 4.81 (d, J=15.8 Hz, 1H), 1.92 (s, 3H).

REFERENCE EXAMPLE 21

1-(2,2-Diethoxyethyl)isatin

A solution of 31.8 g of isatin in 300 ml of dry dimethyl sulfoxide was added dropwise to a suspension of 25.4 g of potassium t-butoxide in 200 ml of dry dimethyl sulfoxide at 10° C. in a nitrogen stream. After stirring the mixture at that temperature for 30 minutes, 39 ml of bromoacetaldehyde diethyl acetal was added thereto, followed by stirring at 70° C. for 6 hours. The reaction mixture was poured into dilute hydrochloric acid and extracted with ethyl ether. The organic layer was dried over anhydrous magnesium sulfate and concentrated. The residue was purified by silica gel column chromatography (chloroform/ethyl acetate=20/1) to give 31.4 g (55%) of the title compound as a red powder.

Rf=0.83 (chloroform/methanol=20/1)

NMR (CDCl$_3$) δ: 7.75–6.95 (m, 4H), 4.71 (t, J=5 Hz, 1H), 3.89–3.40 (m, 6H), 1.16 (t, J=7 Hz, 6H).

Example 28

(RS)-1-(2,2-Diethoxyethyl)-3-(N'-(4-methylphenyl) ureido)indolin-2-one

A solution of 5.38 g of hydroxylamine hydrochloride and 5.38 g of sodium acetate in 40 ml of water was added to a suspension of 11.1 g of 1-(2,2-diethoxyethyl)isatin in 100 ml of ethanol. The mixture was stirred at room temperature for 1 hour, followed by concentration. The concentrate was diluted with chloroform and washed with an aqueous solution of sodium chloride. The chloroform layer was dried over anhydrous sodium sulfate and concentrated, and the residue was recrystallized from ethyl acetate to obtain 7.10 g (61%) of 1-(2,2-diethoxyethyl)-3-(hydroxyimino)indolin-2-one as yellow crystals.

Rf=0.32 (chloroform/methanol=20/1)

NMR (CDC$_3$/DMSO-d$_6$) δ: 12.85 (s, 1H), 8.09 (d, J=7.8 Hz, 1H), 7.39–7.31 (m, 1H), 7.08–7.01 (m, 2H), 4.70 (t, J=5.4 Hz, 1H), 3.84 (d, J=5.4 Hz, 2H), 3.82–3.43 (m, 4H), 1.14 (t, J=6.8 Hz, 6H).

A suspension of 30.0 g of 1-(2,2-diethoxyethyl)-3-(hydroxyimino)indolin-2-one and 200 mg of 5% Rh/C in 1.5 l of ethanol was stirred under a hydrogen atmosphere at room temperature for 2 days. The reaction mixture was filtered through Cerite, and the filtrate was concentrated. The residue was dissolved in 600 ml of dichloromethane, and a solution of 15.0 ml of p-tolyl isocyanate in 200 ml of dichloromethane was added thereto at 0° C. The mixture was stirred at that temperature for 1 hour, followed by concentration. The resulting crude product was washed with ethyl ether to yield 30.8 g (72%) of the title compound as a white powder.

NMR (DMSO-d$_6$) δ: 8.63 (s, 1H), 7.33–7.16 (m, 4H), 7.12–6.87 (m, 5H), 5.05 (d, J=7.4 Hz, 1H), 4.77–4.63 (m, 1H), 3.84 (dd, J=5.7, 14.6 Hz, 1H), 3.77–3.40 (m, 5H), 2.22 (s, 3H), 1.08 (t, J=7.4 Hz, 3H), 1.06 (t, J=7.4 Hz, 3H).

EXAMPLES 29 TO 32

The following compounds were prepared in the same manner as in Example 28, except for replacing 1-(2,2-diethoxyethyl)isatin used as a starting material in Example 28 with various isatin derivatives.

Example 29

(RS)-1-Benzyl-3-(N'-(4-methylphenyl)ureido) indolin-2-one

NMR (DMSO-d$_6$) δ: 8.70 (s, 1H), 7.39–7.00 (m, 13H), 6.78 (d, J=7.3 Hz, 1H), 5.13 (d, J=7.3 Hz, 1H), 4.90 (s, 2H), 2.21 (s, 3H).

MS (m/e): 371 (M$^+$), 238, 147, 107, 91

Example 30

(RS)-3-(N'-(4-Methylphenyl)ureido)-1-phenylindolin-2-one

NMR (DMSO-d$_6$) δ: 8.76 (s, 1H), 7.61–6.99 (m, 13H), 6.71 (d, J=7.3 Hz, 1H), 5.20 (d, J=7.3 Hz, 1H), 2.22 (s, 3H).

MS (m/e): 357 (M$^+$), 250, 223, 194, 180, 106

Example 31

(RS)-1-(2,2-Diethoxyethyl)-5-methyl-3-(N'-(4-methylphenyl)ureido)indolin-2-one

NMR (DMSO-d$_6$) δ: 8.62 (s, 1H), 7.25 (d, J=8.3 Hz, 2H), 7.06–6.86 (m, 6H), 5.03 (d, J=7.8 Hz, 1H), 4.71–4.66 (m, 1H), 3.81 (dd, J=5.4, 14.2 Hz, 1H), 3.72–3.29 (m, 5H), 2.27 (s, 3H), 2.21 (s, 3H), 1.07 (t, J=6.8 Hz, 3H), 1.06 (t, J=6.8 Hz, 3H).

MS (m/e): 411 (M$^+$), 365, 232, 103

Example 32

(RS)-5-Bromo-1-(2,2-diethoxyethyl)-3-(N'-(4-methylphenyl)ureido)indolin-2-one

NMR (DMSO-d$_6$) δ: 8.74 (s, 1H), 7.48–7.15 (m, 4H), 7.10–6.88 (m, 4H), 5.03 (d, J=7.4 Hz, 1H), 4.72–4.60 (m, 1H), 3.90–3.37 (m, 6H), 2.21 (s, 3H), 1.07 (t, J=6.4 Hz, 6H).

EXAMPLES 33 TO 41

The following compounds were prepared in the same manner as in Example 28, except for replacing p-tolyl isocyanate used as a reactant in Example 28 with various isocyanates.

Example 33

(RS)-3-(N'-(4-Chlorophenyl)ureido)-1-(2,2-diethoxyethyl)indolin-2-one

NMR (DMSO-d$_6$) δ: 8.97 (s, 1H), 7.40 (d, J=9.4 Hz, 2H), 7.29–6.96 (m, 7H), 5.06 (d, J=7.3 Hz, 1H), 4.72–4.67 (m, 1H), 3.84 (dd, J=5.4, 14.1 Hz, 1H), 3.70–3.41 (m, 5H), 1.13–1.03 (m, 6H).

MS (m/e): 419, 417 (M$^+$), 374, 371, 153, 103

Example 34

(RS)-1-(2,2-Diethoxyethyl)-3-(N'-(4-methoxyphenyl)ureido)indolin-2-one

NMR (CDCl$_3$) δ: 7.37 (d, J=7.3 Hz, 1H), 7.26–7.01 (m, 6H), 6.76 (d, J=8.8 Hz, 2H), 5.80 (d, J=7.8 Hz, 1H), 5.19 (d, J=7.8 Hz, 1H), 4.70–4.65 (m, 1H), 3.91 (dd, J=5.4, 14.6 Hz, 1H), 3.74–3.43 (m, 5H), 3.70 (s, 3H), 1.65–1.12 (m, 6H).

MS (m/e): 413 (M$^+$), 367, 218, 103

Example 35

(RS)-3-(N'-Cyclohexylureido)-1-(2,2-diethoxyethyl) indolin-2-one

NMR (CDCl$_3$) δ: 7.39 (d, J=7.8 Hz, 1H), 7.27 (dd, J=7.3, 7.8 Hz, 1H), 7.08–7.01 (m, 2H), 5.18–5.05 (m, 3H), 4.71–4.65 (m, 1H), 3.92 (dd, J=5.4, 14.1 Hz, 1H), 3.80–3.42 (m, 6H), 2.02–1.88 (m, 2H), 1.78–1.51 (m, 4H), 1.48–1.02 (m, 10H).

MS (m/e): 389 (M$^+$), 343, 218, 103

Example 36

(RS)-3-(N'-(2-Chlorophenyl)ureido)-1-(2,2-diethoxyethyl)indolin-2-one

NMR (CDCl$_3$-DMSO-d$_6$) δ: 8.25 (dd, J=1.5, 6.8 Hz, 1H), 8.05 (s, 1H), 7.66 (d, J=7.3 Hz, 1H), 7.41–7.00 (m, 6H), 6.91 (dt, J=1.5, 7.8 Hz, 1H), 5.23 (d, J=7.3 Hz, 1H), 4.75–4.69 (m, 1H), 3.95 (dd, J=5.4, 14.1 Hz, 1H), 3.82–3.42 (m, 5H), 1.16 (t, J=7.3 Hz, 3H), 1.15 (t, J=6.8 Hz, 3H).

MS (m/e): 419, 417 (M$^+$), 373, 371, 103

Example 37

(RS)-1-(2,2-Diethoxyethyl)-3-(N'-(4-fluorophenyl) ureido)indolin-2-one

NMR (DMSO-d$_6$) δ: 8.81 (s, 1H), 7.42–6.95 (m, 9H), 5.07 (d, J=7.8 Hz, 1H), 4.70 (dd, J=3.4 Hz, 5.4 Hz, 1H), 3.85 (dd, J=5.4, 14.1 Hz, 1H), 3.74–3.34 (m, 5H), 1.074 (t, J=6.8 Hz, 3H), 1.067 (t, J=6.8 Hz, 3H).

MS (m/e): 401 (M$^+$), 355, 218, 202, 146, 103, 75

Example 38

(RS)-1-(2,2-Diethoxyethyl)-3-(N'-phenylureido) indolin-2-one

NMR (DMSO-d$_6$) δ: 8.78 (s, 1H), 7.39–6.86 (m, 10H), 5.07 (d, J=7.3 Hz, 1H), 4.70 (dd, J=4.9 Hz, 5.4 Hz, 1H), 3.84

(dd, J=5.4, 14.1 Hz, 1H), 3.70–3.41 (m, 5H), 1.07 (t, J=6.8 Hz, 3H), 1.06 (t, J=6.8 Hz, 3H).

MS (m/e): 383 (M⁺), 337, 202, 174, 119, 103, 75

Example 39

(RS)-1-(2,2-Diethoxyethyl)-3-(N'-(3-methoxyphenyl)ureido)indolin-2-one

NMR (CDCl₃) δ: 7.65 (s, 1H), 7.40–7.00 (m, 6H), 6.79 (d, J=9.3 Hz, 1H), 6.53 (dd, J=2.4, 8.3 Hz, 1H), 6.07 (d, J=7.8 Hz, 1H), 5.17 (d, J=7.3 Hz, 1H), 4.69 (dd, J=5.4, 5.9 Hz, 1H), 3.92 (dd, J=5.4, 14.1 Hz, 1H), 3.79–3.45 (m, 5H), 3.70 (s, 3H), 1.14 (t, J=7.3 Hz, 3H), 1.13 (t, J=7.3 Hz, 3H).

MS (m/e): 413 (M⁺), 367, 218, 202, 174, 103, 75

Example 40

(RS)-1-(2,2-Diethoxyethyl)-3-(N'-ethylureido)indolin-2-one

NMR (CDCl₃) δ: 7.40–7.01 (m, 4H), 5.26–5.16 (m, 3H), 4.68 (dd, J=5.4, 5.4 Hz, 1H), 3.91 (dd, J=5.4, 14.6 Hz, 1H), 3.77–3.65 (m, 3H), 3.56–3.45 (m, 2H), 3.30–3.17 (m, 2H), 1.15 (t, J=7.3 Hz, 3H), 1.14 (t, J=6.8 Hz, 3H), 1.13 (t, J=7.3 Hz, 3H).

MS (m/e): 335 (M⁺), 289, 218, 189, 146, 131, 117, 103, 75

Example 41

(RS)-3-(N'-(4-Ethoxycarbonylphenyl)ureido)-1-(2,2-diethoxyethyl)indolin-2-one

NMR (CDCl₃) δ: 8.07 (s, 1H), 7.77 (d, J=8.8 Hz, 2H), 7.41–7.06 (m, 6H), 6.36 (br, 1H), 5.15 (d, J=6.8 Hz, 1H), 4.73 (dd, J=4.9, 4.9 Hz, 1H), 4.31 (q, J=7.3 Hz, 2H), 3.99 (dd, J=4.9, 14.1 Hz, 1H), 3.86–3.48 (m, 5H), 1.36 (t, J=7.3 Hz, 3H), 1.15 (t, J=6.8 Hz, 3H), 1.14 (t, J=6.8 Hz, 3H).

REFERENCE EXAMPLE 22

3-(Benzyloxyimino)-7-methylindolin-2-one

To a suspension of 4.91 g of 7-methylisatin in 100 ml of ethanol was added a solution of 5.59 g of O-benzylhydroxylamine hydrochloride and 3.29 g of sodium acetate in 40 ml of water at room temperature. The mixture was stirred at room temperature for 3 hours and concentrated. The concentrate was diluted with chloroform and washed with water. The organic layer was dried over anhydrous sodium sulfate and concentrated. Recrystallization of the crude product from benzene yielded 5.40 g (68%) of the title compound.

Rf=0.46 (chloroform/methanol=10/1)

NMR (DMSO-d₆) δ: 10.81 (s, 1H), 7.69 (d, J=7.8 Hz, 1H), 7.43–7.34 (m, 5H), 7.20 (d, J=7.8 Hz, 1H), 6.93 (t, J=7.8 Hz, 1H), 5.45 (s, 2H), 2.19 (s, 3H).

MS (m/e): 266 (M⁺), 249, 131, 91

REFERENCE EXAMPLE 23

(RS)-7-Methyl-3-(N'-(4-methylphenyl)ureido)indolin-2-one

A suspension of 1.30 g of 3-(benzyloxyimino)-7-methylindolin-2-one and 50 mg of 5% Pd/C in 500 ml of methanol was stirred under a hydrogen atmosphere at room temperature for 2 days. The reaction mixture was filtered through Cerite, and the filtrate was concentrated. The residue was dissolved in 20 ml of dichloromethane, and 0.67 g of p-tolyl isocyanate was added thereto at 0° C. The mixture was stirred at that temperature for 2 hours, followed by concentration. The concentrate was washed with ethyl ether to yield 1.00 g (69%) of the title compound.

Rf=0.51 (hexane/ethyl acetate=2/1)

NMR (DMSO-d₆) δ: 10.36 (s, 1H), 8.60 (s, 1H), 7.31–6.79 (m, 8H), 4.96 (d, J=7.8 Hz, 1H), 2.21 (s, 3H), 2.20 (s, 3H).

MS (m/e): 295 (M⁺), 188, 162, 107

Example 42

(RS)-1-(2,2-Diethoxyethyl)-3-(N'-(3-methylphenyl)ureido)indolin-2-one

To a suspension of 5.0 g of isatin in 200 ml of ethanol was added a solution of 9.75 g of O-benzylhydroxylamine hydrochloride and 4.18 g of sodium acetate in 50 ml of water at room temperature. The mixture was stirred at room temperature for 3 hours and concentrated. The concentrate was diluted with ethyl acetate and then washed with water. The organic layer was dried over anhydrous sodium sulfate and concentrated. Recrystallization of the crude product from ethanol gave 6.06 g (71%) of 3-(benzyloxyimino)indolin-2-one as yellow crystals.

Rf=0.49 (dichloromethane/methanol=100/3)

NMR (CDCl₃) δ: 9.70–9.40 (br, 1H), 7.85 (d, J=7.4 Hz, 1H), 7.50–6.70 (m, 3H), 7.34 (s, 5H), 5.46 (s, 2H).

To a suspension of 0.35 g of sodium hydride (60%) in 20 ml of N,N-dimethylformamide was added dropwise a solution of 2.00 g of 3-(benzyloxyimino)indolin-2-one in 20 ml of N,N-dimethylformamide at 0° C. in a nitrogen stream. After stirring the mixture at room temperature for 1 hour, 1.40 ml of bromoacetaldehyde diethyl acetal was added thereto, and the mixture was stirred for 12 hours at 70° C. The reaction mixture was concentrated, and the residue was diluted with ethyl acetate and washed with an aqueous solution of sodium chloride. The organic layer was dried over anhydrous sodium sulfate and concentrated. The resulting crude product was purified by silica gel column chromatography (chloroform/methanol=100/1) to give 2.20 g (76%) of 3-(benzyloxyimino)-1-(2,2-diethoxyethyl)indolin-2-one.

Rf=0.27 (dichloromethane/methanol=100/1)

NMR (CDCl₃) δ: 8.00–7.80 (m, 1H), 7.60–6.80 (m, 3H), 7.38 (s, 5H), 5.51 (s, 2H), 4.71 (t, J=5.4 Hz, 1H), 4.00–3.20 (m, 6H), 1.14 (t, J=7.2 Hz, 6H).

A suspension of 2.20 g of 3-(benzyloxyimino)-1-(2,2-diethoxyethyl)indolin-2-one and 100 mg of 5% Pd/C in 50 ml of methanol was stirred under a hydrogen atmosphere at room temperature for 2 days. The reaction mixture was filtered through Cerite, and the filtrate was concentrated. The residue was dissolved in 20 ml of dichloromethane, and 0.89 ml of m-tolyl isocyanate was added thereto at 0° C. The mixture was stirred at room temperature for 2 hours, followed by concentration. The concentrate was recrystallized from ethyl ether to yield 1.13 g (47%) of the title compound.

Rf=0.14 (hexane/ethyl acetate=2/1)

NMR (CDCl₃) δ: 8.69 (s, 1H), 8.29 (s, 1H), 7.29–6.94 (m, 7H), 6.72 (d, J=6.8 Hz, 1H), 5.05 (d, J=7.8 Hz, 1H), 4.70 (dd, J=4.4, 5.4 Hz, 1H), 3.81 (dd, J=5.4, 14.1 Hz, 1H), 3.70–3.29 (m, 5H), 2.22 (s, 3H), 1.074 (t, J=6.8 Hz, 3H), 1.067 (t, J=6.8 Hz, 3H).

Example 43

(RS)-1-(2,2-Diethoxyethyl)-5-fluoro-3-(N'-(4-methylphenyl)ureido)indolin-2-one

The title compound was prepared in the same manner as in Example 42, except for using 5-fluoroisatin as a starting material in place of isatin used in Example 42.

NMR (CDCl$_3$) δ: 7.20–6.82 (m, 8H), 6.10 (d, J=6.9 Hz, 1H), 5.09 (d, J=6.9 Hz, 1H), 4,71–4.66 (m, 1H), 4.02–3.64 (m, 6H), 2.25 (s, 3H), 1.17–1.09 (m, 6H).

Example 44

(RS)-1-(2,2-Ethoxyethyl)-5-methoxy-3-(N'-(4-methylphenyl)ureido)indolin-2-one

The title compound was prepared in the same manner as in Example 42, except for using 5-methoxyisatin as a starting material in place of isatin used in Example 42.

NMR (CDCl$_3$) δ: 7.46 (br, 1H), 7.17 (d, J=8.2 Hz, 2H), 7.11–6.93 (m, 4H), 6.78 (dd, J=2.6, 8.2 Hz, 1H), 5.97 (d, J=6.9 Hz, 1H), 5.14 (d, J=6.9 Hz, 1H), 4.69–4.64 (m, 1H), 3.90 (dd, J=5.3, 14.2 Hz, 1H), 3.76 (s, 3H), 3.74–3.64 (m, 3H), 3.54–3.42 (m, 2H), 2.25 (s, 3H), 1.16–1.10 (m, 6H).

EXAMPLES 45 TO 52

The following compounds were prepared in the same manner as in Example 42, except for replacing p-tolyl isocyanate used as a reactant in Example 42 with various isocyanate compounds.

Example 45

(RS)-1-(2,2-Diethoxyethyl)-3-(N'-(2-methylphenyl)ureido)indolin-2-one

NMR (DMSO-d$_6$) δ: 7.91 (s, 1H), 7.74 (d, J=7.8 Hz, 1H), 7.37–6.84 (m, 8H), 5.12 (d, J=7.3 Hz, 1H), 4.70 (dd, J=5.4, 5.4 Hz, 1H), 3.84 (dd, J=5.4, 14.6 Hz, 1H), 3.70–3.26 (m, 5H), 2.20 (s, 3H), 1.07 (t, J=7.3 Hz, 3H), 1.06 (t, J=7.3 Hz, 3H).

Example 46

(RS)-3-(N'-(3-Chlorophenyl)ureido)-1-(2,2-diethoxyethyl)indolin-2-one

NMR (DMSO-d$_6$) δ: 9.03 (s, 1H), 7.63 (s, 1H), 7.30–6.89 (m, 8H), 5.06 (d, J=7.8 Hz, 1H), 4.70 (dd, J=3.4, 5.4 Hz, 1H), 3.86 (dd, J=5.4, 14.6 Hz, 1H), 3.71–3.30 (m, 5H), 1.09 (t, J=7.3 Hz, 3H), 1.08 (t, J=7.3 Hz, 3H).

Example 47

(RS)-1-(2,2-Diethoxyethyl)-3-(N'-(2-methoxyphenyl)ureido)indolin-2-one

NMR (DMSO-d$_6$) δ: 8.14 (s, 1H), 8.00 (d, J=7.8 Hz, 1H), 7.67 (d, J=7.8 Hz, 1H), 7.30–6.76 (m, 7H), 5.12 (d, J=7.8 Hz, 1H), 4.70 (dd, J=4.9, 5.4 Hz, 1H), 3.85 (s, 3H), 3.88–3.29 (m, 6H), 1.08 (t, J=6.8 Hz, 3H), 1.07 (t, J=6.8 Hz, 3H).

Example 48

(RS)-1-(2,2-Diethoxyethyl)-3-(N'-(4-nitrophenyl)ureido)indolin-2-one

NMR (DMSO-d$_6$) δ: 9.61 (s, 1H), 8.11 (d, J=9.3 Hz, 2H), 7.61 (d, J=9.3 Hz, 2H), 7.34–6.97 (m, 5H), 5.01 (d, J=7.3 Hz, 1H), 4.70 (dd, J=2.9, 5.4 Hz, 1H), 3.86 (dd, J=5.4, 14.1 Hz, 1H), 3.71–3.42 (m, 5H), 1.08 (t, J=7.3 Hz, 6H).

Example 49

(RS)-3-(N'-(4-Cyanophenyl)ureido)-1-(2,2-diethoxyethyl)indolin-2-one

NMR (DMSO-d$_6$) δ: 9.36 (s, 1H), 7.70–7.53 (m, 5H), 7.30–7.21 (m, 2H), 7.09–6.96 (m, 2H), 5.09 (d, 7.3 Hz, 1H), 4.70 (dd, J=3.4, 5.4 Hz, 1H), 3.86 (dd, J=5.4, 14.1 Hz, 1H), 3.71–3.41 (m, 5H), 1.08 (t, J=7.3 Hz, 3H), 1.07 (t, J=7.3 Hz, 3H).

Example 50

(RS)-1-(2,2-Diethoxyethyl)-3-(N'-(3-trifluoromethylphenyl)ureido)indolin-2-one

NMR (CDCl$_3$) δ: 8.04 (s, 1H), 7.55 (s, 1H), 7.39–7.03 (m, 7H), 6.62 (d, J=6.8 Hz, 1H), 5.06 (d, J=6.8 Hz, 1H), 4.73 (dd, J=4.9, 4.9 Hz, 1H), 3.98–3.46 (m, 6H), 1.14 (t, J=6.8 Hz, 3H), 1.13 (t, J=6.8 Hz, 3H).

Example 51

(RS)-1-(2,2-Diethoxyethyl)-3-(N'-(3-fluorophenyl)ureido)indolin-2-one

NMR (DMSO-d$_6$) δ: 9.05 (s, 1H), 7.42–6.96 (m, 8H), 6.68 (dt, J=2.4, 8.3 Hz, 1H), 5.07 (d, J=7.8 Hz, 1H), 4.70 (dd, J=4.9, 5.4 Hz, 1H), 3.85 (dd, J=5.4, 14.1 Hz, 1H), 3.70–3.30 (m, 5H), 1.08 (t, J=7.3 Hz, 3H), 1.06 (t, J=7.3 Hz, 3H).

Example 52

(RS)-1-(2,2-Diethoxyethyl)-3-(N'-(4-trifluoromethylphenyl)ureido)indolin-2-one

Rf=0.28 (n-hexane/ethyl acetate=1/1)

NMR (DMSO-d$_6$) δ: 9.26 (s, 1H), 7.61–6.97 (m, 9H), 5.09 (d, J=7.8 Hz, 1H), 4.70 (dd, J=4.9, 5.4 Hz, 1H), 3.86 (dd, J=5.4, 14.1 Hz, 1H), 3.74–3.42 (m, 5H), 1.07 (t, J=7.3 Hz, 6H).

Example 53

(RS)-1,3-Bis(ethoxycarbonylmethyl)-3-(N'-(4-methylphenyl)ureido)indolin-2-one (53a) and (RS)-3-(Ethoxycarbonylmethyl)-3-(N'-(4-methylphenyl)ureido)indolin-2-one (53b)

To a solution of 2.81 g of (RS)-3-(N'-(4-methylphenyl)ureido)indolin-2-one in 80 ml of dry dimethyl sulfoxide was added 10 ml of a 1M solution of potassium t-butoxide in dry dimethyl sulfoxide at room temperature under a nitrogen atmosphere. After stirring for 1 hour, 1.11 ml of ethyl bromoacetate was dropwise added thereto, followed by stirring at the same temperature for 1 hour. The reaction mixture was treated with an aqueous solution of sodium chloride and extracted with ethyl ether. The ethyl ether layer was dried over anhydrous magnesium sulfate, and concentrated. The concentrate was purified by silica gel column chromatography (chloroform/methanol=40/1) to give 0.68 g (15%) of (RS)-1,3-bis(ethoxycarbonylmethyl)-3-(N'-(4-methylphenyl)ureido)indolin-2-one:

Rf=0.57 (chloroform/methanol=20/1)

NMR (DMSO-d$_6$) δ: 8.97 (s, 1H), 7.24–6.94 (m, 9H), 4.59 (d, J=16.1 Hz, 1H), 4.51 (d, J=16.1 Hz, 1H), 4.17–4.00 (m, 4H), 2.89 (d, J=15.1 Hz, 1H), 2.53 (d, J=15.1 Hz, 1H), 2.18 (s, 3H), 1.22 (t, J=6.8 Hz, 3H), 1.11 (t, J=7.3 Hz, 3H).

MS (m/e): 453 (M$^+$), 408, 346, 320, 233, 107 and 1.64 g (45%) of (RS)-3-(ethoxycarbonylmethyl)-3-(N'-(4-methylphenyl)ureido)indolin-2-one:

Rf=0.22 (chloroform/methanol=20/1)

NMR (DMSO-d$_6$) δ: 10.39 (s, 1H), 8.79 (s, 1H), 7.24–6.77 (m, 9H), 3.99 (q, J=6.8 Hz, 2H), 2.84 (d, J=14.6 Hz, 1H), 2.63 (d, J=14.6 Hz, 1H), 2.18 (s, 3H), 1.06 (t, J=6.8 Hz, 3H).

MS (m/e): 367 (M$^+$), 321, 206, 133, 107

Example 54

(RS)-3-(N'-(4-Methylphenyl)ureido-1,3-bis(phenylcarbonylmethyl)indolin-2-one (54a) and (RS)-3-(N'-(4-Methylphenyl)ureido-3-(phenylcarbonylmethyl)indolin-2-one (54b)

The two title compounds were prepared in the same manner as in Example 53, except for replacing ethyl bromoacetate used in Example 53 with 2-bromoacetophenone.

(RS)-3-(N'-(4-Methylphenyl)ureido)-1,3-bis(phenylcarbonylmethyl)indolin-2-one:

Rf=0.73 (chloroform/methanol=20/1)

NMR (DMSO-d$_6$) δ: 9.01 (s, 1H), 8.14 (d, J=6.8 Hz, 2H), 7.85 (d, J=6.8 Hz, 2H), 7.67–6.88 (m, 15H), 5.37 (s, 2H), 3.63 (d, J=15.1 Hz, 1H), 3.42 (d, J=15.1 Hz, 1H), 2.19 (s, 3H).

MS (m/e): 517 (M$^+$), 410, 367, 262, 150, 105

(RS)-3-(N'-(4-Methylphenyl)ureido)-3-(phenylcarbonylmethyl)indolin-2-one (54b):

Rf=0.33 (chloroform/methanol=20/1)

NMR (DMSO-d$_6$) δ: 10.41 (s, 1H), 8.81 (s, 1H), 7.88 (d, J=7.3 Hz, 2H), 7.65–7.44 (m, 3H), 7.30–6.77 (m, 9H), 3.68 (d, J=16.5 Hz, 1H), 3.44 (d, J=16.5 Hz, 1H), 2.19 (S, 3H).

MS (m/e): 399 (M$^+$), 381, 338, 266, 249, 107

Example 55

(RS)-3-(Hydroxycarbonylmethyl)-3-(N'-(4-methylphenyl)ureido)indolin-2-one

A solution of 300 mg of potassium hydroxide (85%) in 2 ml of water was added to a solution of 0.35 g of (RS)-3-(ethoxycarbonylmethyl)-3-(N'-(4-methylphenyl)ureido)indolin-2-one in 10 ml of ethanol at room temperature, and the mixture was stirred for 4 hours, followed by concentration. The concentrate was diluted with water, and washed with chloroform. The aqueous layer was adjusted to pH 3 by addition of 2N hydrochloric acid, and extracted with ethyl acetate. The organic layer was dried over sodium sulfate and concentrated. The resulting crude product was recrystallized from isopropyl alcohol to give 0.088 g (27%) of the title compound.

Rf=0.16 (chloroform/methanol=2/1)

NMR (DMSO-d$_6$) δ: 12.70 (br, 1H), 10.36 (s, 1H), 8.88 (s, 1H), 7.26–6.75 (m, 9H), 2.77 (d, J=16.1 Hz, 1H), 2.49 (d, J=16.1 Hz, 1H), 2.18 (s, 3H).

MS (m/e): 339 (M+), 321, 160, 133, 107

Example 56

(RS)-1,3-Bis(hydroxycarbonylmethyl)-3-(N'-(4-methylphenyl)ureido)indolin-2-one

The title compound was obtained (yield: 75%) in the same manner as in Example 55, except for replacing (RS)-3-(ethoxycarbonylmethyl)-3-(N'-(4-methylphenyl)ureido)indolin-2-one used in Example 55 with (RS)-1,3-bis(ethoxycarbonylmethyl)-3-(N'-(4-methylphenyl)ureido)indolin-2-one.

Rf=0.17 (chloroform/methanol=1/1)

NMR (DMSO-d$_6$) δ: 12.71 (br, 2H), 9.07 (s, 1H), 7.31–6.93 (m, 9H), 4.42 (d, J=17.5 Hz, 1H), 4.37 (d, J=17.5 Hz, 1H), 2.82 (d, J=14.9 Hz, 1H), 2.37 (d, J=14.9 Hz, 1H), 2.18 (s, 3H).

MS (m/e): 379 (M$^+$-18), 335, 133, 107

Example 57

(RS)-3-(4-Methylphenyl)aminocarbonylmethyl-3-(N'-(4-methylphenyl)ureido)indolin-2-one To a solution of 0.150 g of (RS)-3-(hydroxycarbonylmethyl)-3-(N'-(4-methylphenyl)ureido)indolin-2-one and 0.103 g of dicyclohexylcarbodiimide in 10 ml of N,N-dimethylformamide were added successively 0.074 g of 1-hydroxybenzotriazole and 0.052 g of p-toluidine. The resulting mixture was stirred at room temperature for 18 hours, followed by concentration. The residue was diluted with ethyl acetate and washed successively with dilute hydrochloric acid and saturated aqueous sodium hydrogencarbonate. The organic layer was dried over anhydrous sodium sulfate and concentrated. The crude product was purified by silica gel column chromatography (chloroform/methanol=20/1) to obtain 0.083 g (44%) of the title compound as a white powder.

Rf=0.11 (chloroform/methanol=20/1)

NMR (DMSO-d$_6$) δ: 10.37 (s, 1H), 9.89 (s, 1H), 9.15 (s, 1H), 8.29 (s, 1H), 7.51–6.80 (m, 12H), 2.75 (d, J=14.1 Hz, 1H), 2.50 (d, J=14.1 Hz, 1H), 2.25 (s, 3H), 2.18 (s, 3H).

MS (m/e): 428 (M$^+$), 410, 321, 295, 147, 133, 107

EXAMPLES 58 TO 59

The following compounds were prepared in the same manner as in Example 57, except for starting with various amines in place of p-toluidine used in Example 57.

Example 58

(RS)-3-(N'-(4-Methylphenyl)ureido)-3-(N-(N'-methylpiperazinyl)carbonylmethyl)indolin-2-one NMR (CDCl$_3$) δ: 9.12 (br, 1H), 7.50 (s, 1H), 7.38–7.15 (m, 2H), 7.15–6.70 (m, 7H), 3.60 (br, 2H), 3.30–2.95 (m, 2H), 2.98 (d, J=14.5 Hz, 1H), 2.75 (d, J=14.5 Hz, 1H), 2.57–1.80 (br, 7H), 2.22 (s, 3H).

Example 59

(RS)-3-(N'-(4-Methylphenyl)ureido)-3-((N-piperidyl)carbonylmethyl)indolin-2-one

NMR (DMSO-d$_6$) δ: 10.31 (s, 1H), 9.11 (s, 1H), 7.45 (s, 1H), 7.40–7.05 (m, 4H), 7.05–6.74 (m, 4H), 3.48 (br, 2H), 3.27–3.00 (br, 2H), 2.71 (d, J=15.1 Hz, 1H), 2.64 (d, J=15.1 Hz, 1H), 2.18 (s, 3H), 1.70–1.12 (br, 6H).

REFERENCE EXAMPLE 24

(RS)-3-(Ethoxycarbonylmethyl)-3-((4-methylbenzyl)carbonylamino)indolin-2-one

To a solution of 0.72 g of (RS)-3-((4-methylbenzyl)carbonylamino)indolin-2-one in 20 ml of dry dimethyl sulfoxide was added 3 ml of a 1M solution of potassium t-butoxide in dry dimethyl sulfoxide at room temperature under a nitrogen atmosphere, followed by stirring for 30 minutes. To the mixture was added dropwise 0.37 ml of ethyl bromoacetate, followed by stirring at the same temperature for 30 minutes. The reaction mixture was treated with an aqueous solution of sodium chloride and extracted with ethyl ether. The ethyl ether layer was dried over anhydrous magnesium sulfate and concentrated. The residue was purified by silica gel column chromatography (chloroform/methanol=40/1) to give 0.30 g (32%) of the title compound.

Rf=0.36 (chloroform/methanol=20/1)

NMR (DMSO-d$_6$) δ: 10.35 (s, 1H), 8.63 (s, 1H), 7.16–7.05 (m, 6H), 6.88–6.71 (m, 2H), 3.82 (q, J=6.8 Hz, 2H), 3.40 (d, J=12.7 Hz, 1H), 3.32 (d, J=12.7 Hz, 1H), 2.95 (d, J=14.6 Hz, 1H), 2.74 (d, J=14.6 Hz, 1H), 2.25 (s, 3H), 0.96 (t, J=6.8 Hz, 3H).

MS (m/e): 366 (M$^+$), 322, 233, 218, 146, 132, 105

REFERENCE EXAMPLE 25

(RS)-1-Benzyl-3-ethoxycarbonylmethyl-3-(methylcarbonylamino)indolin-2-one

To a solution of 0.84 g of (RS)-1-benzyl-3-(methylcarbonylamino)indolin-2-one in 15 ml of dry dimethyl sulfoxide was added 3 ml of a 1M solution of potassium t-butoxide in dry dimethyl sulfoxide at room temperature under a nitrogen atmosphere, followed by stirring for 10 minutes. To the solution was added dropwise 1.11 ml of ethyl bromoacetate, followed by stirring at the same temperature for 30 minutes. The reaction mixture was poured into an aqueous solution of sodium chloride and extracted with ethyl ether. The ethyl ether layer was dried over anhydrous magnesium sulfate and concentrated. The residue was purified by silica gel column chromatography (chloroform/ethyl acetate=3/1) to give 0.83 g (76%) of the title compound as a colorless oil.

Rf=0.21 (chloroform/ethyl acetate=5/1)

NMR (CDCl$_3$) δ: 7.58 (s, 1H), 7.43–7.11 (m, 7H), 6.96 (t, J=7.3 Hz, 1H), 6.66 (d, J=7.8 Hz, 1H), 5.02 (d, J=16.1 Hz, 1H), 4.92 (d, J=16.1 Hz, 1H), 4.21 (q, J=7.3 Hz, 2H), 2.99 (d, J=15.1 Hz, 1H), 2.50 (d, J=15.1 Hz, 1H), 2.02 (s, 3H), 1.25 (t, J=7.3 Hz, 3H).

MS (m/e): 366 (M$^+$), 307, 278, 238, 91

Example 60

(RS)-3-((4-Methylbenzyl)carbonylamino)-3-((4-methylphenyl)aminocarbonylmethyl)indolin-2-one To a solution of 0.29 g of (RS)-3-(ethoxycarbonylmethyl)-3-((4-methylbenzyl)carbonylamino)indolin-2-one in 10 ml of ethanol was added 2 ml of an aqueous solution of 0.16 g of potassium hydroxide (85%) at room temperature, and the mixture was stirred for 4 hours, followed by concentration. The concentrate was diluted with water, and washed with chloroform. The aqueous layer was adjusted to pH 2 by addition of 2N hydrochloric acid and extracted with ethyl acetate. The organic layer was dried over sodium sulfate and concentrated to obtain (RS)-3-(hydroxycarbonylmethyl)-3-((4-methylbenzyl)carbonylamino)indolin-2-one.

Rf=0.24 (chloroform/methanol=2/1)

NMR (DMSO-d$_6$) δ: 12.32 (br, 1H), 10.32 (s, 1H), 8.59 (s, 1H), 7.19–7.05 (m, 6H), 6.88–6.71 (m, 2H), 3.40 (d, J=15.1 Hz, 1H), 3.28 (d, J=15.1 Hz, 1H), 2.89 (d, J=15.1 Hz, 1H), 2.62 (d, J=15.1 Hz, 1H), 2.23 (s, 3H).

MS (m/e): 388 (M$^+$), 294, 205, 146, 132, 105

The above obtained (RS)-3-(hydroxycarbonylmethyl)-3-((4-methylbenzyl)carbonylamino)indolin-2-one was dissolved in 20 ml of N,N-dimethylformamide, and 0.248 g of dicyclohexylcarbodiimide, 0.184 g of 1-hydroxybenzotriazole, and 0.128 g of p-toluidine were successively added thereto. The resulting mixture was stirred at room temperature for 12 hours, followed by concentration. The concentrate was diluted with ethyl acetate, washed successively with dilute hydrochloric acid and saturated aqueous sodium hydrogen-carbonate. The organic layer was dried over anhydrous sodium sulfate, and concentrated. The resulting crude product was purified by silica gel column chromatography (chloroform/methanol=40/1) to afford 0.273 g (81%) of the title compound as a white powder.

Rf=0.28 (chloroform/methanol=20/1)

NMR (DMSO-d$_6$) δ: 10.36 (s, 1H), 9.81 (s, 1H), 8.68 (s, 1H), 7.31 (d, J=8.3 Hz, 2H), 7.14–7.04 (m, 8H), 6.85–6.73 (m, 2H), 3.45 (d, J=15.2 Hz, 1H), 3.35 (d, J=15.2 Hz, 1H), 2.86 (d, J=14.1 Hz, 1H), 2.58 (d, J=14.1 Hz, 1H), 2.26 (s, 3H), 2.23 (s, 3H).

MS (m/e): 427 (M$^+$), 322, 293, 279, 172, 149, 107

Example 61

(RS)-1-Benzyl-3-methylcarbonylamino-3-((4-methylphenyl)aminocarbonylmethyl)indolin-2-one The title compound was prepared in the same manner as in Example 60, except for starting with (RS)-1-benzyl-3-ethoxycarbonylmethyl-3-(methylcarbonylamino)indolin-2-one in place of (RS)-3-(ethoxycarbonylmethyl)-3-((4-methylbenzyl)carbonylamino)indolin-2-one used in Example 60.

Rf=0.43 (chloroform/methanol 10/1)

NMR (CDCl$_3$) δ: 8.23 (s, 1H), 7.57 (s 1H), 7.42–7.12 (m, 11H), 6.95 (t, J=7.3 Hz, 1H), 6.67 (d, J=7.8 Hz, 1H), 4.95 (s, 2H), 3.04 (d, J=14.1 Hz, 1H), 2.33 (s, 3H), 2.25 (d, J=14.1 Hz, 1H), 1.96 (s, 3H).

MS (m/e): 427 (M$^+$), 293, 262, 237, 107, 91

Example 62

(RS)-1-Benzyl-3-((4-methylphenyl)aminocarbonylmethyl)-3-(N'-(4-methylphenyl)ureido)indolin-2-one To a solution of 0.404 g of (RS)-3-(hydroxycarbonylmethyl)-3-(N'-(4-methylphenyl)ureido)indolin-2-one in 20 ml of dry dimethyl sulfoxide was added 2.5 ml of a 1M solution of sodium hydride in dry dimethyl sulfoxide at room temperature under a nitrogen atmosphere. After stirring the mixture for 15 minutes, 0.19 ml of benzyl bromide was added thereto, followed by stirring at the same temperature for 30 minutes. The reaction mixture was poured into an aqueous solution of sodium chloride and extracted with ethyl ether. The ethyl ether layer was dried over anhydrous magnesium sulfate and concentrated to give (RS)-1-benzyl-3-(hydroxycarbonylmethyl)-3-(N'-(4-methylphenyl)ureido)indolin-2-one.

Rf=0.41 (chloroform/methanol=2/1)

(RS)-1-Benzyl-3-(hydroxycarbonylmethyl)-3-(N'-(4-methylphenyl)ureido)indolin-2-one was dissolved in 15 ml of dry N,N-dimethylformamide, and 0.080 g of 1-hydroxybenzotriazole, 0.1 ml of diisopropylethylamine, 0.111 g of 1-ethyl-3-(3-dimethylaminopropyl)carbodiimide hydrochloride, and 0.065 g of p-toluidine were successively added to the solution. The mixture was stirred for 6 hours and concentrated. The concentrate was diluted with ethyl acetate and washed successively with dilute hydrochloric acid and a saturated aqueous solution of sodium hydrogen-carbonate. The organic layer was dried over anhydrous sodium sulfate and concentrated. The crude product was purified by silica gel column chromatography (chloroform/ethyl acetate=4/1) to give 0.350 g (57%) of the title compound as a white powder.

NMR (DMSO-d$_6$) δ: 9.93 (s, 1H), 9.16 (s, 1H), 7.51 (s, 1H), 7.53–6.70 (m, 17H), 4.94 (s, 2H), 2.90 (d, J=14.8 Hz, 1H), 2.57 (d, J=14.8 Hz, 1H), 2.26 (s, 3H), 2.19 (s, 3H).

EXAMPLES 63 TO 70

The following compounds were prepared in the same manner as in Example 62, except for starting with various alkyl halides in place of benzyl bromide used in Example 62.

Example 63

(RS)-3-((4-Methylphenyl)aminocarbonylmethyl)-3-(N'-(4-methylphenyl)ureido)-1-(phenylcarbonylmethyl)indolin-2-one NMR (DMSO-d$_6$) δ: 10.18 (s, 1H), 9.28 (s, 1H), 8.19 (s, 1H), 7.85–6.80 (m, 17H), 5.57 (d, J=8.6 Hz, 1H), 5.36 (d, J=8.6 Hz, 1H), 2.90 (d, J=15.4 Hz, 1H), 2.65 (d, J=15.4 Hz, 1H), 2.82 (s, 3H), 2.20 (s, 3H).

Example 64

(RS)-1-(Ethoxycarbonylmethyl)-3-((4-methylphenyl)aminocarbonylmethyl)-3-(N'-(4-methylphenyl)ureido)indolin-2-one NMR (DMSO-d$_6$) δ: 10.08 (s, 1H), 9.24 (s, 1H), 7.74 (s, 1H), 7.46 (d, J=7.2 Hz, 2H), 7.40–6.88 (m, 10H), 4.78–4.46 (m, 2H), 4.16 (q, J=7.2 Hz, 2H), 2.90 (d, J=14.8 Hz, 1H), 2.57 (d, J=14.8 Hz, 1H), 2.26 (s, 3H), 2.18 (s, 3H), 1.26 (t, J=7.2 Hz, 3H).

Example 65

(RS)-3-((4-Methylphenyl)aminocarbonylmethyl)-3-(N'-(4-methylphenyl)ureido)-1-(2-pyridylmethyl)indolin-2-one NMR (DMSO-d$_6$) δ: 9.96 (s, 1H), 9.21 (s, 1H), 8.30 (s, 1H), 7.80–6.70 (m, 16H), 5.00 (s, 2H), 2.86 (d, J=14.3 Hz, 1H), 2.59 (d, J=14.3 Hz, 1H), 2.50 (s, 3H), 2.25 (s, 3H).

Example 66

(RS)-3-((4-Methylphenyl)aminocarbonylmethyl)-3-(N'-(4-methylphenyl)ureido)-1-(2-phenylethyl)indolin-2-one NMR (DMSO-d$_6$) δ: 9.90 (s, 1H), 9.13 (s, 1H), 7.56 (s, 1H), 7.45–6.85 (m, 17H), 4.98–4.77 (br, 2H), 2.99–2.80 (br, 2H), 2.81 (d, J=14.2 Hz, 1H), 2.48 (d, J=14.2 Hz, 1H), 2.26 (s, 3H), 2.17 (s, 3H).

Example 67

(RS)-1-Methyl-3-((4-methylphenyl)aminocarbonylmethyl)-3-(N'-(4-methylphenyl)ureido)indolin-2-one NMR (DMSO-d$_6$) δ: 9.88 (s, 1H), 9.12 (s, 1H), 7.54 (s, 1H), 7.39 (d, J=8.2 Hz, 2H), 7.31–6.95 (m, 10H), 3.17 (s, 3H), 2.80 (d, J=14.6 Hz, 1H), 2.52 (d, J=14.6 Hz, 1H), 2.25 (s, 3H), 2.18 (s, 3H).

Example 68

(RS)-3-((4-Methylphenyl)aminocarbonylmethyl)-3-(N'-(4-methylphenyl)ureido)-1-(4-pyridylmethyl)indolin-2-one NMR (DMSO-d$_6$) δ: 9.92 (s, 1H), 9.18 (s, 1H), 8.51 (d, J=6.0 Hz, 2H), 7.65 (s, 1H), 7.50 (d, J=5.8 Hz, 2H), 7.40 (d, J=9.8 Hz, 2H), 7.28–6.86 (m, 9H), 6.75 (d, J=7.2 Hz, 1H), 5.03 (d, J=16.6 Hz, 1H), 4.93 (d, J=16.6 Hz, 1H), 2.90 (d, J=14.6 Hz, 1H), 2.63 (d, J=14.6 Hz, 1H), 2.26 (s, 3H), 2.20 (s, 3H).

Example 69

(RS)-1-(Methoxymethyl)-3-((4-methylphenyl)aminocarbonylmethyl)-3-(N'-(4-methylphenyl)ureido)indolin-2-one NMR (DMSO-d$_6$) δ: 9.90 (s, 1H), 9.14 (s, 1H), 7.61 (s, 1H), 7.39 (d, J=7.8 Hz, 2H), 7.45–6.86 (m, 10H), 5.11 (s, 2H), 3.34 (s, 3H), 2.84 (d, J=14.0 Hz, 1H), 2.56 (d, J=14.0 Hz, 1H), 2.25 (s, 3H), 2.17 (s, 3H).

Example 70

(RS)-3-((4-Methylphenyl)aminocarbonylmethyl))-3-(N'-(4-methylphenyl)ureido)-1-(2,2-di-n-propylethyl)indolin-2-one NMR (CDCl$_3$) δ: 8.62 (s, 1H), 7.40–6.78 (m, 14H), 3.71 (dd, J=7.4, 13.7 Hz, 1H), 3.52 (dd, J=6.9, 13.7 Hz, 1H), 2.97 (d, J=14.3 Hz, 1H), 2.62 (d, J=14.3 Hz, 1H), 2.29 (s, 3H), 2.19 (s, 3H), 1.93 (br, 1H), 1.50–1.10 (br, 8H), 0.98–0.70 (br, 6H).

Example 71

(RS)-1-(2,2-Diethoxyethyl)-3-((4-methylphenyl)aminocarbonylmethyl)-3-(N'-(4-methylphenyl)ureido)indolin-2-one To a solution of 0.397 g of (RS)-1-(2,2-diethoxyethyl)-3-(N'-(4-methylphenyl)ureido)indolin-2-one in 4 ml of dry dimethyl sulfoxide was added 1 ml of a 1M solution of potassium t-butoxide in dry dimethyl sulfoxide at room temperature under a nitrogen atmosphere, followed by stirring for 30 minutes. To the mixture was added dropwise a solution of 0.228 g of N-p-tolyl-2-bromoacetamide in 2 ml of dry dimethyl sulfoxide, followed by stirring at the same temperature for 30 minutes. The reaction mixture was poured into an aqueous solution of sodium chloride and extracted with ethyl ether. The ethyl ether layer was dried over anhydrous magnesium sulfate and concentrated. The residue was purified by silica gel column chromatography (hexane/ethyl acetate=2/1) to give 0.35 g (65%) of the title compound.

Rf=0.21 (hexane/ethyl acetate=2/1)

NMR (CDCl$_3$) δ: 8.33 (s, 1H), 7.33–6.91 (m, 14H), 4.77 (dd, J=4.4, 5.6 Hz, 1H), 4.03 (dd, J=5.6, 14.1 Hz, 1H), 3.82–3.48 (m, 5H), 2.97 (d, J=14.6 Hz, 1H), 2.57 (d, J=14.6 Hz, 1H), 2.30 (s, 3H), 2.22 (s, 3H), 1.16 (t, J=6.8 Hz, 3H), 1.11 (t, J=6.8 Hz, 3H).

MS (m/e): 544 (M$^+$), 498, 437, 365, 103, 75

Example 72

(RS)-7-Methyl-3-((4-methylphenyl)aminocarbonylmethyl)-3-(N'-(4-methylphenyl)ureido)indolin-2-one The title compound was prepared (yield: 30%) in the same manner as in Example 71, except for starting with 7-methyl-3-(N'-(4-methylphenyl)ureido)indolin-2-one in place of (RS)-1-(2,2-diethoxyethyl)-3-(N'-(4-methylphenyl)ureido)indolin-2-one used in Example 71.

Rf=0.21 (chloroform/methanol 20/1)

NMR (CDCl₃) δ: 9.10 (br, 1H), 8.61 (br, 1H), 7.42 (br, 1H), 7.26–6.73 (m, 12H), 3.06 (d, J=14.5 Hz, 1H), 2.56 (d, J=14.5 Hz, 1H), 2.24 (s, 3H), 2.19 (s, 3H), 2.03 (s, 3H).

MS (m/e): 442 (M⁺), 424, 381, 335, 161, 107

Example 73

(RS)-3-((4-Methylphenyl)aminocarbonylmethyl)-3-(N'-(4-methylphenyl)ureido)-1-phenylindolin-2-one The title compound was prepared (yield: 57%) in the same manner as in Example 71, except for starting with 3-(N'-(4-methylphenyl)ureido)-1-phenylindolin-2-one in place of (RS)-1-(2,2-diethoxyethyl)-3-(N'-(4-methylphenyl)ureido)indolin-2-one used in Example 71.

Rf=0.40 (chloroform/methanol=20/1)

NMR (DMSO-d₆) δ: 9.97 (s, 1H), 9.12 (s, 1H), 7.63–6.95 (m, 17H), 6.71 (d, J=7.8 Hz, 1H), 2.95 (d, J=14.1 Hz, 1H), 2.75 (d, J=14.1 Hz, 1H), 2.25 (s, 3H), 2.19 (s, 3H).

MS (m/e): 504 (M⁺), 397, 365, 224, 132, 107

EXAMPLES 74 TO 77

The following compounds were prepared in the same manner as in Example 71, except for starting with (RS)-1-(2,2-diethoxyethyl)-3-(N'-(4-methylphenyl)ureido)indolin-2-one, used in Example 71, having a varied substituent at the 5-position thereof.

Example 74

(RS)-1-(2,2-Diethoxyethyl)-5-methyl-3-((4-methylphenyl)aminocarbonylmethyl)-3-(N'-(4-methylphenyl)ureido)indolin-2-one NMR (CDCl₃) δ: 8.25 (s, 1H), 7.32 (d, J=8.3 Hz, 2H), 7.11–6.93 (m, 10H), 6.84 (s, 1H), 4.78 (dd, J=4.4, 5.9 Hz, 1H), 3.99 (dd, J=5.9, 14.6 Hz, 1H), 3.81–3.54 (m, 5H), 2.94 (d, J=14.6 Hz, 1H), 2.54 (d, J=14.6 Hz, 1H), 2.30 (s, 3H), 2.24 (s, 3H), 2.23 (s, 3H), 1.17 (t, J=6.8 Hz, 3H), 1.12 (t, J=6.8 Hz, 3H).

MS (m/e): 558 (M⁺), 512, 451, 406, 379, 306, 103

Example 75

(RS)-1-(2,2-Diethoxyethyl)-5-fluoro-3-((4-methylphenyl)aminocarbonylmethyl)-3-(N'-(4-methylphenyl)ureido)indolin-2-one NMR (CDCl₃) δ: 8.61 (s, 1H), 7.35–6.86 (m, 13H), 4.72 (dd, J=4.5, 5.4 Hz, 1H), 3.96 (dd, J=5.4, 14.6 Hz, 1H), 3.74–3.44 (m, 5H), 2.95 (d, J=14.6 Hz, 1H), 2.65 (d, J=14.6 Hz, 1H), 2.27 (s, 3H), 2.19 (s, 3H), 1.12 (t, J=6.8 Hz, 3H), 1.09 (t, J=6.8 Hz, 3H).

Example 76

(RS)-1-(2,2-Diethoxyethyl)-5-methoxy-3-((4-methylphenyl)aminocarbonylmethyl)-3-(N'-(4-methylphenyl)ureido)indolin-2-one Rf=0.20 (n-hexane/ethyl acetate=2/1)

NMR (CDCl₃) δ: 8.35 (s, 1H), 7.34–6.75 (m, 13H), 4.76 (dd, J=4.3, 6.1 Hz, 1H), 3.99 (dd, J=6.1, 14.5 Hz, 1H), 3.79–3.48 (m, 5H), 3.67 (s, 3H), 2.97 (d, J=14.8 Hz, 1H), 2.61 (d, J=14.8 Hz, 1H), 2.29 (s, 3H), 2.22 (s, 3H), 1.16 (t, J=6.9 Hz, 3H), 1.12 (t, J=6.9 Hz, 3H).

Example 77

(RS)-5-Bromo-1-(2,2-diethoxyethyl)-3-((4-methylphenyl)aminocarbonylmethyl)-3-(N'-(4-methylphenyl)ureido)indolin-2-one NMR (CDCl₃) δ: 8.23 (s, 1H), 7.45–6.85 (m, 13H), 4.73 (dd, J=3.9, 5.9 Hz, 1H), 3.98 (dd, J=5.9 Hz, 14.8 Hz, 1H), 3.83–3.40 (m, 5H), 2.94 (d, J=14.6 Hz, 1H), 2.56 (d, J=14.6 Hz, 1H), 2.29 (s, 3H), 2.21 (s, 3H), 1.15 (t, J=6.8 Hz, 3H), 1.11 (t, J=7.0 Hz, 3H).

EXAMPLES 78 TO 95

The following compounds were prepared in the same manner as in Example 71, except for starting with (RS)-1-(2,2-diethoxyethyl)-3-(N'-(4-methylphenyl)ureido)indolin-2-one, used in Example 71, with its (4-methylphenyl)ureido moiety replaced with various substituted ureides.

Example 78

(RS)-3-(N'-(4-Chlorophenyl)ureido)-1-(2,2-diethoxyethyl)-3-((4-methylphenyl)aminocarbonylmethyl)indolin-2-one Rf=0.33 (n-hexane/ethyl acetate=1/1)

NMR (CDCl₃) δ: 8.34 (s, 1H), 7.54 (s, 1H), 7.31–7.24 (m, 4H), 7.12–6.97 (m, 9H), 4.78 (dd, J=4.4, 5.8 Hz, 1H), 4.03 (dd, J=5.8, 14.6 Hz, 1H), 3.84–3.48 (m, 5H), 3.03 (d, J=14.6 Hz, 1H), 2.65 (d, J=14.6 Hz, 1H), 2.28 (s, 3H), 1.19–1.07 (m, 6H).

Example 79

(RS)-1-(2,2-Diethoxyethyl)-3-(N'-(4-methoxyphenyl)ureido)-3-((4-methylphenyl)aminocarbonylmethyl)indolin-2-one Rf=0.23 (n-hexane/ethyl acetate=1/1)

NMR (CDCl₃) δ: 8.33 (s, 1H), 7.33–6.95 (m, 12H), 6.67 (d, J=8.8 Hz, 2H), 4.76 (dd, J=4.5, 5.9 Hz, 1H), 4.04 (dd, J=5.9, 14.1 Hz, 1H), 3.79–3.48 (m, 5H), 3.70 (s, 3H), 2.95 (d, J=14.6 Hz, 1H), 2.56 (d, J=14.6 Hz, 1H), 2.29 (s, 3H), 1.15 (t, J=6.9 Hz, 3H), 1.10 (t, J=6.8 Hz, 3H).

MS (m/e): 560 (M⁺), 514, 365, 217, 103

Example 80

(RS)-1-(2,2-Diethoxyethyl)-3-((4-methylphenyl)aminocarbonylmethyl)-3-(N'-cyclohexylureido)indolin-2-one Rf=0.25 (n-hexane/ethyl acetate=2/1)

NMR (CDCl₃) δ: 8.14 (s, 1H), 7.38–6.93 (m, 9H), 6.80 (s, 1H), 4.80–4.75 (m, 1H), 4.12 (dd, J=5.8, 14.6 Hz, 1H), 3.78–3.34 (m, 6H), 2.94 (d, J=14.6 Hz, 1H), 2.45 (d, J=14.6 Hz, 1H), 2.31 (s, 3H), 1.95–1.48 (m, 6H), 1.38–0.92 (m, 10H).

MS (m/e): 536 (M⁺), 490, 462, 391, 103

Example 81

(RS)-1-(2,2-Diethoxyethyl)-3-((4-methylphenyl)aminocarbonylmethyl)-3-(N'-(3-methylphenyl)ureido)indolin-2-one NMR (CDCl₃) δ: 8.39 (s, 1H), 7.34–6.97 (m, 13H), 6.75 (d, J=6.8 Hz, 1H), 4.79 (dd, J=4.4, 5.9 Hz, 1H), 4.01 (dd, J=5.9, 14.4 Hz, 1H), 3.84–3.46 (m, 5H), 2.98 (d, J=14.6 Hz, 1H), 2.59 (d, J=14.6 Hz, 1H), 2.30 (s, 3H), 2.19 (s, 3H), 1.16 (t, J=6.8 Hz, 3H), 1.11 (t, J=6.8 Hz, 3H).

MS (m/e): 544 (M⁺), 498, 470, 437, 365, 292, 157, 103, 75

Example 82

(RS)-1-(2,2-Diethoxyethyl)-3-(N'-(4-fluorophenyl)ureido)-3-((4-methylphenyl)aminocarbonylmethyl)indolin-2-one NMR (DMSO-d₆) δ: 9.27 (s, 1H), 7.62 (s, 1H), 7.40–6.86 (m, 13H), 4.71 (dd, J=4.6, 5.6 Hz, 1H), 3.86 (dd, J=5.6, 14.2

Hz, 1H), 3.70–3.35 (m, 5H), 2.84 (d, J=15.2 Hz, 1H), 2.50 (d, J=15.2 Hz, 1H), 2.24 (s, 3H), 1.11 (t, J=6.4 Hz, 3H), 1.07 (t, J=6.4 Hz, 3H).

MS (m/e): 548 (M⁺), 502, 365, 292, 158, 103, 75

Example 83

(RS)-3-(N'-(2-Chlorophenyl)ureido)-1-(2,2-diethoxyethyl)-3-((4-methylphenyl)aminocarbonylmethyl)indolin-2-one NMR (DMSO-d₆) δ: 9.85 (s, 1H), 8.63 (s, 1H), 8.15 (s, 1H), 7.83 (d, J=7.3 Hz, 1H), 7.38–6.88 (m, 11H), 4.70 (dd, J=4.9, 5.4 Hz, 1H), 3.84 (dd, J=5.4, 13.7 Hz, 1H), 3.70–3.37 (m, 5H), 2.97 (d, J=14.6 Hz, 1H), 2.61 (d, J=14.6 Hz, 1H), 2.23 (s, 3H), 1.07 (t, J=7.3 Hz, 6H).

MS (m/e): 564 (M⁺), 490, 365, 292, 173, 103, 75

Example 84

(RS)-1-(2,2-Diethoxyethyl)-3-((4-methylphenyl)aminocarbonylmethyl)-3-(N'-phenylureido)indolin-2-one NMR (CDCl₃) δ: 8.58 (s, 1H), 7.46 (s, 1H), 7.31–6.84 (m, 14H), 4.77 (dd, J=3.9, 5.9 Hz, 1H), 4.00 (dd, J=5.9, 14.1 Hz, 1H), 3.82–3.46 (m, 5H), 2.99 (d, J=14.6 Hz, 1H), 2.67 (d, J=14.6 Hz, 1H), 2.27 (s, 3H), 1.13 (t, J=7.3 Hz, 3H), 1.10 (t, J=7.3 Hz, 3H).

MS (m/e): 530 (M⁺), 365, 292, 217, 158, 103, 75

Example 85

(RS)-1-(2,2-Diethoxyethyl)-3-(N'-(3-methoxyphenyl)ureido)-3-((4-methylphenyl)aminocarbonylmethyl)indolin-2-one NMR (CDCl₃) δ: 8.24 (s, 1H), 7.35–6.91 (m, 12H), 6.73 (d, J=7.3 Hz, 1H), 6.50 (dd, J=2.4, 7.8 Hz, 1H), 4.79 (dd, J=3.9, 6.3 Hz, 1H), 3.98 (dd, J=6.3, 14.1 Hz, 1H), 3.86–3.52 (m, 5H), 3.67 (s, 3H), 2.98 (d, J=14.6 Hz, 1H), 2.54 (d, J=14.6 Hz, 1H), 2.30 (s, 3H), 1.18 (t, J=6.8 Hz, 3H), 1.10 (t, J=6.8 Hz, 3H).

MS (m/e): 560 (M⁺), 365, 350, 292, 217, 149, 103, 75

Example 86

(RS)-1-(2,2-Diethoxyethyl)-3-(N'-ethylureido)-3-((4-methylphenyl)aminocarbonylmethyl)indolin-2-one NMR (CDCl₃) δ: 7.97 (s, 1H), 7.37–6.88 (m, 9H), 4.79 (dd, J=3.9, 6.3 Hz, 1H), 4.57 (br, 1H), 4.09 (dd, J=6.3, 14.6 Hz, 1H), 3.74–3.52 (m, 5H), 3.11–3.05 (m, 2H), 2.94 (d, J=14.6 Hz, 1H), 2.44 (d, J=14.6 Hz, 1H), 2.32 (s, 3H), 1.18 (t, J=7.3 Hz, 3H), 1.14 (t, J=6.8 Hz, 3H), 1.02 (t, J=7.3 Hz, 3H).

MS (m/e): 482 (M⁺), 416, 408, 216, 103, 75

Example 87

(RS)-3-(N'-(4-Ethoxycarbonylphenyl)ureido)-1-(2,2-diethoxyethyl)-3-((4-methylphenyl)aminocarbonylmethyl)indolin-2-one NMR (CDCl₃) δ: 8.16 (br, 1H), 7.79 (d, J=8.8 Hz, 2H), 7.49–6.97 (m, 12H), 4.81 (dd, J=4.9, 6.3 Hz, 1H), 4.30 (q, J=7.3 Hz, 2H), 4.02 (dd, J=6.3, 15.1 Hz, 1H), 3.89–3.57 (m, 5H), 3.02 (d, J=14.6 Hz, 1H), 2.57 (d, J=14.6 Hz, 1H), 2.30 (s, 3H), 1.34 (t, J=7.3 Hz, 3H), 1.19 (t, J=6.8 Hz, 3H), 1.12 (t, J=7.3 Hz, 3H).

MS (m/e): 602 (M⁺), 365, 146, 120, 103, 75

Example 88

(RS)-1-(2,2-Diethoxyethyl)-3-((4-methylphenyl)aminocarbonylmethyl)-3-(N'-(2-methylphenyl)ureido)indolin-2-one NMR (DMSO-d₆) δ: 9.86 (s, 1H), 8.28 (s, 1H), 7.80 (s, 1H), 7.52 (d, J=8.3 Hz, 1H), 7.39–6.79 (m, 11H), 4.71 (dd, J=4.9, 5.4 Hz, 1H), 3.85 (dd, J=5.4, 14.1 Hz, 1H), 3.70–3.37 (m, 5H), 2.93 (d, J=14.6 Hz, 1H), 2.55 (d, J=14.6 Hz, 1H), 2.25 (s, 3H), 2.17 (s, 3H), 1.10 (t, J=6.8 Hz, 3H), 1.07 (t, J=6.8 Hz, 3H).

Example 89

(RS)-3-(N'-(3-Chlorophenyl)ureido)-1-(2,2-diethoxyethyl)-3-((4-methylphenyl)aminocarbonylmethyl)indolin-2-one NMR (DMSO-d₆) δ: 9.97 (s, 1H), 9.49 (s, 1H), 7.76 (s, 1H), 7.54 (s, 1H), 7.41 (d, J=8.3 Hz, 2H), 7.24–6.89 (m, 9H), 4.75 (dd, J=4.3, 5.9 Hz, 1H), 3.86 (dd, J=5.9, 14.2 Hz, 1H), 3.76–3.51 (m, 5H), 2.84 (d, J=15.2 Hz, 1H), 2.09 (d, J=15.2 Hz, 1H), 2.26 (s, 3H), 1.14 (t, J=6.8 Hz, 3H), 1.08 (t, J=6.8 Hz, 3H).

Example 90

(RS)-1-(2,2-Diethoxyethyl)-3-(N'-(2-methoxyphenyl)ureido)-3-((4-methylphenyl)aminocarbonylmethyl)indolin-2-one NMR (DMSO-d₆) δ: 9.80 (br, 1H), 8.44 (s, 1H), 7.95 (s, 1H), 7.79 (d, J=8.3 Hz, 1H), 7.35–6.71 (m, 11H), 4.70 (dd, J=5.0, 5.0 Hz, 1H), 3.92–3.42 (m, 6H), 3.84 (s, 3H), 2.94 (d, J=14.4 Hz, 1H), 2.60 (d, J=14.4 Hz, 1H), 2.23 (s, 3H), 1.08 (t, J=7.3 Hz, 6H).

MS (m/e): 560 (M⁺), 514, 392, 365, 173, 158, 130, 103, 75

Example 91

(RS)-1-(2,2-Diethoxyethyl)-3-((4-methylphenyl)aminocarbonylmethyl)-3-(N'-(4-nitrophenyl)ureido)indolin-2-one NMR (DMSO-d₆) δ: 10.03 (d, J=10.2 Hz, 2H), 8.04 (t, J=9.3 Hz, 3H), 7.53–6.89 (m, 10H), 4.74 (dd, J=5.3, 5.9 Hz, 1H), 3.89 (dd, J=5.9, 14.2 Hz, 1H), 3.72–3.50 (m, 5H), 2.86 (d, J=15.1 Hz, 1H), 2.51 (d, J=15.1 Hz, 1H), 2.26 (s, 3H), 1.13 (t, J=6.8 Hz, 3H), 1.09 (t, J=7.3 Hz, 3H).

Example 92

(RS)-3-(N'-(4-Cyanophenyl)ureido)-1-(2,2-diethoxyethyl)-3-((4-methylphenyl)aminocarbonylmethyl)indolin-2-one NMR (CDCl₃) δ: 8.05 (s, 1H), 7.89 (s, 1H), 7.57 (s, 1H), 7.37–6.98 (m, 12H), 4.82 (dd, J=3.9, 6.3 Hz, 1H), 4.07 (dd, J=6.3, 15.2 Hz, 1H), 3.87–3.54 (m, 5H), 3.09 (d, J=14.6 Hz, 1H), 2.58 (d, J=14.6 Hz, 1H), 2.30 (s, 3H), 1.20 (t, J=7.3 Hz, 3H), 1.14 (t, J=7.3 Hz, 3H).

Example 93

(RS)-1-(2,2-Diethoxyethyl)-3-(N'-(3-trifluoromethylphenyl)ureido)-3-((4-methylphenyl)aminocarbonylmethyl)indolin-2-one NMR (CDCl₃) δ: 8.32 (s, 1H), 7.62 (d, J=4.4 Hz, 2H), 7.43 (s, 1H), 7.34–6.97 (m, 11H), 4.81 (dd, J=3.9, 5.9 Hz, 1H), 3.96–3.57 (m, 6H), 3.07 (d, J=14.6 Hz, 1H), 2.62 (d, J=14.6 Hz, 1H), 2.29 (s, 3H), 1.19 (t, J=6.8 Hz, 3H), 1.09 (t, J=7.3 Hz, 3H).

Example 94

(RS)-1-(2,2-Diethoxyethyl)-3-(N'-(3-fluorophenyl) ureido)-3-((4-methylphenyl)aminocarbonylmethyl) indolin-2-one NMR (CDCl$_3$) δ: 8.46 (s, 1H), 7.68 (s, 1H), 7.35–6.93 (m, 11H), 6.79 (d, J=7.8 Hz, 1H), 6.55 (split-t, J=8.8 Hz, 1H), 4.79 (dd, J=3.9, 5.9 Hz, 1H), 3.98 (dd, J=5.9, 14.4 Hz, 1H), 3.88–3.49 (m, 5H), 3.04 (d, J=14.6 Hz, 1H), 2.66 (d, J=14.6 Hz, 1H), 2.28 (s, 3H), 1.16 (t, J=7.3 Hz, 3H), 1.11 (t, J=7.3 Hz, 3H).

Example 95

(RS)-1-(2,2-Diethoxyethyl)-3-(N'-(4-trifluoromethylphenyl)ureido)-3-((4-methylphenyl) aminocarbonylmethyl)indolin-2-one Rf=0.43 (n-hexane/ethyl acetate=1/1)

NMR (DMSO-d$_6$) δ: 9.99 (s, 1H), 9.71 (s, 1H), 7.84 (s, 1H), 7.48–6.89 (m, 12H), 4.74 (dd, J=3.2, 5.8 Hz, 1H), 3.88 (dd, J=5.8, 13.6 Hz, 1H), 3.72–3.51 (m, 5H), 2.86 (d, J=13.7 Hz, 1H), 2.51 (d, J=13.7 Hz, 1H), 2.26 (s, 3H), 1.13 (t, J=7.3 Hz, 3H), 1.09 (t, J=7.3 Hz, 3H).

Example 96

(RS)-3-((4-Methylphenyl)aminocarbonylmethyl)-3-(N'-(4-methylphenyl)ureido)-1-(2,2-dipropoxyethyl) indolin-2-one To a solution of 0.411 g of (RS)-1-(2,2-diethoxyethyl)-3-((4-methylphenyl)aminocarbonylmethyl)-3-(N'-(4-methylphenyl)ureido)indolin-2-one in 50 ml of n-propanol was added 10 mg of p-toluenesulfonic acid, and the mixture was heated under reflux for 2 hours. The reaction mixture was concentrated, and the residue was purified by silica gel column chromatography (hexane/ethyl acetate=3/1) to give 0.394 g (91%) of the title compound.

Rf=0.64 (hexane/ethyl acetate=1/1)

NMR (CDCl$_3$) δ: 8.55 (s, 1H), 7.35–6.80 (m, 14H), 4.74 (dd, J=4.4, 5.4 Hz, 1H), 3.99 (dd, J=5.4, 14.6 Hz, 1H), 3.75 (dd, J=4.4, 14.6 Hz, 1H), 3.68–3.32 (m, 4H), 2.95 (d, J=14.6 Hz, 1H), 2.62 (d, J=14.6 Hz, 1H), 2.29 (s, 3H), 2.20 (s, 3H), 1.62–1.38 (m, 4H), 0.91–0.70 (m, 6H).

Example 97

(RS)-1-(Formylmethyl)-3-((4-methylphenyl) aminocarbonylmethyl)-3-(N'-(4-methylphenyl) ureido)indolin-2-one To a solution of 4.32 g of (RS)-1-(2,2-diethoxyethyl)-3-((4-methylphenyl)aminocarbonylmethyl)-3-(N'-(4-methylphenyl)ureido)indolin-2-one in 50 ml of acetone was added 5 ml of 2N hydrochloric acid, and the mixture was stirred at room temperature for 2 hours. The reaction mixture was poured into water, and the thus formed precipitate was collected by filtration and washed with ethyl ether to obtain 2.94 g (79%) of the title compound.

NMR (DMSO-d$_6$) δ: 10.03 (s, 1H), 9.66 (s, 1H), 7.70 (s, 1H), 7.43 (d, J=8.2 Hz, 2H), 7.28–6.81 (m, 11H), 4.76 (d, J=18.0 Hz, 1H), 4.58 (d, J=18.0 Hz, 1H), 2.87 (d, J=14.8 Hz, 1H), 2.58 (d, J=14.6 Hz), 2.26 (s, 3H), 2.18 (s, 3H).

Example 98

(RS)-3-((4-Methylphenyl)aminocarbonylmethyl)-3-(N'-(4-methylphenyl)ureido)-1-((2,5-dioxacyclopentyl)methyl)indolin-2-one To a solution of 0.294 g of (RS)-1-(formylmethyl)-3-((4-methylphenyl)aminocarbonylmethyl)-3-(N'-(4-methylphenyl)ureido)indolin-2-one in 50 ml of toluene were added 0.5 ml of ethylene glycol and 10 mg of p-toluenesulfonic acid. The mixture was heated under reflux for 6 hours while azeotropically removing produced water together with toluene. The reaction mixture was washed with saturated aqueous sodium hydrogencarbonate. The organic layer was dried over anhydrous sodium sulfate and concentrated. The residue was purified by silica gel column chromatography (hexane/ethyl acetate=2/1) to give 0.220 g (68%) of the title compound.

NMR (DMSO-d$_6$) δ: 9.94 (s, 1H), 9.15 (s, 1H), 7.62 (s, 1H), 7.41 (d, J=8.2 Hz, 2H), 7.27–7.01 (m, 7H), 6.99–6.85 (m, 3H), 5.15–5.03 (m, 1H), 4.05–3.63 (m, 6H), 2.83 (d, J=14.3 Hz, 1H), 2.47 (d, J=14.3 Hz, 1H), 2.25 (s, 3H), 2.17 (s, 3H).

EXAMPLES 99 TO 101

The following compounds were prepared in the same manner as in Example 98, except for replacing ethylene glycol used in Example 98 with various alcohols.

Example 99

(RS)-1-(2,2-Dibenzyloxyethyl)-3-((4-methylphenyl) aminocarbonylmethyl)-3-(N'-(4-methylphenyl) ureido)indolin-2-one NMR (DMSO-d$_6$) δ: 9.90 (s, 1H), 9.11 (s, 1H), 7.60 (s, 1H), 7.45–6.85 (m, 22H), 5.03 (dd, J=5.1, 6.8 Hz, 1H), 4.71 (d, J=11.7 Hz, 2H), 4.61 (d, J=11.7 Hz, 2H), 4.10–3.83 (m, 2H), 2.84 (d, J=14.8 Hz, 1H), 2.51 (d, J=14.8 Hz, 1H), 2.25 (s, 3H), 2.17 (s, 3H).

Example 100

(RS)-1-(2,2-Dimethoxyethyl)-3-((4-methylphenyl) aminocarbonylmethyl)-3-(N'-(4-methylphenyl) ureido)indolin-2-one NMR (DMSO-d$_6$) δ: 9.96 (s, 1H), 9.15 (s, 1H), 7.63 (s, 1H), 7.41 (d, J=8.2 Hz, 2H), 7.30–7.00 (m, 7H), 7.00–6.80 (m, 3H), 4.63 (dd, J=4.3, 5.9 Hz, 1H), 3.91 (dd, J=5.9 Hz, 14.3 Hz, 1H), 3.69 (dd, J=4.3 Hz, 14.3 Hz, 1H), 3.36 (s, 3H), 3.34 (s, 3H), 2.86 (d, J=14.3 Hz, 1H).

Example 101

(RS)-3-((4-Methylphenyl)aminocarbonylmethyl)-3-(N'-(4-methylphenyl)ureido)-1-((2.6-dioxa-3,5-dimethylcyclohexyl)methyl)indolin-2-one NMR (CDCl$_3$) δ: 8.46 (s, 1H), 7.33–6.80 (m, 14H), 4.83 (dd, J=4.9, 4.9 Hz, 1H), 4.12 (dd, J=4.9, 14.3 Hz, 1H), 3.78 (dd, J=4.9, 14.3 Hz, 1H), 3.62 (br, 2H), 2.99 (d, J=14.6 Hz, 1H), 2.68 (d, J=14.6 Hz, 1H), 2.26 (s, 3H), 2.19 (s, 3H), 1.50–0.95 (m, 8H).

Example 102

(RS)-1-(2-Methylamino)ethyl-3-((4-methylphenyl) aminocarbonylmethyl)-3-(N'-(4-methylphenyl) ureido)indolin-2-one To a solution of 0.439 of (RS)-1-(formylmethyl)-3-((4-methylphenyl)aminocarbonylmethyl)-3-(N'-(4- methylphenyl)ureido)indolin-2-one in 15 ml of methanol was added 1 ml of a 40% aqueous solution of methylamine at room temperature. After adjusting the mixture to pH 7 with trifluoroacetic acid, 0.30 g of sodium cyanoborohydride was added thereto. The resulting mixture was stirred at room temperature for 1 day and then concentrated. The concentrate was diluted with ethyl acetate and washed with an aqueous solution of sodium chloride. The organic layer was dried over anhydrous sodium sulfate and concentrated. The crude product was purified by silica gel column chromatography (hexane/ethyl acetate=1/1) to afford 0.39 g (90%) of the title compound.

NMR (CDCl$_3$, for hydrochloride) δ: 9.10–8.75 (br, 1H), 7.95–7.50 (br, 2H), 7.30–6.65 (m, 12H), 4.15–3.70 (br, 2H), 3.10–2.38 (br, 7H), 2.24 (brs, 3H), 2.16 (brs, 3H).

Example 103

(RS)-3-((4-Methylphenyl)aminocarbonylmethyl)-3-(N'-(4-methylphenyl)ureido)-1-(2-(1-piperidyl)ethyl) indolin-2-one The title compound was prepared (yield: 63%) in the same manner as in Example 102, except for replacing methylamine used in Example 102 with piperidine.

NMR (CDCl$_3$) δ: 9.10 (s, 1H), 8.04 (s, 1H), 7.73 (s, 1H), 7.40–6.70 (m, 12H), 4.10 (br, 2H), 3.10 (br, 8H), 2.23 (br, 3H), 2.20 (br, 3H).

Example 104

(RS)-1-(2-Dimethylaminoethyl)-3-((4-methylphenyl)aminocarbonylmethyl)-3-(N'-(4-methylphenyl)ureido)indolin-2-one The title compound was prepared in the same manner as in Example 102, except for replacing methylamine used in Example 102 with dimethylamine.

NMR (DMSO-d$_6$) δ: 9.92 (s, 1H), 9.13 (s, 1H), 7.57 (s, 1H), 7.40 (d, J=8.4 Hz, 2H), 7.30–6.86 (m, 10H), 3.99–3.58 (m, 2H), 3.60–3.10 (m, 1H), 2.82 (d, J=14.6 Hz, 1H), 2.70–2.35 (m, 2H), 2.28 (s, 6H), 2.25 (s, 3H), 2.18 (s, 3H).

Example 105

(RS)-3-((4-Methylphenyl)aminocarbonylmethyl)-3-(N'-(4-methylphenyl)ureido)-1-(2,2-bis(methylthio)ethyl)indolin-2-one Excess methyl mercaptan was bubbled through a solution of 0.538 g of (RS)-1-(2,2-diethoxyethyl)-3-((4-methylphenyl)aminocarbonylmethyl)-3-(N'-(4-methylphenyl)ureido)indolin-2-one in 30 ml of dichloromethane at −10° C., and 0.30 ml of boron trifluoride ethyl etherate was added thereto, followed by stirring at room temperature for 1 hour. The reaction mixture was diluted with dichloromethane and washed successively with a 1N sodium hydroxide aqueous solution and water. The organic layer was dried over anhydrous sodium sulfate and concentrated. The residue was washed with hexane/ethyl acetate=1/1 to give 0.495 g (91%) of the title compound.

Rf=0.48 (hexane/ethyl acetate=1/1)

NMR (DMSO-d$_6$) δ: 10.02 (s, 1H), 9.19 (s, 1H), 7.65 (s, 1H), 7.52–6.83 (m, 12H), 4.30–3.94 (m, 2H), 3.85 (dd, J=6.4, 14.2 Hz, 1H), 2.86 (d, J=14.2 Hz, 1H), 2.54 (d, J=14.2 Hz, 1H), 2.25 (s, 3H), 2.20 (s, 3H), 2.17 (s, 3H), 2.13 (s, 3H).

Example 106

(RS)-1-(2,2-Bis(ethylthio)ethyl)-3-((4-methylphenyl)aminocarbonylmethyl)-3-(N'-(4-methylphenyl)ureido)indolin-2-one To a solution of 0.512 g of (RS)-1-(2,2-diethoxyethyl)-3-((4-methylphenyl)aminocarbonylmethyl)-3-(N'-(4-methylphenyl)ureido)indolin-2-one in 30 ml of dichloromethane were added successively 0.8 ml of ethyl mercaptan and 0.30 ml of boron trifluoride ethyl etherate at room temperature, and the mixture was stirred at room temperature for 1 hour. The reaction mixture was washed with a 1N sodium hydroxide aqueous solution, and the organic layer was dried over anhydrous sodium sulfate and concentrated. The residue was washed with hexane/ethyl acetate=1/1 to give 0.542 g (100%) of the title compound.

Rf=0.62 (n-hexane/ethyl acetate=1/1)

NMR (DMSO-d$_6$) δ: 10.00 (s, 1H), 9.17 (s, 1H), 7.64 (s, 1H), 7.43 (d, J=8.2 Hz, 2H), 7.30–6.78 (m, 10H), 4.38–4.26 (m, 1H), 4.14–3.79 (m, 2H), 2.86 (d, J=14.8 Hz, 1H), 2.75 (q, J=7.3 Hz, 2H), 2.69 (q, J=7.3 Hz, 2H), 2.38 (d, J=14.8 Hz, 1H), 2.26 (s, 3H), 2.17 (s, 3H), 1.23 (t, J=7.3 Hz, 3H), 1.17 (t, J=7.3 Hz, 3H).

Example 107

(RS)-3- (Ethoxycarbonylmethyl)-1-(2,2-diethoxyethyl )-3- (N'-(4-methylphenyl)ureido) indolin-2-one To a solution of 7.50 g of (RS)-1-(2,2-diethoxyethyl)-3-(N'-(4-methylphenyl)ureido)indolin-2-one in 100 ml of dry dimethyl sulfoxide was added 20 ml of a 1M solution of potassium t-butoxide in dry dimethyl sulfoxide at room temperature under a nitrogen atmosphere, followed by stirring for 30 minutes. To the mixture was added dropwise a solution of 2.30 ml of ethyl bromoacetate in 20 ml of dry dimethyl sulfoxide, followed by stirring at the same temperature for 30 minutes. A sodium chloride aqueous solution was added thereto, and the mixture was extracted with ethyl ether. The ethyl ether layer was dried over anhydrous magnesium sulfate and concentrated. The residue was purified by silica gel column chromatography (hexane/ethyl acetate=3/1) to afford 8.21 g (90%) of the title compound.

NMR (CDCl$_3$) δ: 7.34–7.24 (m, 2H), 7.19–6.95 (m, 7H), 6.76 (s, 1H), 4.76 (dd, J=4.6, 5.9 Hz, 1H), 4.16–3.95 (m, 3H), 3.89–3.50 (m, 5H), 2.93 (d, J=15.4 Hz, 1H), 2.59 (d, J=15.4 Hz, 1H), 2.26 (s, 3H), 1.23–1.10 (m, 9H).

Example 108

(RS)-1-(2,2-Diethoxyethyl)-3-(hydroxycarbonylmethyl)-3-(N'-(4-methylphenyl)ureido)indolin-2-one To a solution of 8.21 g of (RS)-3-(ethoxycarbonylmethyl)-1-(2,2-diethoxyethyl)-3-(N'-(4-methylphenyl)ureido)indolin-2-one in 100 ml of methanol was added 30 ml of an aqueous solution of 2.0 g of potassium hydroxide (85%) at room temperature, followed by stirring for 6 hours. The reaction mixture was concentrated, and the concentrate was diluted with water, which was washed with chloroform. The aqueous layer was adjusted to pH 2 by addition of 2N hydrochloric acid, and extracted with chloroform, and the organic layer was dried over anhydrous sodium sulfate and concentrated to yield 6.63 g (86%) of the title compound.

NMR (CDCl$_3$) δ: 7.74 (s, 1H), 7.35–6.70 (m, 10H), 4.73 (dd, J=4.4, 5.9 Hz, 1H), 4.01 (dd, J=5.9, 14.6 Hz, 1H), 3.86–3.38 (m, 5H), 2.90 (d, J=15.9 Hz, 1H), 2.65 (d, J=15.9 Hz, 1H), 2.18 (s, 3H), 1.13 (t, J=6.8 Hz, 3H), 1.08 (t, J=6.8 Hz, 3H).

Example 109

(RS)-1-(2,2-Diethoxyethyl)-3-((N-methyl)-(N-phenyl)amino)carbonylmethyl)-3-(N'-(4-methylphenyl)ureido)indolin-2-one In 50 ml of dichloromethane was dissolved 0.360 g of (RS)-1-(2,2-ethoxyethyl)-3-(hydroxycarbonylmethyl)-3-

(N'-(4-methylphenyl)ureido)indolin-2-one, and 0.180 g of 4-dimethylaminopyridine, 0.180 g of 1-ethyl-3-(3-dimethylaminopropyl)carbodiimide hydrochloride, and 0.095 ml of N-methylaniline were successively added to the solution. The mixture was stirred for 8 hours, followed by concentration. The residue was diluted with ethyl acetate and washed successively with dilute hydrochloric acid and saturated aqueous sodium hydrogencarbonate. The organic layer was dried over anhydrous sodium sulfate and concentrated. The crude product was purified by silica gel column chromatography (hexane/ethyl acetate=2/1) to give 0.278 g (65%) of the title compound as a white powder.

NMR (CDCl$_3$) δ: 7.83 (s, 1H), 7.39–6.83 (m, 12H), 6.63 (br, 2H), 4.55 (dd, J=5.4, 5.8 Hz, 1H), 3.87 (dd, J=5.8, 14.2 Hz, 1H), 3.75–3.28 (m, 5H), 3.24 (s, 3H), 2.64 (d, J=14.6 Hz, 1H), 2.27 (d, J=14.6 Hz, 1H), 2.24 (s, 3H), 1.06 (t, J=6.8 Hz, 3H), 1.03 (t, J=6.8 Hz, 3H).

EXAMPLES 110 TO 137

The following compounds were prepared in the same manner as in Example 109, except for using various amines in place of N-methylaniline used in Example 109 as a starting material.

Example 110

(RS)-1-(2,2-Diethoxyethyl)-3-((4-methoxycarbonylphenyl)aminocarbonylmethyl)-3-(N'-(4-methylphenyl)ureido)indolin-2-one NMR (CDCl$_3$) δ: 9.03 (s, 1H), 7.89 (d, J=8.8 Hz, 2H), 7.49 (d, J=8.8 Hz, 2H), 7.48–7.26 (m, 4H), 7.26–6.82 (m, 6H), 4.76 (dd, J=4.4, 6.0 Hz, 1H), 3.99 (dd, J=6.0, 14.3 Hz, 1H), 3.89 (s, 3H), 3.89–3.40 (m, 5H), 3.01 (d, J=15.2 Hz, 1H), 2.75 (d, J=15.2 Hz, 1H), 2.19 (s, 3H), 1.12 (t, J=7.0 Hz, 3H), 1.09 (t, J=6.8 Hz, 3H).

Example 111

(RS)-1-(2,2-Diethoxyethyl)-3-((3-methylphenyl)aminocarbonylmethyl)-3-(N'-(4-methylphenyl)ureido)indolin-2-one NMR (CDCl$_3$) δ: 8.51 (s, 1H), 7.35–6.86 (m, 14H), 4.77 (dd, J=4.4, 5.9 Hz, 1H), 4.01 (dd, J=5.9, 13.7 Hz, 1H), 3.85–3.40 (m, 5H), 2.98 (d, J=14.3 Hz, 1H), 2.64 (d, J=14.3 Hz, 1H), 2.27 (s, 3H), 2.20 (s, 3H), 1.14 (t, J=7.4 Hz, 3H), 1.10 (t, J=6.8 Hz, 3H).

Example 112

(RS)-1-(2,2-Diethoxyethyl)-3-((2-methylphenyl)aminocarbonylmethyl)-3-(N'-(4-methylphenyl)ureido)indolin-2-one NMR (DMSO-d$_6$) δ: 9.43 (s, 1H), 9.04 (s, 1H), 7.56 (s, 1H), 7.34–6.80 (m, 12H), 4.77–4.65 (m, 1H), 3.86 (dd, J=5.7, 13.1 Hz, 1H), 3.76–3.40 (m, 5H), 2.89 (d, J=14.3 Hz, 1H), 2.62 (d, J=14.3 Hz, 1H), 2.18 (s, 3H), 2.06 (s, 3H).

Example 113

(RS)-1-(2,2-Diethoxyethyl)-3-(N'-(4-methylphenyl)ureido)-3-(n-propylaminocarbonylmethyl)indolin-2-one NMR (CDCl$_3$) δ: 7.41 (s, 1H), 7.34–6.90 (m, 9H), 6.28 (br, 1H), 4.78 (dd, J=4.4 Hz, 5.8 Hz, 1H), 4.00 (dd, J=5.8, 13.7 Hz, 1H), 3.89–3.44 (m, 5H), 3.17 (br, 2H), 2.83 (d, J=14.8 Hz, 1H), 2.36 (d, J=14.8 Hz, 1H), 2.23 (s, 3H), 1.47 (q, J=7.4 Hz, 2H), 1.18 (t, J=7.4 Hz, 3H), 1.11 (t, J=7.4 Hz, 3H), 0.86 (t, J=7.4 Hz, 3H).

Example 114

(RS)-3-((4-Chlorophenyl)aminocarbonylmethyl)-1-(2,2-diethoxyethyl)-3-(N'-(4-methylphenyl)ureido)indolin-2-one NMR (CDCl$_3$) δ: 8.79 (s, 1H), 7.40–6.80 (m, 14H), 4.74 (dd, J=4.4, 5.4 Hz, 1H), 3.98 (dd, J=5.4, 14.2 Hz, 1H), 3.80–3.35 (m, 5H), 2.98 (d, J=14.6 Hz, 1H), 2.72 (d, J=14.6 Hz, 1H), 2.19 (s, 3H), 1.11 (t, J=7.4 Hz, 3H), 1.09 (t, J=6.8 Hz, 3H).

Example 115

(RS)-1-(2,2-Diethoxyethyl)-3-((4-methoxyphenyl)aminocarbonylmethyl)-3-(N'-(4-methylphenyl)ureido)indolin-2-one NMR (CDCl$_3$) δ: 7.40–6.60 (m, 15H), 4.75 (dd, J=4.8, 5.8 Hz, 1H), 3.99 (dd, J=5.8, 14.1 Hz, 1H), 3.88–3.40 (m, 5H), 3.64 (s, 3H), 2.86 (d, J=15.2 Hz, 1H), 2.58 (d, J=15.2 Hz, 1H), 2.27 (s, 3H), 1.17 (t, J=6.8 Hz, 3H), 1.13 (t, J=7.4 Hz, 3H).

Example 116

(RS)-3-((3-Ethoxycarbonylpropyl)aminocarbonylmethyl)-1-(2,2-diethoxyethyl)-3-(N'-(4-methylphenyl)ureido)indolin-2-one NMR (CDCl$_3$) δ: 7.40–6.70 (m, 10H), 6.40 (br, t, J=5.7 Hz, 1H), 4.78 (dd, J=4.4, 6.3 Hz, 1H), 4.18–3.90 (m, 3H), 3.86–3.47 (m, 5H), 3.38–3.20 (m, 2H), 2.78 (d, J=14.2 Hz, 1H), 2.37 (d, J=14.2 Hz, 1H), 2.25 (s, 3H), 1.90–1.75 (m, 2H), 1.33–1.05 (m, 11H).

Example 117

(RS)-1-(2,2-Diethoxyethyl)-3-(methoxyaminocarbonylmethyl)-3-(N'-(4-methylphenyl)ureido)indolin-2-one NMR (CDCl$_3$) δ: 7.33–6.80 (m, 9H), 6.68 (s, 1H), 6.62 (s, 1H), 4.76 (dd, J=4.4, 5.8 Hz, 1H), 3.98 (dd, J=5.8, 14.2 Hz, 1H), 3.86–3.40 (m, 5H), 3.66 (s, 3H), 2.91 (d, J=15.0 Hz, 1H), 2.57 (d, J=15.0 Hz, 1H), 2.28 (s, 3H), 1.17 (t, J=6.8 Hz, 3H), 1.13 (t, J=6.8 Hz, 3H).

Example 118

(RS)-1-(2,2-Diethoxyethyl)-3-((4-methoxycarbonylmethylphenyl)aminocarbonylmethyl)-3-(N'-(4-methylphenyl)ureido)indolin-2-one NMR (CDCl$_3$) δ: 8.42 (s, 1H), 7.41 (d, J=8.4 Hz, 2H), 7.28–6.80 (m, 12H), 4.78 (dd, J=3.9, 5.7 Hz, 1H), 4.02 (dd, J=5.7, 14.3 Hz, 1H), 3.86–3.40 (m, 5H), 3.69 (s, 3H), 3.58 (s, 2H), 2.94 (d, J=14.6 Hz, 1H), 2.55 (d, J=14.6 Hz, 1H), 2.23 (s, 3H), 1.16 (t, J=7.0 Hz, 3H), 1.11 (t, J=6.8 Hz, 3H).

Example 119

(RS)-1-(2,2-Diethoxyethyl)-3-((2,2-diethoxyethyl)aminocarbonylmethyl)-3-(N'-(4-methyl-phenyl)ureido)indolin-2-one NMR (CDCl$_3$) δ: 7.35–6.81 (m, 9H), 6.80 (s, 1H), 6.20 (br, 1H), 4.77 (dd, J=4.4, 6.2 Hz, 1H), 4.49 (t, J=4.8 Hz, 1H), 4.00 (dd, J=6.2, 14.2 Hz, 1H), 3.84–3.20 (m, 11H), 2.85 (d, J=14.6 Hz, 1H), 2.30 (d, J=14.6 Hz, 1H), 2.24 (s, 3H), 1.30–0.95 (m, 12H).

Example 120

(RS)-1-(2,2-Diethoxyethyl)-3-((4-hexylphenyl) aminocarbonylmethyl)-3-(N'-(4-methylphenyl) ureido)indolin-2-one NMR (CDCl$_3$) δ: 8.28 (s, 1H), 7.36–6.75 (m, 14H), 4.76 (dd, J=4.3, 5.7 Hz, 1H), 3.99 (dd, J=5.7, 13.7 Hz, 1H), 3.85–3.40 (m, 5H), 2.96 (d, J=14.3 Hz, 1H), 2.59 (d, J=14.3 Hz, 1H), 2.53 (t, J=7.4 Hz, 2H), 2.22 (s, 3H), 1.70–1.42 (m, 2H), 1.42–0.97 (m, 12H), 0.87 (t, J=5.7 Hz, 3H).

Example 121

(RS)-1-(2,2-Diethoxyethyl)-3-(N'-(4-methylphenyl) ureido)-3-((4-nitrophenyl)aminocarbonylmethyl) indolin-2-one NMR (CDCl$_3$) δ: 9.45 (s, 1H), 8.05 (d, J=9.0 Hz, 2H), 7.58 (d, J=9.0 Hz, 2H), 7.38–7.15 (m, 3H), 7.10–6.80 (m, 7H), 4.77 (dd, J=4.4, 5.8 Hz, 1H), 4.01 (dd, J=5.8, 14.6 Hz, 1H), 3.79–3.40 (m, 5H), 3.06 (d, J=15.0 Hz, 1H), 2.80 (d, J=15.0 Hz, 1H), 2.20 (s, 3H), 1.14 (t, J=6.8 Hz, 3H), 1.10 (t, J=7.2 Hz, 3H).

Example 122

(RS)-1-(2,2-Diethoxyethyl)-3-((3,4-dimethylphenyl) aminocarbonylmethyl)-3-(N'-(4-methylphenyl) ureido)indolin-2-one NMR (CDCl$_3$) δ: 8.44 (s, 1H), 7.30–6.85 (m, 13H), 4.77 (dd, J=4.4, 5.7 Hz, 1H), 3.99 (dd, J=5.7, 14.9 Hz, 1H), 3.85–3.43 (m, 5H), 2.97 (d, J=15.2 Hz, 1H), 2.60 (d, J=15.2 Hz, 1H), 2.21 (s, 3H), 2.19 (s, 3H), 2.16 (s, 3H), 1.15 (t, J=6.8 Hz, 3H), 1.10 (t, J=6.8 Hz, 3H).

Example 123

(RS)-3-((3-Chlorophenyl)aminocarbonylmethyl)-1-(2,2-diethoxyethyl)-3-(N'-(4-methylphenyl)ureido) indolin-2-one NMR (CDCl$_3$) δ: 8.64 (s, 1H), 7.58 (s, 1H), 7.35–6.84 (m, 13H), 4.76 (dd, J=4.4, 5.7 Hz, 1H), 4.02 (dd, J=5.7, 13.7 Hz, 1H), 3.81–3.40 (m, 5H), 2.99 (d, J=14.6 Hz, 1H), 2.72 (d, J=14.6 Hz, 1H), 2.21 (s, 3H), 1.14 (t, J=6.8 Hz, 3H), 1.10 (t, J=6.8 Hz, 3H).

Example 124

(RS)-1-(2,2-Diethoxyethyl)-3-((4-fluorophenyl) aminocarbonylmethyl)-3-(N'-(4-methylphenyl) ureido)indolin-2-one NMR (CDCl$_3$) δ: 8.60 (s, 1H), 7.42–6.83 (m, 14H), 4.74 (dd, J=4.3, 5.7 Hz, 1H), 3.98(dd, J=5.7, 14.3 Hz, 1H), 3.80–3.40 (m, 5H), 2.95 (d, J=14.3 Hz, 1H), 2.67 (d, J=14.3 Hz, 1H), 2.21 (s, 3H), 1.14 (t, J=7.2 Hz, 3H), 1.10 (t, J=7.4 Hz, 3H).

Example 125

(RS)-3-((4-Aminophenyl)aminocarbonylmethyl)-1-(2,2-diethoxyethyl)-3-(N'-(4-methylphenyl)ureido) indolin-2-one NMR (CDCl$_3$) δ: 8.38 (s, 1H), 7.35–6.80 (m, 12H), 6.53 (d, J=8.2 Hz, 2H), 4.76 (dd, J=4.4, 5.9 Hz, 1H), 4.01 (dd, J=5.9, 13.7 Hz, 1H), 3.85–3.40 (m, 5H), 2.91 (d, J=14.6 Hz, 1H), 2.56 (d, J=14.6 Hz, 1H), 2.20–1.70 (br, 2H), 2.19 (s, 3H), 1.14 (t, J=7.0 Hz, 3H), 1.09 (t, J=7.4 Hz, 3H).

Example 126

(RS)-3-(Benzylaminocarbonylmethyl)-1-(2,2-diethoxyethyl)-3-(N'-(4-methylphenyl)ureido) indolin-2-one NMR (CDCl$_3$) δ: 7.40–6.84 (m, 15H), 6.63 (t, J=5.4 Hz, 1H), 4.75 (dd, J=4.4, 5.7 Hz, 1H), 4.33 (d, J=5.4 Hz, 2H), 3.98 (dd, J=5.7, 14.3 Hz, 1H), 3.84–3.39 (m, 5H), 2.86 (d, J=14.6 Hz, 1H), 2.44 (d, J=14.6 Hz, 1H), 2.22 (s, 3H), 1.13 (t, J=6.8 Hz, 3H), 1.08 (t, J=7.4 Hz, 3H).

Example 127

(RS)-1-(2,2-Diethoxyethyl)-3-((4-hydroxyphenyl) aminocarbonylmethyl)-3-(N'-(4-methylphenyl) ureido)indolin-2-one NMR (DMSO-d$_6$) δ: 9.72 (s, 1H), 9.09 (s, 1H), 9.07 (s, 1H), 8.13 (s, 1H), 7.67 (s, 1H), 7.33–6.83 (m, 9H), 6.68 (d, J=8.8 Hz, 1H), 4.81–4.69 (m, 1H), 3.88(dd, J=5.7, 14.3 Hz, 1H), 3.80–3.40 (m, 5H), 2.80 (d, J=14.0 Hz, 1H), 2.44 (d, J=14.0 Hz, 1H), 2.19 (s, 3H), 1.16 (t, J=7.4 Hz, 3H), 1.11 (t, J=7.4 Hz, 3H).

Example 128

(RS)-1-(2,2-Diethoxyethyl)-3-((4-trifluoromethylphenyl)aminocarbonylmethyl)-3-(N'-(4-methylphenyl)ureido)indolin-2-one NMR (CDCl$_3$) δ: 8.87 (s, 1H), 7.56 (dd, J=8.8 Hz, 2H), 7.48 (d, J=8.8 Hz, 2H), 7.27 (t, J=7.8 Hz, 2H), 7.18–6.85 (m, 8H), 4.77 (dd, J=4.6, 5.7 Hz, 1H), 4.01 (dd, J=5.7, 13.1 Hz, 1H), 3.83–3.45 (m, 5H), 2.99 (d, J=14.8 Hz, 1H), 2.71 (d, J=14.8 Hz, 1H), 2.22 (s, 3H), 1.15 (t, J=6.8 Hz, 3H), 1.10 (t, J=6.8 Hz, 3H).

Example 129

(RS)-1-(2,2-Diethoxyethyl)-3-((3-methoxyphenyl) aminocarbonylmethyl)-3-(N'-(4-methylphenyl) ureido)indolin-2-one NMR (CDCl$_3$) δ: 8.35–8.14 (m, 1H), 7.34–6.90 (m, 12H), 6.90–6.63 (m, 2H), 4.78 (dd, J=3.8, 5.7 Hz, 1H), 4.02 (dd, J=5.7, 13.7 Hz, 1H), 3.77 (s, 3H), 3.85–3.45 (m, 5H), 2.97 (d, J=14.2 Hz, 1H), 2.54 (d, J=14.2 Hz, 1H), 2.24 (s, 3H), 1.18 (t, J=6.8 Hz, 3H), 1.12 (t, J=7.2 Hz, 3H).

Example 130

(RS)-1-(2,2-Diethoxyethyl)-3-((4-(N,N-dimethylamino)phenyl)aminocarbonylmethyl)-3-(N'-(4-methylphenyl)ureido)indolin-2-one NMR (CDCl$_3$) δ: 8.31 (s, 1H), 7.33–6.85 (m, 12H), 6.61 (d, J=8.8 Hz, 2H), 4.78 (dd, J=3.9, 5.7 Hz, 1H), 4.00 (dd, J=5.7, 14.3 Hz, 1H), 3.85–3.40 (m, 5H), 2.94 (d, J=14.6 Hz, 1H), 2.89 (s, 6H), 2.55 (d, J=14.6 Hz, 1H), 2.22 (s, 3H), 1.16 (t, J=6.8 Hz, 3H), 1.11 (t, J=7.4 Hz, 3H).

Example 131

(RS)-1-(2,2-Diethoxyethyl)-3-((4-(N-trifluoromethylcarbonyl-N-methylamino)phenyl) aminocarbonylmethyl)-3-(N'-(4-methylphenyl) ureido)indolin-2-one NMR (CDCl$_3$) δ: 8.83 (s, 1H), 7.54 (d, J=8.6 Hz, 2H), 7.36–7.17 (m, 3H), 7.16–6.87 (m, 9H), 4.78 (dd, J=4.3, 5.9

Hz, 1H), 4.01 (dd, J=5.9 Hz, 14.2 Hz, 1H), 3.82–3.50 (m, 5H), 3.29 (s, 3H), 2.95 (d, J=14.8 Hz, 1H), 2.66 (d, J=14.8 Hz, 1H), 2.22 (s, 3H), 1.15 (t, J=6.9 Hz, 3H), 1.10 (t, J=6.9 Hz, 3H).

Example 132

(RS)-1-(2,2-Diethoxyethyl)-3-(N'-(4-methylphenyl) ureido)-3-((2-pyrimidinyl)aminocarbonylmethyl) indolin-2-one NMR (CDCl$_3$) δ: 8.42 (d, J=5.0 Hz, 2H), 7.79 (br, 1H), 7.46–6.80 (m, 11H), 4.84 (dd, J=4.4, 5.9 Hz, 1H), 4.04 (dd, J=5.9 Hz, 14.2 Hz, 1H), 3.88 (dd, J=4.4, 14.2 Hz, 1H), 3.81–3.47 (m, 4H), 3.16 (br, 2H), 2.20 (s, 3H), 1.18 (t, J=7.0 Hz, 3H), 1.14 (t, J=7.2 Hz, 3H).

Example 133

(RS)-1-(2,2-Diethoxyethyl)-3-(N'-(4-methylphenyl) ureido)-3-(phenylaminocarbonylmethyl)indolin-2-one NMR (CDCl$_3$) δ: 8.49 (s, 1H), 7.42 (d, J=7.8 Hz, 2H), 7.35–6.86 (m, 13H), 4.77 (dd, J=4.4, 5.9 Hz, 1H), 4.00 (dd, J=5.9, 14.1 Hz, 1H), 3.85–3.40 (m, 5H), 2.97 (d, J=14.6 Hz, 1H), 2.64 (d, J=14.6 Hz, 1H), 2.21 (s, 3H), 1.14 (t, J=7.3 Hz, 3H), 1.10 (t, J=7.3 Hz, 3H).

Example 134

(RS)-1-(2,2-Diethoxyethyl)-3-((4-(N,N-diethylamino)phenyl)aminocarbonylmethyl)-3-(N'-(4-methylphenyl)ureido)indolin-2-one NMR (CDCl$_3$) δ: 8.18 (s, 1H), 7.38–6.77 (m, 12H), 6.55 (d, J=9.4 Hz, 2H), 4.78 (dd, J=4.4, 5.8 Hz, 1H), 4.02 (dd, J=5.8 Hz, 14.2 Hz, 1H), 3.85–3.41 (m, 5H), 3.29 (q, J=6.8 Hz, 4H), 2.95 (d, J=14.6 Hz, 1H), 2.53 (d, J=14.6 Hz, 1H), 2.21 (s, 3H), 1.22–0.92 (m, 12H).

Example 135

(RS)-1-(2,2-Diethoxyethyl)-3-((4-trifluoromethylcarbonylamino)phenyl) aminocarbonylmethyl)-3-(N'-(4-methylphenyl) ureido)indolin-2-one NMR (CDCl$_3$) δ: 8.88 (s, 1H), 8.27 (s, 1H), 7.43–7.12 (m, 7H), 7.12–6.77 (m, 7H), 4.78 (dd, J=3.9, 5.8 Hz, 1H), 4.03 (dd, J=5.8 Hz, 14.6 Hz, 1H), 3.84–3.39 (m, 5H), 2.95 (d, J=14.8 Hz, 1H), 2.72 (d, J=14.8 Hz, 1H), 2.19 (s, 3H), 1.14 (t, J=7.0 Hz, 3H), 1.10 (t, J=6.8 Hz, 3H).

Example 136

(RS)-1-(2,2-Diethoxyethyl)-3-(((1-trifluoromethylcarbonyl)indolin-5-yl) aminocarbonylmethyl)-3-(N'-(4-methylphenyl) ureido)indolin-2-one NMR (CDCl$_3$) δ: 8.99 (s, 1H), 8.01 (d, J=8.3 Hz, 1H), 7.54 (s, 1H), 7.40–6.80 (m, 11H), 4.79 (dd, J=3.8, 5.9 Hz, 1H), 4.22–3.94 (m, 3H), 3.88–3.41 (m, 5H), 3.13–2.86 (m, 3H), 2.77 (d, J=15.1 Hz, 1H), 2.19 (s, 3H), 1.15 (t, J=6.8 Hz, 3H), 1.10 (t, J=6.8 Hz, 3H).

Example 137

(RS)-1-(2,2-Diethoxyethyl)-3-((5-indolylamino)) carbonylethyl)-3-(N'-(4-methylphenyl)ureido) indolin-2-one NMR (CDCl$_3$) δ: 8.72 (s, 1H), 8.27 (s, 1H), 7.58 (s, 1H), 7.46 (s, 1H), 7.33 (s, 1H), 7.24–6.72 (m, 11H), 6.32 (s, 1H), 4.79–4.67 (m, 1H), 3.99 (dd, J=5.5 Hz, 14.6 Hz, 1H), 3.84–3.38 (m, 5H), 2.87 (d, J=14.6 Hz, 1H), 2.49 (d, J=14.6 Hz, 1H), 2.13 (s, 3H), 1.08 (t, J=6.8 Hz, 3H), 1.05 (t, J=6.8 Hz, 3H).

Example 138

(RS)-1-(2,2-Diethoxyethyl)-3-(N'-(4-methylphenyl) ureido)-3-((5-methylpyrido-2-yl) aminocarbonylmethyl)indolin-2-one To a solution of 0.223 g of (RS)-1-(2,2-diethoxyethyl)-3-(hydroxycarbonylmethyl)-3-(N'-(4-methylphenyl)ureido) indolin-2-one in 15 ml of dichloromethane were added successively 0.140 g of 4-dimethylaminopyridine and 0.040 ml of thionyl chloride at 0° C., followed by stirring at 0° C. for 30 minutes. To the mixture were further added 0.070 g of 4-dimethylaminopyridine and 0.130 g of 6-amino-3-picoline at 0° C. The resulting mixture was stirred at room temperature for 1 hour, and then washed with an aqueous solution of sodium chloride. The organic layer was dried over anhydrous sodium sulfate and concentrated. The crude product was purified by silica gel column chromatography (hexane/ethyl acetate=2/1) to give 0.169 g (73%) of the title compound.

NMR (CDCl$_3$) δ: 9.01 (s, 1H), 7.98 (d, J=8.8 Hz, 1H), 7.93 (s, 1H), 7.46 (dd, J=2.6, 8.8 Hz, 1H), 7.30–6.87 (m, 10H), 4.77 (dd, J=4.4, 6.2 Hz, 1H), 3.97 (dd, J=6.2, 14.2 Hz, 1H), 3.87–3.42 (m, 5H), 3.06 (d, J=14.2 Hz, 1H), 2.57 (d, J=14.2 Hz, 1H), 2.25 (s, 3H), 2.23 (s, 3H), 1.14 (t, J=7.4 Hz, 3H), 1.11 (t, J=7.2 Hz, 3H).

EXAMPLES 139 TO 145

The following compounds were prepared in the same manner as in Example 138, except for using various amines in place of 6-amino-3-picoline used in Example 138.

Example 139

(RS)-3-((2-Chlorophenyl)aminocarbonylmethyl)-1-(2,2-diethoxyethyl)-3-(N'-(4-methylphenyl)ureido) indolin-2-one NMR (CDCl$_3$) δ: 8.15 (d, J=8.0 Hz, 1H), 7.89 (s, 1H), 7.35–6.85 (m, 13H), 4.78 (dd, J=4.4, 5.8 Hz, 1H), 4.02 (dd, J=5.8 Hz, 14.3 Hz, 1H), 3.85–3.40 (m, 5H), 3.10 (d, J=14.6 Hz, 1H), 2.62 (d, J=14.6 Hz, 1H), 2.24 (s, 3H), 1.14 (t, J=7.0 Hz, 3H), 1.12 (t, J=7.2 Hz, 3H).

Example 140

(RS)-1-(2,2-Diethoxyethyl)-3-(N'-(4-methylphenyl) ureido)-3-((4-pyridylamino)carbonylmethyl)indolin-2-one NMR (CDCl$_3$) δ: 9.68 (s, 1H), 8.32 (d, J=5.8 Hz, 2H), 7.73 (s, 1H), 7.45–6.80 (m, 11H), 4.77 (dd, J=4.6, 5.7 Hz, 1H), 4.02 (dd, J=5.7 Hz, 14.3 Hz, 1H), 3.85–3.40 (m, 5H), 2.99 (d, J=15.0 Hz, 1H), 2.74 (d, J=15.0 Hz, 1H), 2.20 (s, 3H), 1.14 (t, J=7.0 Hz, 3H), 1.10 (t, J=7.4 Hz, 3H).

Example 141

(RS)-1-(2,2-Diethoxyethyl)-3-((2-methoxyphenyl) aminocarbonylmethyl)-3-(N'-(4-methylphenyl) ureido)indolin-2-one NMR (CDCl$_3$) δ: 8.22 (dd, J=1.4 Hz, 7.8 Hz, 1H), 7.88 (s, 1H), 7.40–6.75 (m, 13H), 4.78 (dd, J=4.4, 5.8 Hz, 1H), 4.03

(dd, J=5.8 Hz, 13.7 Hz, 1H), 3.74 (s, 3H), 3.90–3.43 (m, 5H), 3.12 (d, J=14.6 Hz, 1H), 2.53 (d, J=14.6 Hz, 1H), 2.21 (s, 3H), 1.15 (t, J=7.4 Hz, 3H), 1.12 (t, J=6.8 Hz, 3H).

Example 142

(RS)-1-(2,2-Diethoxyethyl)-3-((2-hydroxy-4-methylphenyl)aminocarbonylmethyl)-3-(N'-(4-methylphenyl)ureido)indolin-2-one NMR (CDCl$_3$) δ: 8.57 (s, 1H), 8.65–8.20 (br, 1H), 7.32–7.15 (m, 3H), 7.15–6.79 (m, 8H), 6.73 (s, 1H), 6.57 (d, J=8.4 Hz, 1H), 4.73 (dd, J=4.9, 5.7 Hz, 1H), 4.01 (dd, J=5.7, 14.3 Hz, 1H), 3.80–3.43 (m, 5H), 2.87 (d, J=14.3 Hz, 1H), 2.72 (d, J=14.3 Hz, 1H), 2.21 (s, 3H), 2.19 (s, 3H), 1.11 (t, J=6.8 Hz, 3H), 1.08 (t, J=7.4 Hz, 3H).

Example 143

(RS)-1-(2,2-Diethoxyethyl)-3-((2-methoxypyrido-5-yl)aminocarbonylmethyl)-3-(N'-(4-methylphenyl)ureido)indolin-2-one NMR (CDCl$_3$) δ: 8.61 (s, 1H), 8.11 (d, J=2.4 Hz, 1H), 7.65 (dd, J=3.0 Hz, 8.8 Hz, 1H), 7.35–6.79 (m, 10H), 6.61 (d, J=8.8 Hz, 1H), 4.76 (dd, J=3.0, 5.7 Hz, 1H), 4.00 (dd, J=5.7 Hz, 14.3 Hz, 1H), 3.87 (s, 3H), 3.87–3.38 (m, 5H), 2.96 (d, J=14.3 Hz, 1H), 2.68 (d, J=14.3 Hz, 1H), 2.20 (s, 3H), 1.13 (t, J=7.2 Hz, 3H), 1.09 (t, J=7.0 Hz, 3H).

Example 144

(RS)-1-(2,2-Diethoxyethyl)-3-(N'-(4-methylphenyl)ureido)-3-((2-pyridyl)aminocarbonylmethyl)indolin-2-one NMR (CDCl$_3$) δ: 8.97 (brs, 1H), 8.14 (d, J=4.9 Hz, 1H), 8.08 (d, J=7.9 Hz, 1H), 7.65 (t, J=7.3 Hz, 1H), 7.35–6.85 (m, 11H), 4.77 (dd, J=4.3, 5.9 Hz, 1H), 3.99 (dd, J=5.9 Hz, 14.2 Hz, 1H), 3.90–3.47 (m, 5H), 3.10 (d, J=14.8 Hz, 1H), 2.61 (d, J=14.8 Hz, 1H), 2.23 (s, 3H), 1.14 (t, J=6.9 Hz, 3H), 1.11 (t, J=7.3 Hz, 3H).

Example 145

(RS)-1-(2,2-Diethoxyethyl)-3-(N'-(4-methylphenyl)ureido-3-((3-pyridyl)aminocarbonylmethyl)indolin-2-one NMR (CDCl$_3$) δ: 9.21 (s, 1H), 8.61 (d, J=2.6 Hz, 1H), 8.26 (d, J=4.6 Hz, 1H), 7.90 (d, J=7.9 Hz, 1H), 7.64 (s, 1H), 7.38–6.94 (m, 10H), 4.77 (dd, J=4.3, 5.9 Hz, 1H), 4.03 (dd, J=5.9 Hz, 14.5 Hz, 1H), 3.85–3.45 (m, 5H), 3.01 (d, J=14.8 Hz, 1H), 2.74 (d, J=14.8 Hz, 1H), 2.20 (s, 3H), 1.13 (t, J=6.9 Hz, 3H), 1.09 (t, J=7.3 Hz, 3H).

Example 146

(RS)-3-(Ethoxycarbonylmethyl)-1-(2,2-diethoxyethyl)-3-(N'-(3-methoxyphenyl)ureido)indolin-2-one The title compound was prepared in the same manner as in Example 107, except for starting with (RS)-1-(2,2-diethoxyethyl)-3-(N'-(3-methoxyphenyl)ureido)indolin-2-one in place of (RS)-1-(2,2-diethoxyethyl)-3-(N'-(4-methylphenyl)ureido)indolin-2-one used in Example 107.

NMR (CDCl$_3$) δ: 7.32–6.90 (m, 9H), 6.56 (dd, J=1.8, 8.2 Hz, 1H), 4.79–4.75 (m, 1H), 4.11 (q, J=6.3 Hz, 2H), 4.01 (dd, J=6.0, 14.2 Hz, 1H), 3.82–3.65 (m, 5H), 3.73 (s, 3H), 2.93 (d, J=15.2 Hz, 1H), 2.55 (d, J=15.2 Hz, 1H), 1.20–1.05 (m, 9H).

Example 147

(RS)-1-(2,2-Diethoxyethyl)-3-(hydroxycarbonylmethyl)-3-(N'-(3-methoxyphenyl)ureido)indolin-2-one The title compound was prepared in the same manner as in Example 108, except for starting with (RS)-3-(ethoxycarbonylmethyl)-1-(2,2-diethoxyethyl)-3-(N'-(3-methoxyphenyl)ureido)indolin-2-one in place of (RS)-3-(ethoxycarbonylmethyl)-1-(2,2-diethoxyethyl)-3-(N'-(4-methylphenyl)ureido)indolin-2-one as used in Example 108.

NMR (CDCl$_3$) δ: 7.85 (s, 1H), 7.29–7.20 (m, 3H), 7.06–6.92 (m, 5H), 6.69 (d, J=8.9 Hz, 1H), 6.48 (dd, J=2.2, 8.3 Hz, 1H), 4.77–4.74 (m, 1H), 4.04 (dd, J=6.1, 14.5 Hz, 1H), 3.79–3.49 (m, 5H), 3.61 (s, 3H), 2.90 (d, 15.8 Hz, 1H), 2.70 (d, 15.8 Hz, 1H), 1.17–1.08 (m, 6H).

Example 148

(RS)-1-(2,2-Diethoxyethyl)-3-((4-methoxyphenyl)aminocarbonylmethyl)-3-(N'-(3-methoxyphenyl)ureido)indolin-2-one To a solution of 0.50 g of (RS)-1-(2,2-diethoxyethyl)-3-(hydroxycarbonylmethyl)-3-(N'-(3-methoxyphenyl)ureido)indolin-2-one in 50 ml of dichloromethane were added successively 0.140 g of 4-dimethylaminopyridine and 0.090 ml of thionyl chloride at 0° C., followed by stirring at 0° C. for 30 minutes. To the mixture were further added 0.140 g of 4-dimethylaminopyridine and 0.190 g of 4-methoxyaniline at 0° C. The resulting mixture was stirred at room temperature for 1 hour, and then washed with an aqueous solution of sodium chloride. The organic layer was dried over anhydrous sodium sulfate and concentrated. The crude product was purified by silica gel column chromatography (hexane/ethyl acetate=2/1) to give 0.54 g (88%) of the title compound.

Rf=0.76 (dichloromethane/methanol=10/1)

NMR (CDCl$_3$) δ: 8.51 (s, 1H), 7.45–6.44 (m, 14H), 4.78 (dd, J=4.4, 5.9 Hz, 1H), 3.98 (dd, J=5.9, 14.2 Hz, 1H), 3.84–3.47 (m, 5H), 3.74 (s, 3H), 3.63 (s, 3H), 2.97 (d, J=14.8 Hz, 1H), 2.63 (d, J=14.8 Hz, 1H), 1.15 (t, J=6.9 Hz, 3H), 1.09 (t, J=6.9 Hz, 3H).

EXAMPLES 149 TO 158

The following compounds were prepared in the same manner as in Example 148, except for using various amines in place of 4-methoxyaniline used in Example 148.

Example 149

(RS)-3-((4-Chlorophenyl)aminocarbonylmethyl)-1-(2,2-diethoxyethyl)-3-(N'-(3-methoxyphenyl)ureido)indolin-2-one Rf=0.76 (dichloromethane/methanol=10/1)

NMR (CDCl$_3$) δ: 8.80 (s, 1H), 7.55 (s, 1H), 7.33–6.90 (m, 11H), 6.67 (d, J=9.2 Hz, 1H), 6.45 (dd, J=2.0, 8.2 Hz, 1H), 4.76 (dd, J=4.0, 5.6 Hz, 1H), 3.99 (dd, J=5.6, 14.2 Hz, 1H), 3.79–3.49 (m, 5H), 3.61 (s, 3H), 2.99 (d, J=14.8 Hz, 1H), 2.71 (d, J=14.8 Hz, 1H), 1.13 (t, J=6.9 Hz, 3H), 1.09 (t, J=6.9 Hz, 3H).

Example 150

(RS)-1-(2,2-Diethoxyethyl)-3-(N'-(3-methoxyphenyl)ureido)-3-((2-methylphenyl)aminocarbonylmethyl)indolin-2-one Rf=0.25 (dichloromethane/methanol=100/3)

NMR (CDCl$_3$) δ: 8.85 (s, 1H), 7.76 (s, 1H), 7.46–7.43 (m, 1H), 7.25–6.95 (m, 10H), 6.69 (d, J=7.9 Hz, 1H), 6.44 (d, J=8.3 Hz, 1H), 4.75 (dd, J=4.3, 5.9 Hz, 1H), 3.97 (dd, J=5.9, 14.5 Hz, 1H), 3.81–3.44 (m, 5H), 3.61 (s, 3H), 3.00 (d, J=14.9 Hz, 1H), 2.75 (d, J=14.9 Hz, 1H), 2.14 (s, 3H), 1.10 (t, J=6.6 Hz, 3H), 1.07 (t, J=6.6 Hz, 3H).

Example 151

(RS)-1-(2,2-Diethoxyethyl)-3-((3-methoxyphenyl)aminocarbonylmethyl)-3-(N'-(3-methoxyphenyl)ureido)indolin-2-one Rf=0.06 (dichloromethane/methanol=100/3)

NMR (CDCl$_3$) δ: 8.72 (s, 1H), 7.62 (s, 1H), 7.30–6.92 (m, 10H), 6.69 (d, J=9.2 Hz, 1H), 6.61 (dd, J=2.3, 8.2 Hz, 1H), 6.43 (dd, J=2.3, 7.9 Hz, 1H), 4.75 (dd, J=4.3, 5.9 Hz, 1H), 3.94 (dd, J=5.9, 14.2 Hz, 1H), 3.80–3.43 (m, 5H), 3.67 (s, 3H), 3.59 (s, 3H), 3.00 (d, J=14.9 Hz, 1H), 2.69 (d, J=14.9 Hz, 1H), 1.12 (t, J=6.9 Hz, 3H), 1.07 (t, J=6.9 Hz, 3H).

Example 152

(RS)-1-(2,2-Diethoxyethyl)-3-(N'-(3-methoxyphenyl)ureido)-3-((3-methylphenyl)aminocarbonylmethyl)indolin-2-one Rf=0.25 (dichloromethane/methanol=100/3)

NMR (CDCl$_3$) δ: 8.66 (s, 1H), 7.57 (s, 1H), 7.28–6.87 (m, 11H), 6.68 (d, J=7.9 Hz, 1H), 6.44 (d, J=8.2 Hz, 1H), 4.76 (dd, J=4.3, 5.9 Hz, 1H), 3.96 (dd, J=5.9, 14.5 Hz, 1H), 3.81–3.42 (m, 5H), 3.60 (s, 3H), 3.00 (d, J=14.9 Hz, 1H), 2.69 (d, J=14.9 Hz, 1H), 2.22 (s, 3H), 1.13 (t, J=6.9 Hz, 3H), 1.08 (t, J=6.9 Hz, 3H).

Example 153

(RS)-1-(2,2-Diethoxyethyl)-3-((2-methoxyphenyl)aminocarbonylmethyl)-3-(N'-(3-methoxyphenyl)ureido)indolin-2-one Rf=0.10 (dichloromethane/methanol=100/3)

NMR (CDCl$_3$) δ: 8.20 (d, J=7.9 Hz, 1H), 7.90 (s, 1H), 7.73 (s, 1H), 7.42 (s, 1H), 7.30 (d, J=7.3 Hz, 1H), 7.22 (t, J=8.2 Hz, 1H), 7.09–6.71 (m, 8H), 6.44 (d, J=6.6 Hz, 1H), 4.78 (dd, J=4.3, 5.9 Hz, 1H), 4.00 (dd, J=5.9, 14.2 Hz, 1H), 3.83–3.49 (m, 5H), 3.70 (s, 3H), 3.60 (s, 3H), 3.17 (d, J=14.5 Hz, 1H), 2.57 (d, J=14.5 Hz, 1H), 1.14 (t, J=6.9 Hz, 3H), 1.10 (t, J=6.9 Hz, 3H).

Example 154

(RS)-1-(2,2-Diethoxyethyl)-3-((4-fluorophenyl)aminocarbonylmethyl)-3-(N'-(3-methoxyphenyl)ureido)indolin-2-one Rf=0.16 (dichloromethane/methanol=100/3)

NMR (CDCl$_3$) δ: 8.70 (s, 1H), 7.65 (s, 1H), 7.31–6.84 (m, 11H), 6.68 (d, J=7.9 Hz, 1H), 6.44 (d, J=6.6 Hz, 1H), 4.75 (dd, J=4.3, 5.6 Hz, 1H), 3.96 (dd, J=5.6, 14.2 Hz, 1H), 3.80–3.45 (m, 5H), 3.59 (s, 3H), 3.00 (d, J=14.9 Hz, 1H), 2.73 (d, J=14.9 Hz, 1H), 1.11 (t, J=6.9 Hz, 3H), 1.07 (t, J=6.9 Hz, 3H).

Example 155

(RS)-1-(2,2-Diethoxyethyl)-3-(N'-(3-methoxyphenyl)ureido)-3-(n-propylaminocarbonylmethyl)indolin-2-one Rf=0.09 (dichloromethane/methanol=100/3)

NMR (CDCl$_3$) δ: 7.84 (s, 1H), 7.44 (s, 1H), 7.31–6.96 (m, 6H), 6.76 (d, J=8.6 Hz, 1H), 6.55 (t, J=5.6 Hz, 1H), 6.44 (dd, J=2.3, 8.3 Hz, 1H), 4.79 (dd, J=4.3, 6.3 Hz, 1H), 3.98 (dd, J=6.3, 14.2 Hz, 1H), 3.86–3.50 (m, 5H), 3.63 (s, 3H), 3.17–3.06 (m, 2H), 2.89 (d, J=14.5 Hz, 1H), 2.50 (d, J=14.5 Hz, 1H), 1.40 (m, 2H), 1.17 (t, J=7.3 Hz, 3H), 1.09 (t, J=6.9 Hz, 3H), 0.81 (t, J=7.3 Hz, 3H).

Example 156

(RS)-1-(2,2-Diethoxyethyl)-3-(N'-(3-methoxyphenyl)ureido)-3-((4-(N,N'-dimethylaminophenyl)aminocarbonylmethyl)indolin-2-one Rf=0.21 (dichloromethane/methanol=100/3)

NMR (CDCl$_3$) δ: 8.58 (s, 1H), 7.78 (s, 1H), 7.37 (s, 1H), 7.26–6.90 (m, 8H), 6.67 (d, J=7.9 Hz, 1H), 6.54 (d, J=8.9 Hz, 2H), 6.41 (d, J=9.9 Hz, 1H), 4.79–4.73 (m, 1H), 3.96 (dd, J=5.9, 14.2 Hz, 1H), 3.84–3.45 (m, 5H), 3.58 (s, 3H), 2.97 (d, J=14.5 Hz, 1H), 2.83 (s, 6H), 2.65 (d, J=14.5 Hz, 1H), 1.12 (t, J=6.9 Hz, 3H), 1.07 (t, J=6.9 Hz, 3H).

Example 157

(RS)-1-(2,2-Diethoxyethyl)-3-((4-methoxycarbonylphenyl)aminocarbonylmethyl)-3-(N'-(3-methoxyphenyl)ureido)indolin-2-one Rf=0.27 (dichloromethane/methanol=100/3)

NMR (CDCl$_3$) δ: 9.10 (s, 1H), 7.88 (s, 1H), 7.83 (d, J=8.6 Hz, 2H), 7.46 (d, J=8.6 Hz, 2H), 7.32–7.17 (m, 3H), 7.01–6.90 (m, 4H), 6.68 (d, J=7.9 Hz, 1H), 6.42 (dd, J=2.3, 8.3 Hz, 1H), 4.75 (dd, J=4.3, 5.9 Hz, 1H), 3.95 (dd, J=5.9, 14.2 Hz, 1H), 3.85 (s, 3H), 3.80–3.44 (m, 5H), 3.56 (s, 3H), 3.05 (d, J=15.2 Hz, 1H), 2.74 (d, J=15.2 Hz, 1H), 1.09 (t, J=6.9 Hz, 3H), 1.06 (t, J=6.9 Hz, 3H).

Example 158

(RS)-1-(2,2-Diethoxyethyl)-3-(N'-(3-methoxyphenyl)ureido)-3-((5-methylpyrido-2-yl)aminocarbonylmethyl)indolin-2-one Rf=0.24 (dichloromethane/methanol=100/3)

NMR (CDCl$_3$) δ: 9.48 (s, 1H), 7.93 (d, J=8.3 Hz, 1H), 7.79 (s, 1H), 7.73 (s, 1H), 7.41–6.90 (m, 8H), 6.71 (d, J=7.9 Hz, 1H), 6.46 (d, J=8.3 Hz, 1H), 4.78–4.75 (m, 1H), 3.90 (br, 2H), 3.72–3.45 (m, 4H), 3.62 (s, 3H), 3.10 (d, J=14.5 Hz, 1H), 2.61 (d, J=14.5 Hz, 1H), 2.21 (s, 3H), 1.13 (t, 7.3 Hz, 3H), 1.07 (t, 7.3 Hz, 3H).

Example 159

(RS)-1-(Formylmethyl)-3-(N'-(3-methoxyphenyl)ureido)-3-((4-methylphenyl)aminocarbonylmethyl)indolin-2-one To a solution of 1.61 g of (RS)-1-(2,2-diethoxyethyl)-3-(N'-(3-methoxyphenyl)ureido)-3-((4-methylphenyl)aminocarbonylmethyl)indolin-2-one in 40 ml of acetone were added 10 ml of water and 1 ml of concentrated hydrochloric acid, and the mixture was heated under reflux for 2 hours. The reaction mixture was poured into water, and the thus formed precipitate was collected by filtration and washed with ethyl ether to obtain 1.11 g (79%) of the title compound.

NMR (DMSO-$d_6$) δ: 10.06 (s, 1H), 9.66 (s, 1H), 9.32 (s, 1H), 7.75 (s, 1H), 7.44 (d, J=8.3 Hz, 2H), 7.28–6.82 (m, 8H), 6.82 (d, J=8.3 Hz, 1H), 6.44 (dd, J=2.0, 7.8 Hz, 1H), 4.77 (d, J=18.5 Hz, 1H), 4.60 (d, J=18.5 Hz, 1H), 3.66 (s, 3H), 2.89 (d, J=14.6 Hz, 1H), 2.60 (d, J=14.1 Hz, 1H), 2.26 (s, 3H).

Example 160

(RS)-3-(N'-(3-Methoxyphenyl)ureido)-1-(2-(N,N-dimethylamino)ethyl)-3-((4-methylphenyl)aminocarbonylmethyl)indolin-2-one To a solution of 0.386 g of (RS)-1-(formylmethyl)-3-(N'-(3-methoxyphenyl)ureido)-3-((4-methylphenyl)aminocarbonylmethyl)indolin-2-one in 50 ml of methanol was added 0.8 g of dimethylamine hydrochloride at room temperature, and 1.0 g of sodium cyanoborohydride was then added thereto. The mixture was stirred at room temperature for 1 day, followed by concentration. The concentrate was diluted with dichloromethane and washed with an aqueous solution of sodium chloride. The organic layer was dried over anhydrous sodium sulfate and concentrated. The crude product was washed with dichloromethane to afford 0.107 g (26%) of the title compound.

NMR (CDCl$_3$) δ: 10.21 (s, 1H), 9.26 (s, 1H), 7.62 (s, 1H), 7.32–6.84 (m, 10H), 6.79 (d, J=8.3 Hz, 1H), 6.44 (dd, J=1.9, 7.8 Hz, 1H), 3.94–3.59 (m, 2H), 3.65 (s, 3H), 2.82 (d, J=14.6 Hz, 1H), 2.62–2.08 (m, 3H), 2.25 (s, 9H).

Example 161

(RS)-1-(2,2-Diethoxyethyl)-3-((4-(N-methylamino)phenyl)aminocarbonylmethyl)-3-(N'-(4-methylphenyl)ureido)indolin-2-one To a solution of 0.475 g of (RS)-1-(2,2-diethoxyethyl)-3-((4-trifluoromethylcarbonyl-N-methylamino)phenyl)aminocarbonylmethyl)-3-(N'-(4-methylphenyl)ureido)indolin-2-one in 50 ml of methanol was added 10 ml of an aqueous solution of 0.50 g of potassium carbonate at room temperature, and the mixture was stirred for 1 day, followed by concentration. The residue was diluted with water and extracted with dichloromethane. The organic layer was dried over anhydrous sodium sulfate and concentrated. The crude product was recrystallized from chloroform to afford 0.26 g (65%) of the title compound.

NMR (DMSO-$d_6$) δ: 9.67 (s, 1H), 9.16 (s, 1H), 7.68 (s, 1H), 7.27–7.06 (m, 7H), 6.98–6.89 (m, 3H), 6.47 (d, J=8.8 Hz, 2H), 5.49 (q, J=5.9 Hz, 1H), 4.76–4.67 (m, 1H), 3.86 (dd, J=5.6, 13.8 Hz, 1H), 3.76–3.46 (m, 5H), 2.76 (d, J=14.2 Hz, 1H), 2.64 (d, J=5.9 Hz, 3H), 2.41 (d, J=14.2 Hz, 1H), 2.17 (s, 3H), 1.12 (t, J=6.9 Hz, 3H), 1.07 (t, J=5.0 Hz, 3H).

Example 162

(RS)-1-(2,2-Diethoxyethyl)-3-((5-indolinyl)aminocarbonylmethyl)-3-(N'-(4-methylphenyl)ureido)indolin-2-one The title compound was prepared in the same manner as in Example 161, except for starting with (RS)-1-(2,2-diethoxyethyl)-3-(((1-trifluoromethylcarbonyl)indolin-5-yl)aminocarbonylmethyl)-3-(N'-(4-methylphenyl)ureido)indolin-2-one in place of (RS)-1-(2,2-diethoxyethyl)-3-((4-(N-trifluoromethylcarbonyl-N-methylamino)phenyl)aminocarbonylmethyl)-3-(N'-(4-methylphenyl)ureido)indolin-2-one used in Example 161.

NMR (DMSO-$d_6$) δ: 9.67 (s, 1H), 9.15 (s, 1H), 7.68 (s, 1H), 7.36–6.86 (m, 10H), 6.41 (d, J=8.6 Hz, 1H), 5.35 (s, 1H), 4.77–4.67 (m, 1H), 3.85 (dd, J=5.9, 14.2 Hz, 1H), 3.76–3.24 (m, 7H), 2.87 (t, J=8.3 Hz, 2H), 2.75 (d, J=14.2 Hz, 1H), 2.41 (d, J=14.2 Hz, 1H), 2.17 (s, 3H), 1.11 (t, J=6.9 Hz, 3H), 1.07 (t, J=6.9 Hz, 3H).

Example 163

(RS)-1-(2,2-Diethoxyethyl)-3-((4-hydroxycarbonylphenyl)aminocarbonylmethyl)-3-(N'-(4-methylphenyl)ureido)indolin-2-one To a solution of 0.588 g of (RS)-1-(2,2-diethoxyethyl)-3-((4-methoxycarbonylphenyl)aminocarbonylmethyl)-3-(N'-(4-methylphenyl)ureido)indolin-2-one in 30 ml of methanol was added 5 ml of an aqueous solution of 0.20 g of potassium hydroxide (85%) at room temperature. The mixture was stirred for 1 day, followed by concentration. The concentrate was diluted with water, and washed with chloroform. The aqueous layer was adjusted to pH 2 with 2N hydrochloric acid and extracted with ethyl acetate. The organic layer was dried over anhydrous sodium sulfate and concentrated. The resulting crude product was purified by silica gel column chromatography (hexane/ethyl acetate 1/1) to give 0.56 g (98%) of the title compound.

NMR (DMSO-$d_6$) δ: 12.95–12.45 (br, 1H), 10.33 (s, 1H), 9.05 (s, 1H), 7.89 (d, J=8.4 Hz, 2H), 7.64 (d, J=8.4 Hz, 2H), 7.48 (s, 1H), 7.30–6.83 (m, 8H), 4.76–4.66 (m, 1H), 3.86 (dd, J=5.7, 13.7 Hz, 1H), 3.78–3.40 (m, 5H), 2.94 (d, J=14.6 Hz, 1H), 2.58 (d, J=14.6 Hz, 1H), 2.18 (s, 3H), 1.11 (t, J=6.8 Hz, 3H), 1.08 (t, J=6.8 Hz, 3H).

Example 164

(RS)-1-(2,2-Diethoxyethyl)-3-((4-hydroxycarbonylmethylphenyl)aminocarbonylmethyl)-3-(N'-(4-methylphenyl)ureido)indolin-2-one The title compound was prepared in the same manner in Example 163, except for starting with (RS)-1-(2,2-diethoxyethyl)-3-((4-methoxycarbonylmethylphenyl)aminocarbonylmethyl)-3-(N'-(4-methylphenyl)ureido)indolin-2-one in place of (RS)-1-(2,2-diethoxyethyl)-3-((4-methoxycarbonylphenyl)aminocarbonylmethyl)-3-(N'-(4-methylphenyl)ureido)indolin-2-one used in Example 163.

NMR (CDCl$_3$) δ: 8.73 (s, 1H), 7.55–7.37 (br, 1H), 7.32–6.77 (m, 14H), 4.85–4.74 (m, 1H), 4.08 (dd, J=5.7, 14.3 Hz, 1H), 3.85–3.35 (m, 7H), 2.95 (d, J=15.2 Hz, 1H), 2.64 (d, J=15.2 Hz, 1H), 2.17 (s, 3H), 1.15 (t, J=6.4 Hz, 3H), 1.11 (t, J=6.8 Hz, 3H).

Example 165

(RS)-1-(2,2-Diethoxyethyl)-3-(N'-(4-hydroxycarbonylphenyl)ureido)-3-((4-methylphenyl)aminocarbonylmethyl)indolin-2-one The title compound was prepared in the same manner as in Example 163, except for starting with (RS)-3-(N'-(4-ethoxycarbonylphenyl)ureido)-1(2,2-diethoxyethyl)-3-((4-methylphenyl)aminocarbonylmethyl)indolin-2-one in place of (RS)-1-(2,2-diethoxyethyl)-3-((4-methoxycarbonylphenyl)aminocarbonylmethyl)-3-(N'-(4-methylphenyl)ureido)indolin-2-one used in Example 163.

Rf=0.05 (n-hexane/ethyl acetate=1/1)

NMR (DMSO-d₆) δ: 9.97 (s, 1H), 9.64 (s, 1H), 7.84 (s, 1H), 7.75 (d, J=8.3 Hz, 2H), 7.44–6.89 (m, 1H), 4.75 (dd, J=4.0, 5.4 Hz, 1H), 3.88 (dd, J=5.4, 13.2 Hz, 1H), 3.74–3.22 (m, 5H), 2.86 (d, J=15.1 Hz, 1H), 2.51 (d, J=15.1 Hz, 1H), 2.27 (s, 3H), 1.14 (t, J=7.3 Hz, 3H), 1.10 (t, J=7.3 Hz, 3H).

Example 166

(RS)-3-(N'-(4-Aminophenyl)ureido)-1-(2,2-diethoxyethyl)-3-((4-methylphenyl)aminocarbonylmethyl)indolin-2-one A suspension of 0.62 g of (RS)-1-(2,2-diethoxyethyl)-3-((4-methylphenyl)aminocarbonylmethyl)-3-(N'-(4-nitrophenyl)ureido)indolin-2-one and 20 mg of 5% Pd/C in 100 ml of ethanol was stirred at room temperature for 12 hours under a hydrogen atmosphere. The reaction mixture was filtered through Cerite, and the filtrate was concentrated. The residue was purified by silica gel column chromatography (hexane/ethyl acetate=1/1) to give 0.33 g (57%) of the title compound.

NMR (CDCl₃) δ: 8.31 (s, 1H), 7.33–6.94 (m, 11H), 6.62 (s, 1H), 6.50 (d, J=8.3 Hz, 2H), 4.75 (dd, J=4.4, 5.9 Hz, 1H), 4.00 (dd, J=5.9, 14.1 Hz, 1H), 3.79–3.52 (m, 7H), 2.92 (d, J=14.6 Hz, 1H), 2.51 (d, J=14.6 Hz, 1H), 2.30 (s, 3H), 1.16 (t, J=7.3 Hz, 3H), 1.10 (t, J=7.3 Hz, 3H).

Example 167

(RS)-1-(2,2-Diethoxyethyl)-3-(N'-(4-dimethylaminophenyl)ureido-3-((4-methylphenyl)aminocarbonylmethyl)indolin-2-one To a solution of 0.148 g of (RS)-3-(N'-(4-aminophenyl)ureido)-1-(2,2-diethoxyethyl)-3-((4-methylphenyl)aminocarbonylmethyl)indolin-2-one in 20 ml of methanol were added successively 0.1 ml of a formalin aqueous solution and 0.104 g of sodium cyanoborohydride. The mixture was neutralized with 2N hydrochloric acid, and Molecular Sieves 4A was added thereto, followed by stirring at room temperature for 3 hours. The reaction mixture was filtered through Cerite, and the filtrate was concentrated. The concentrate was diluted with ethyl acetate and washed with a saturated aqueous sodium hydrogencarbonate. The organic layer was dried over anhydrous sodium sulfate and concentrated. The resulting crude product was purified by silica gel column chromatography (hexane/ethyl acetate=1/1) to give 0.120 g (77%) of the title compound.

Rf=0.11 (hexane/ethyl acetate=1/1)

NMR (CDCl₃) δ: 8.32 (s, 1H), 7.35–6.54 (m, 13H), 6.41 (s, 1H), 4.76 (dd, J=3.9, 6.3 Hz, 1H), 3.99 (dd, J=6.3, 13.7 Hz, 1H), 3.81–3.53 (m, 5H), 2.91 (d, J=15.1 Hz, 1H), 2.89 (s, 6H), 2.51 (d, J=15.1 Hz, 1H), 2.31 (s, 3H), 1.16 (t, J=6.3 Hz, 3H), 1.11 (t, J=6.3 Hz, 3H).

EXAMPLES 168 TO 170

The following compounds were prepared in the same manner as in Example 71, except for using (RS)-1-(2,2-diethoxyethyl)-3-(N'-(4-methylphenyl)ureido)indolin-2-one, used in Example 71, with the (4-methylphenyl)ureido moiety replaced with various substituted ureides as a starting material and replacing N-p-tolyl-2-bromoacetamide used in Example 71 with various bromoacetamide derivatives as a reactant.

Example 168

(RS)-3-((4-Chlorophenyl)aminocarbonylmethyl)-3-(N'-(4-chlorophenyl)ureido)-1-(2,2-diethoxyethyl)indolin-2-one Rf=0.29 (n-hexane/ethyl acetate=1/1)

NMR (CDCl₃) δ: 8.51 (s, 1H), 7.44–7.00 (m, 14H), 4.78 (dd, J=4.9, 5.4 Hz, 1H), 4.04 (dd, J=5.4, 14.2 Hz, 1H), 3.83–3.48 (m, 5H), 2.99 (d, J=14.6 Hz, 1H), 2.68 (d, J=14.6 Hz, 1H), 2.00–1.08 (m, 6H).

Example 169

(RS)-3-((4-Chlorophenyl)aminocarbonylmethyl)-1-(2,2-diethoxyethyl)-3-(N'-(4-methoxyphenyl)ureido)indolin-2-one NMR (DMSO-d₆) δ: 10.14 (s, 1H), 8.98 (s, 1H), 7.57–6.70 (m, 13H), 4.72 (dd, J=4.3, 5.9 Hz, 1H), 3.84 (dd, J=5.9, 14.4 Hz, 1H), 3.71–3.50 (m, 5H), 3.66 (s, 3H), 2.88 (d, J=14.8 Hz, 1H), 2.52 (d, J=14.8 Hz, 1H), 1.11 (t, J=7.8 Hz, 3H), 1.08 (t, J=7.3 Hz, 3H).

Example 170

(RS)-1-(2,2-Diethoxyethyl)-3-((4-fluorophenyl)aminocarbonylmethyl)-3-(N'-(4-fluorophenyl)ureido)indolin-2-one NMR (CDCl₃) δ: 8.40 (s, 1H), 7.42–6.78 (m, 14H), 4.78 (dd, J=4.3, 5.9 Hz, 1H), 4.02 (dd, J=5.9, 14.5 Hz, 1H), 3.81–3.52 (m, 5H), 2.98 (d, J=14.5 Hz, 1H), 2.63 (d, J=14.5 Hz, 1H), 1.17 (t, J=6.9 Hz, 3H), 1.12 (t, J=6.9 Hz, 3H).

REFERENCE EXAMPLE 26

L-Menthyl Bromoacetate and D-Menthyl Bromoacetate

To a solution of 83.4 g of bromoacetic acid and 78.1 g of L- (or D-)menthol in 1 2 of toluene was added 300 mg of p-toluenesulfonic acid, and the mixture was refluxed for 6 hours while azeotropically removing produced water together with toluene. The reaction mixture was washed with saturated aqueous sodium hydrogencarbonate, and the organic layer was dried over anhydrous sodium sulfate and concentrated. The residue was distilled under reduced pressure to obtain 128 g (93%) of the titled compound.

NMR (CDCl₃) δ: 4.73 (dt, J=5, 10 Hz, 1H), 3.79 (s, 2H), 2.20–0.80 (m, 9H), 0.89 (d, J=7 Hz, 6H), 0.79 (d, J=7 Hz, 3H).

Example 171

3-(RS)-1-(2,2-Diethoxyethyl)-3-(L-menthoxy)carbonylmethyl-3-(N'-(4-methylphenyl)ureido)indolin-2-one and Single Diastereomer of 1-(2,2-Diethoxyethyl)-3-(L-menthoxy)carbonylmethyl-3-(N'-(4-methylphenyl)ureido)indolin-2-one (HPLC second fraction)

3-(RS)-1-(2,2-Diethoxyethyl)-3-(L-menthoxy)carbonylmethyl-3-(N'-(4-methylphenyl)ureido)indolin-2-one was prepared in the same manner as in Example 71, except for using L-menthyl bromoacetate as a reactant in place of N-p-tolyl-2-bromoacetamide used in Example 71. The product was analyzed by high performance liquid chromatography.

HPLC Conditions:

Column: YMC-Pack CN A-514 (6.0 mm (diameter)×30 cm)

Developing solvent: hexane/isopropyl alcohol=100/1

Flow rate: 1.0 ml/min

Detection: UV 254 nm

First fraction: 53 parts (retention time=38 min)

Second fraction: 47 parts (retention time=42 min)

The diastereomeric mixture was recrystallized twice from diisopropyl ether to give a single diastereomer of 1-(2,2-diethoxyethyl)-3-(L-menthoxy)carbonylmethyl-3-(N'-(4-methylphenyl)ureido)indolin-2-one as needles.

NMR (CDCl$_3$) δ: 7.33–7.18 (m, 3H), 7.18–6.91 (m, 5H), 6.87 (s, 2H), 4.76 (dd, J=4.4, 5.5 Hz, 1H), 4.69 (dt, J=3.8, 10.8 Hz, 1H), 3.97 (dd, J=5.5, 13.1 Hz, 1H), 3.88–3.45 (m, 5H), 2.96 (d, J=13.2 Hz, 1H), 2.51 (d, J=13.2 Hz, 1H), 2.26 (s, 3H), 1.88–0.99 (m, 9H), 1.16 (t, J=7.0 Hz, 3H), 1.12 (t, J=7.4 Hz, 3H), 0.88 (d, J=6.2 Hz, 3H), 0.78 (d, J=7.4 Hz, 3H), 0.70 (d, J=6.8 Hz, 3H).

The product was analyzed by high performance liquid chromatography.

HPLC Conditions:

Column: YMC-Pack CN A-514 (6.0 mm (diameter)×30 cm)

Developing solvent: hexane/isopropyl alcohol=100/1

Flow rate: 1.0 ml/min

Detection: UV 254 nm

Fraction : retention time=42 min

Example 172

Single Diastereomer of 1-(2,2-Diethoxyethyl)-3-(L-menthoxy)carbonylmethyl-3-(N'-(4-methylphenyl)ureido)indolin-2-one (HPLC first fraction)

To a solution of 10.4 g of (RS)-1-(2,2-diethoxyethyl)-3-(N'-(4-methylphenyl)ureido)indolin-2-one in 500 ml of dry tetrahydrofuran was added slowly 52.5 ml of a 0.5M solution of lithium t-butoxide (prepared from n-butyl lithium and t-butanol) in dry tetrahydrofuran at room temperature under a nitrogen atmosphere, and the mixture was stirred at that temperature for 30 minutes. To the mixture was added dropwise a solution of 8.10 g of L-menthyl bromoacetate in 30 ml of dry tetrahydrofuran at 0° C., followed by stirring at 0° C. for 8 hours. The reaction mixture was poured into an aqueous solution of sodium chloride and extracted with ethyl acetate. The organic layer was dried over anhydrous sodium sulfate and concentrated. The residue was purified by silica gel column chromatography (hexane/ethyl acetate=3/1) and then recrystallized from methanolic water to afford 7.55 g (48%) of the title compound.

HPLC Conditions:

Column: YMC-Pack CN A-514 (6.0 mm (diameter)×30 cm)

Developing solvent: hexane/isopropyl alcohol=100/1

Flow rate: 1.0 ml/min

Detection: UV 254 nm

Fraction: retention time=38 min

Rf=0.44 (hexane/ethyl acetate=2/1)

NMR (CDCl$_3$) δ: 7.41–6.91 (m, 8H), 6.88 (s, 1H), 6.73 (s, 1H), 4.75 (dd, J=4.6, 5.7 Hz, 1H), 4.64 (dt, J=4.1, 11.1 Hz, 1H), 3.95 (dd, J=5.7, 14.6 Hz, 1H), 3.89–3.45 (m, 5H), 3.03 (d, J=15.1 Hz, 1H), 2.61 (d, J=15.1 Hz, 1H), 2.26 (s, 3H), 1.98–1.80 (br, 1H), 1.80–1.55 (br, 3H), 1.55–1.30 (br, 1H), 1.30–0.75 (br, 4H), 1.17 (t, J=6.8 Hz, 3H), 1.11 (t, J=7.0 Hz, 3H), 0.88 (d, J=6.5 Hz, 3H), 0.83 (d, J=7.0 Hz, 3H), 0.64 (d, J=6.8 Hz, 3H).

Example 173

Single Diastereomer of 1-(2,2-Diethoxyethyl)-3-(D-menthoxy)carbonylmethyl-3-(N'-(4-methylphenyl)ureido)indolin-2-one (HPLC first fraction)

The title compound was prepared in the same manner as in Example 172, except for replacing L-menthyl bromoacetate used in Example 172 with D-menthyl bromoacetate.

HPLC Conditions:

Column: YMC-Pack CN A-514 (6.0 mm (diameter)×30 cm)

Developing solvent: hexane/isopropyl alcohol=100/1

Flow rate: 1.0 ml/min

Detection: UV 254 nm

Retention time: 38 min

Rf=0.44 (hexane/ethyl acetate=2/1)

NMR (CDCl$_3$) δ: 7.41–6.91 (m, 8H), 6.88 (s, 1H), 6.73 (s, 1H), 4.75 (dd, J=4.6, 5.7 Hz, 1H), 4.64 (dt, J=4.1, 11.1 Hz, 1H), 3.95 (dd, J=5.7, 14.6 Hz, 1H), 3.89–3.45 (m, 5H), 3.03 (d, J=15.1 Hz, 1H), 2.61 (d, J=15.1 Hz, 1H), 2.26 (s, 3H), 1.98–1.80 (br, 1H), 1.80–1.55 (br, 3H), 1.55–1.30 (br, 1H), 1.30–0.75 (br, 4H), 1.17 (t, J=6.8 Hz, 3H), 1.11 (t, J=7.0 Hz, 3H), 0.88 (d, J=6.5 Hz, 3H), 0.83 (d, J=7.0 Hz, 3H), 0.64 (d, J=6.8 Hz, 3H).

Example 174

(+)-1-(2,2-Diethoxyethyl)-3-(4-methylphenyl)aminocarbonylmethyl-3-(N'-(4-methylphenyl)ureido)indolin-2-one (1) (+)-1-(2,2-Diethoxyethyl)-3-hydroxycarbonylmethyl-3-(N'-(4-methylphenyl)ureido)indolin-2-one To a solution of 5.30 g of 3-(+)-1-(2,2-diethoxyethyl)-3-(L-menthoxy)carbonylmethyl-3-(N'-(4-methylphenyl)ureido)indolin-2-one in 150 ml of methanol was added 30 ml of an aqueous solution of 1.00 g of potassium hydroxide (85%) at room temperature. The mixture was refluxed for 3 hours and concentrated. To the residue was added water, and the mixture was washed with chloroform. The aqueous layer was adjusted to pH 2 with 2N hydrochloric acid and extracted with ethyl acetate. The organic layer was washed with an aqueous solution of sodium chloride, dried over anhydrous sodium sulfate, and concentrated to obtain 2.8 g of the title compound.

NMR (CDCl$_3$) δ: 7.74 (s, 1H), 7.35–6.70 (m, 10H), 4.73 (dd, J=4.4, 5.9 Hz, 1H), 4.01 (dd, J=5.9, 14.6 Hz, 1H), 3.86–3.38 (m, 5H), 2.90 (d, J=15.9 Hz, 1H), 2.65 (d, J=15.9 Hz, 1H), 2.18 (s, 3H), 1.13 (t, J=6.8 Hz, 3H), 1.08 (t, J=6.8 Hz, 3H).

(2) (+)-1-(2,2-Diethoxyethyl)-3-(4-methylphenyl)aminocarbonylmethyl-3-(N'-(4-methylphenyl)ureido)indolin-2-one In 100 ml of dichloromethane was dissolved 2.8 g of (+)-1-(2,2-diethoxyethyl)-3-hydroxycarbonylmethyl-3-(N'-(4-methylphenyl)ureido)indolin-2-one, and 1.20 g of 4-dimethylaminopyridine, 1.90 g of 1-ethyl-3-(3-dimethylaminopropyl)carbodiimide hydrochloride, and 1.10 g of p-toluidine were successively added thereto. The mixture was stirred for 18 hours and concentrated. The concentrate was diluted with ethyl acetate, washed successively with dilute hydrochloric acid and saturated aqueous sodium hydrogencarbonate. The organic layer was dried over anhydrous sodium sulfate, and concentrated. The crude product was purified by silica gel column chromatography (hexane/ethyl acetate=2/1) to yield 3.90 g (81%) of the title compound as a white powder. The resulting compound was found to be optically pure as analyzed by high performance liquid chromatography using an optically active column (CHIRALCEL OD, produced by Daicel Chemical Industries, Ltd.).

Rf=0.21 (hexane/ethyl acetate=2/1)

NMR (CDCl$_3$) δ: 8.33 (s, 1H), 7.33–6.91 (m, 14H), 4.77 (dd, J=4.4, 5.6 Hz, 1H), 4.03 (dd, J=5.6, 14.1 Hz, 1H), 3.82–3.48 (m, 5H), 2.97 (d, J=14.6 Hz, 1H), 2.57 (d, J=14.6 Hz, 1H), 2.30 (s, 3H), 2.22 (s, 3H), 1.16 (t, J=6.8 Hz, 3H), 1.11 (t, J=6.8 Hz, 1H).

$[\alpha]_D^{25}$=27.9° (c=3.05, CHCl$_3$)

Example 175

(−)-1-(2,2-Diethoxyethyl)-3-(4-methylphenyl) aminocarbonylmethyl-3-(N'-(4-methylphenyl) ureido)indolin-2-one To a solution of 1.26 g of a single diastereomer of 1-(2,2-diethoxyethyl)-3-(L-menthoxy)carbonylmethyl-3-(N'-(4-methylphenyl)ureido)indolin-2-one (HPLC first fraction) in 20 ml of ethanol was added 10 ml of an aqueous solution of 0.07 g of potassium hydroxide (85%) at room temperature, and the mixture was stirred at 70° C. for 1 hour, followed by concentration. Water was added to the residue, and the mixture was washed with chloroform. The aqueous layer was adjusted to pH 2 by addition of 2N hydrochloric acid and extracted with ethyl acetate. The organic layer was dried over anhydrous sodium sulfate and concentrated to give 0.88 g of (−)-1-(2,2-diethoxyethyl)-3-hydroxycarbonylmethyl-3-(N'-(4-methylphenyl)ureido) indolin-2-one. The resulting product was dissolved in 50 ml of dichloromethane, and 0.52 g of 1-ethyl-3-(3-dimethylaminopropyl)carbodiimide hydrochloride and 0.29 g of p-toluidine were successively added thereto. The mixture was stirred for 18 hours and diluted with ethyl acetate, washed successively with dilute hydrochloric acid and saturated aqueous sodium hydrogencarbonate. The organic layer was dried over anhydrous sodium sulfate, and concentrated. The resulting crude product was purified by silica gel column chromatography (hexane/ethyl acetate=2/1) to give 0.90 g (90%) of the title compound as a white powder. The resulting compound was found to be optically pure as analyzed by high performance liquid chromatography using an optically active column (CHIRALCEL OD, produced by Daicel Chemical Industries, Ltd.). The Rf and NMR data were equal to those of the compound of Example 174.

$[\alpha]_D^{25}$=−27.6° C. (c=1.00, CHCl$_3$)

EXAMPLES 176 TO 181

The following compounds were prepared in the same manner as in Example 174, except for replacing p-toluidine used in Example 174 with various amines or alcohols as a reactant.

Example 176

(+)-1-(2,2-Diethoxyethyl)-3-(4-iodophenyl) aminocarbonylmethyl-3-(N'-(4-methylphenyl) ureido)indolin-2-one NMR (CDCl$_3$) δ: 8.60 (s, 1H), 7.55 (d, J=8.8 Hz, 2H), 7.32–6.94 (m, 11H), 6.84 (s, 1H), 4.77 (dd, J=4.4, 6.3 Hz, 1H), 4.00 (dd, J=6.3, 10.4 Hz, 1H), 3.82–3.46 (m, 5H), 2.96 (d, J=14.8 Hz, 1H), 2.65 (d, J=14.8 Hz, 1H), 2.23 (s, 3H), 1.20–1.07 (m, 6H).

Example 177

(+)-1-(2,2-Diethoxyethyl)-3-(2-bromoethoxy) carbonylmethyl-3-(N'-(4-methylphenyl)ureido) indolin-2-one Rf=0.14 (n-hexane/ethyl acetate=2/1)

NMR (CDCl$_3$) δ: 7.31–7.22 (m, 2H), 7.16–6.98 (m, 6H), 6.61 (s, 1H), 6.52 (s, 1H), 4.73 (dd, J=4.9, 5.9 Hz, 1H), 4.38 (t, J=6.3 Hz, 2H), 3.97 (dd, J=5.9, 8.3 Hz, 1H), 3.84–3.51 (m, 5H), 3.42 (t, J=6.3 Hz, 2H), 2.28 (s, 3H), 1.17 (t, J=7.3 Hz, 3H), 1.13 (t, J=7.8 Hz, 3H).

MS (m/e): 563, 561 (M$^+$), 517, 515, 438, 158, 103

Example 178

(+)-1-(2,2-Diethoxyethyl)-3-(2-iodoethoxy) carbonylmethyl-3-(N'-(4-methylphenyl)ureido) indolin-2-one Rf=0.14 (n-hexane/ethyl acetate=2/1)

NMR (CDCl$_3$) δ: 7.31–6.98 (m, 8H), 6.50 (s, 2H), 4.75 (dd, J=4.9, 5.8 Hz, 1H), 4.34 (dt, J=1.5, 6.9 Hz, 2H), 3.96 (dd, J=5.8H, 14.2 Hz, 1H), 3.85–3.52 (m, 5H), 3.19 (t, J=6.9 Hz, 2H), 2.93 (d, J=15.1 Hz, 1H), 2.64 (d, J=15.1 Hz, 1H), 2.29 (s, 3H), 1.17 (t, J=7.3 Hz, 3H), 1.13 (t, J=7.3 Hz, 3H).

MS (m/e): 609 (M$^+$), 563, 535, 414, 103

$[\alpha]_D^{25}$=+8.6° (c=1.00, CHCl$_3$)

Example 179

(+)-1-(2,2-Diethoxyethyl)-3-(N'-(4-methylphenyl) ureido)-3-(5-methylpyrido-2-yl) aminocarbonylmethyl)indolin-2-one The NMR data were equal to those of the compound of Example 138.

$[\alpha]_D^{25}$=+53.76° (c=1.09, CHCl$_3$)

Example 180

(+)-1-(2,2-Diethoxyethyl)-3-((4-(N,N-dimethylamino)phenyl)aminocarbonylmethyl)-3-(N'-(4-methylphenyl)ureido)indolin-2-one The NMR data were equal to those of the compound of Example 130.

$[\alpha]_D^{25}$=+55.09° (c=1.02, CHCl$_3$)

Example 181

(+)-1-(2,2-Diethoxyethyl)-3-((2-methoxypyrido-5-yl)aminocarbonylmethyl)-3-(N'-(4-methylphenyl) ureido)indolin-2-one The NMR data were equal to those of the compound of Example 143.

$[\alpha]_D^{25}$=+22.54° (c=1.02, CHCl$_3$)

EXAMPLES 182 TO 184

The following compounds were prepared in the same manner as in Example 175, except for using various amines as a reactant in place of p-toluidine used in Example 175.

Example 182

(−)-1-(2,2-Diethoxyethyl)-3-(N'-(4-methylphenyl)
ureido)-3-((5-methylpyrido-2-yl)
aminocarbonylmethyl)indolin-2-one The NMR data were equal to those of the compound of Example 138.

$[\alpha]_D^{25}$=−58.83° (c=1.03, CHCl$_3$)

Example 183

(−)-1-(2,2-Diethoxyethyl)-3-((4-(N,N-
dimethylamino)phenyl)aminocarbonylmethyl)-3-(N'-
(4-methylphenyl)ureido)indolin-2-one The NMR data were equal to those of the compound of Example 130.

$[\alpha]_D^{25}$=−60.91° (c=1.06, CHCl$_3$)

Example 184

(−)-1-(2,2-Diethoxyethyl)-3-((2-methoxypyrido-5-
yl)aminocarbonylmethyl)-3-(N'-(4-methylphenyl)
ureido)indolin-2-one The NMR data were equal to those of the compound of Example 143.

$[\alpha]_D^{25}$=−25.19° (c=1.04, CHCl$_3$)

Example 185

(3RS)-1-(2,2-Diethoxyethyl)-3-(L-menthoxy)
carbonylmethyl-3-(N'-(3-methoxyphenyl)ureido)
indolin-2-one To a solution of 0.207 g of (RS)-1-(2,2-diethoxyethyl)-3-(N'-(3-methoxyphenyl)ureido)indolin-2-one in 4 ml of dry dimethyl sulfoxide was added 0.5 ml of a 1M solution of potassium t-butoxide in dry dimethyl sulfoxide at room temperature under a nitrogen atmosphere. After stirring the mixture for 30 minutes, a solution of 0.166 g of L-menthyl bromoacetate in 2 ml of dry dimethyl sulfoxide was added thereto dropwise, followed by stirring at that temperature for 30 minutes. The reaction mixture was poured into an aqueous solution of sodium chloride and extracted with ethyl ether. The ethyl ether layer was dried over anhydrous magnesium sulfate and concentrated. The residue was purified by silica gel column chromatography (hexane/ethyl acetate=3/1) to give 0.170 g (56%) of the title compound. As a result of analysis by high performance liquid chromatography, the product was found to consist of both diastereomers at a ratio of approximately 1:1.

HPLC Conditions:

Column: YMC-Pack CN A-514 (6.0 mm (diameter)×30 cm)

Developing solvent: hexane/isopropyl alcohol=100/1

Flow rate: 1.0 ml/min

Detection: UV 254 nm

Fractions: 56 parts (retention time=47 min) 44 parts (retention time=52 min)

Rf=0.36 (hexane/ethyl acetate=2/1)

NMR (CHCl$_3$) δ: 7.30–7.20 (m, 2H), 7.16–6.92 (m, 5H), 6.79–6.75 (m, 2H), 6.57–6.52 (m, 1H), 4.80–4.75 (m, 1H), 4.72–4.62 (m, 1H), 3.99–3.51 (m, 6H), 3.71 (s, 3H), 3.01 (d, J=14.8 Hz, 0.5H), 2.96 (d, J=15.2 Hz, 0.5H), 2.62 (d, J=15.2 Hz, 0.5H), 2.54 (d, J=14.8 Hz, 0.5H), 1.83–1.71 (br, 1H), 1.65–1.59 (m, 4H), 1.42–0.57 (m, 3H), 1.21–1.09 (m, 6H), 0.89 (d, J=6.9 Hz, 1.5H), 0.88 (d, J=6.9 Hz, 1.5H), 0.82 (d, J=6.9 Hz, 1.5H), 0.77 (d, J=6.9 Hz, 1.5H), 0.70 (d, J=6.9 Hz, 1.5H), 0.64 (d, J=6.9 Hz, 1.5H).

Example 186

Single Diastereomer of 1-(2,2-Diethoxyethyl)-3-(L-
menthoxy)carbonylmethyl-3-(N'-(3-methoxyphenyl)
ureido)indolin-2-one (HPLC first fraction)

The same procedure of Example 172 was repeated except for using (RS)-1-(2,2-diethoxyethyl)-3-(N'-(3-methoxyphenyl)ureido)indolin-2-one as a starting material. The crude product was recrystallized from isopropyl ether to obtain the title compound as needles in a 32% yield. As a result of high performance liquid chromatography analysis, the product was confirmed to consist of a single diastereomer.

HPLC Conditions:

Column: YMC-Pack CN A-514 (6.0 mm (diameter)×30 cm)

Developing solvent: hexane/isopropyl alcohol=100/1

Flow rate: 1.0 ml/min

Detection: UV 254 nm

Retention time: 47 min

Rf=0.36 (hexane/ethyl acetate=2/1)

NMR (CHCl$_3$) δ: 7.29–7.24 (m, 2H), 7.15–7.09 (m, 2H), 6.70 (t, J=7.6 Hz, 1H), 6.95–6.91 (m, 2H), 6.79–6.73 (m, 2H), 6.53 (dd, J=2.0, 8.2 Hz, 1H), 4.77 (dd, J=5.3, 5.9 Hz, 1H), 4.75–4.61 (m, 1H), 3.93 (dd, J=5.9, 15.9 Hz, 1H), 3.85 (dd, J=5.3, 15.9 Hz, 1H), 3.73–3.54 (m, 4H), 3.70 (s, 3H), 1.91 (br, 1H), 1.87 (br, 1H), 1.67 (m, 4H), 1.36–0.71 (m, 3H), 1.19 (t, J=6.9 Hz, 3H), 1.11 (t, J=6.9 Hz, 3H), 0.88 (d, J=6.9 Hz, 3H), 0.83 (d, J=7.3 Hz, 1H), 0.66 (d, J=7.0 Hz, 3H).

Example 187

Single Diastereomer of 1-(2,2-Diethoxyethyl)-3-(D-
menthoxy)carbonylmethyl-3-(N'-(3-methoxyphenyl)
ureido)indolin-2-one (HPLC first fraction)

The same procedure as in Example 172 was repeated, except for using (RS)-1-(2,2-diethoxyethyl)-3-(N'-(3-methoxyphenyl)ureido)indolin-2-one as a starting material and replacing L-menthyl bromoacetate as a reactant with D-menthyl bromoacetate. Recrystallization of the crude product from isopropyl ether gave the title compound as needles in a 32% yield. As a result of high performance liquid chromatography analysis, the compound was confirmed to consist of a single diastereomer. Because the compound is an enantiomer of the compound of Example 186, the HPLC and NMR data are the same as those of the latter compound.

Example 188

(+)-1-(2,2-Diethoxyethyl)-3-(4-methylphenyl)
aminocarbonylmethyl-3-(N'-(3-methoxyphenyl)
ureido)indolin-2-one To a solution of 2.57 g of a single diastereomer of 1-(2,2-diethoxyethyl)-3-(L-menthoxy)carbonylmethyl-3-(N'-(3-methoxyphenyl)ureido)indolin-2-one (HPLC first fraction) in 150 ml of ethanol was added 50 ml of an aqueous solution of 0.60 g of potassium hydroxide (85%) at room temperature. The mixture was heated under reflux for 1 hour, followed by concentration. Water was added to the residue, and the mixture was washed with chloroform. The aqueous layer was adjusted to pH 2 with 2N hydrochloric acid, and extracted with ethyl acetate. The organic layer was dried over anhydrous sodium sulfate and concentrated to yield 1.90 g of (+)-1-(2,2-diethoxyethyl)-3-hydroxycarbonylmethyl-3-(N'-(3-methoxyphenyl)ureido)indolin-2-one.

In 30 ml of dichloromethane was dissolved 0.5 g of (+)-1-(2,2-diethoxyethyl)-3-hydroxycarbonylmethyl-3-(N'-(3-methoxyphenyl)ureido)indolin-2-one, and 0.22 g of 1-ethyl-3-(3-dimethylaminopropyl)carbodiimide hydrochloride and 0.20 g of p-toluidine were successively added thereto. After stirring the mixture for 9 hours, the reaction mixture was diluted with ethyl acetate and washed successively with dilute hydrochloric acid and saturated aqueous sodium hydrogencarbonate. The organic layer was dried over anhydrous sodium sulfate and concentrated. The crude product was purified by silica gel column chromatography (hexane/ethyl acetate=2/1) to yield 0.49 g of the title compound as a white powder.

Rf=0.21 (hexane/ethyl acetate=2/1)

NMR (CDCl$_3$) δ: 8.15 (s, 1H), 7.35–7.23 (m, 6H), 7.13–6.91 (m, 6H), 6.73 (d, J=7.3 Hz, 1H), 6.50 (dd, J=2.4, 7.8 Hz, 1H), 4.79 (dd, J=4.4, 5.9 Hz, 1H), 3.98 (dd, J=5.9, 14.1 Hz, 1H), 3.86–3.52 (m, 5H), 3.67 (s, 3H), 2.98 (d, J=14.6 Hz, 1H), 2.54 (d, J=14.6 Hz, 1H), 2.30 (s, 3H), 1.18 (t, J=6.8 Hz, 3H), 1.10 (t, J=6.8 Hz, 3H).

$[α]_D^{25}$=+33.8° (c=1.07, CHCl$_3$)

Example 189

(−)-1-(2,2-Diethoxyethyl)-3-(4-methylphenyl)aminocarbonylmethyl-3-(N'-(3-methoxyphenyl)ureido)indolin-2-one To a solution of 1.89 g of a single diastereomer of 1-(2,2-diethoxyethyl)-3-(D-menthoxy)carbonylmethyl-3-(N'-(3-methoxyphenyl)ureido)indolin-2-one (HPLC first fraction) in 100 ml of ethanol was added 30 ml of an aqueous solution of 0.46 g of potassium hydroxide (85%) at room temperature, and the mixture was stirred at 80° C. for 2 hours followed by concentration. Water was added to the concentrate, and the mixture was washed with chloroform. The aqueous layer was adjusted to pH 2 by addition of 2N hydrochloric acid and extracted with ethyl acetate. The organic layer was dried over anhydrous sodium sulfate and concentrated to afford 1.76 g of (−)-1-(2,2-diethoxyethyl)-3-hydroxycarbonylmethyl-3-(N'-(3-methoxyphenyl)ureido)indolin-2-one.

In 30 ml of dichloromethane was dissolved 0.50 g of (−)-1-(2,2-diethoxyethyl)-3-hydroxycarbonylmethyl-3-(N'-(3-methoxyphenyl)ureido)indolin-2-one, and 0.22 g of 1-ethyl-3-(3-dimethylaminopropyl)-carbodiimide hydrochloride and 0.20 g of p-toluidine were successively added thereto. After stirring the mixture for 9 hours, the reaction mixture was diluted with ethyl acetate and washed successively with dilute hydrochloric acid and saturated aqueous sodium hydrogencarbonate. The organic layer was dried over anhydrous sodium sulfate and concentrated. The crude product was purified by silica gel column chromatography (hexane/ethyl acetate=2/1) to give 0.46 g of the title compound as a white powder. Because the compound is an enantiomer of the compound of Example 188, the NMR data are the same as those of the latter compound.

$[α]_D^{25}$=−36.9° (c=1.02, CHCl$_3$)

EXAMPLES 190 TO 191

The following compounds were prepared in the same manner as in Example 188, except for using various amines as a reactant in place of p-toluidine used in Example 188.

Example 190

(+)-1-(2,2-Diethoxyethyl)-3-(N'-(3-methoxyphenyl)ureido)-3-((5-methylpyrido-2-yl)aminocarbonylmethyl)indolin-2-one The Rf and NMR data were equal to those of the compound of Example 158.

$[α]_D^{25}$=+54.08° (c=1.03, CHCl$_3$)

Example 191

(+)-1-(2,2-Diethoxyethyl)-3-(N'-(3-methoxyphenyl)ureido)-3-((4-(N'N-dimethylaminophenyl)aminocarbonylmethyl)indolin-2-one The Rf and NMR data were equal to those of the compound of Example 156.

$[α]_D^{25}$=+61.79° (c=1.00, CHCl$_3$)

EXAMPLES 192 TO 193

The following compounds were prepared in the same manner as in Example 189, except for using various amines as a reactant in place of p-toluidine used in Example 189.

Example 192

(−)-1-(2,2-Diethoxyethyl)-3-(N'-(3-methoxyphenyl)ureido)-3-((5-methylpyrido-2-yl)aminocarbonylmethyl)indolin-2-one The Rf and NMR data were equal to those of the compound of Example 158.

$[α]_D^{25}$=−54.91° (c=1.01, CHCl$_3$)

Example 193

(−)-1-(2,2-Diethoxyethyl)-3-(N'-(3-methoxyphenyl)ureido)-3-((4-N'N-dimethylamino)phenyl)aminocarbonylmethyl)indolin-2-one The Rf and NMR data were equal to those of the compound of Example 156.

$[α]_D^{25}$=−63.99° (c=1.00, CHCl$_3$)

Example 194

(+)-1-(2,2-Diethoxyethyl)-3-((4-(N,N-dimethylamino)phenyl)aminocarbonylmethyl)-3-(N'-(4-methylphenyl)ureido)indolin-2-one Potassium Hydrogensulfate The compound obtained in Example 180 was mixed with 1 equivalent of potassium hydrogensulfate, and the mixture was recrystallized from methanol to obtain the title compound as needles.

Melting point: 180° C. (decomposition)

NMR (DMSO-d$_6$) δ: 9.98 (br, 1H), 9.13 (s, 1H), 7.57 (s, 1H), 7.46 (d, J=8.2 Hz, 2H), 7.25–6.80 (m, 11H), 4.75–4.69 (m, 1H), 3.85 (dd, J=5.8, 14.6 Hz, 1H), 3.77–3.44 (m, 5H), 2.83 (d, J=14.1 Hz, 1H), 2.51 (s, 6H), 2.47 (d, J=14.1 Hz, 1H), 2.18 (s, 3H), 1.11 (t, J=7.3 Hz, 3H), 1.07 (t, J=6.8 Hz, 3H).

$[α]_D^{24}$+98.88° (c=0.72, MeOH).

REFERENCE EXAMPLE 27

1-(2,2-Diethoxyethyl)indole

To a solution of 12 g of indole in 100 ml of dimethyl sulfoxide was added 6.5 g of sodium hydride at room temperature. The mixture was stirred at the same temperature for 1 hour, and 20 ml of bromoacetaldehyde diethyl acetal was added thereto, followed by further stirring at 50° C. for 1 hour. After cooling, the reaction mixture was poured into water, and the product was extracted with ethyl ether. The organic layer was dried over anhydrous magnesium sulfate and concentrated to give 23 g of the title compound.

NMR (CDCl$_3$) δ: 7.60 (d, J=6.9 Hz, 1H), 7.39 (d, J=9.1 Hz, 1H), 7.26–7.03 (m, 3H), 6.48 (d, J=3.4 Hz, 1H), 4.64 (t, J=5.1 Hz, 1H), 4.20 (d, J=5.1 Hz, 2H), 3.79–3.47 (m, 2H), 3.42–3.24 (m, 2H), 1.12 (t, J=7.3 Hz, 6H).

REFERENCE EXAMPLE 28

1-(2,2-Diethoxyethyl)-3,3-dichloroindolin-2-one

To a suspension of 23 g of 1-(2,2-diethoxyethyl)indole and 31 g of potassium dihydrogenphosphate in 1 l of ethyl acetate was added 700 ml of a 5% aqueous solution of sodium hypochlorite under ice-cooling, followed by stirring at that temperature for 10 minutes. The mixture was washed successively with water and an aqueous solution of potassium carbonate. The organic layer was dried over anhydrous sodium sulfate and concentrated under reduced pressure to give 31 g of the title compound.

Rf=0.50 (hexane/ethyl acetate=3/1)

NMR (CDCl$_3$) δ: 7.61 (d, J=8.2 Hz, 1H), 7.40–7.30 (m, 1H), 7.22–6.98 (m, 2H), 4.74 (t, J=5.4 Hz, 1H), 3.84 (d, J=5.4 Hz, 2H), 3.86–3.67 (m, 2H), 3.60–3.40 (m, 2H), 1.14 (t, J=7.3 Hz, 6H).

REFERENCE EXAMPLE 29

1-(2,2-Diethoxyethyl)isatin

To a solution of 31 g of 1-(2,2-diethoxyethyl)-3,3-dichloroindolin-2-one in 200 ml of dimethyl sulfoxide was added dropwise 50 ml of an aqueous solution of 14.5 g of sodium hydroxide in such a manner that the reaction temperature might not exceed 20° C., followed by stirring at the same temperature for 45 minutes. To the mixture was slowly added 15.5 ml of concentrated hydrochloric acid, followed by stirring at room temperature for 1.5 hours. Ethyl acetate was added to the reaction mixture, and the mixture was washed successively with water and an aqueous solution of sodium hydrogencarbonate. The organic layer was dried over anhydrous sodium sulfate and concentrated to give 25 g of the title compound.

Rf=0.83 (chloroform/methanol=20/1)

NMR (CDCl$_3$) δ: 7.75–6.95 (m, 4H), 4.71 (t, J=5 Hz, 1H), 3.89–3.40 (m, 6H), 1.16 (t, J=7 Hz, 6H).

Example 195

(RS)-1-(2,2-Ethoxyethyl)-3-(N'-(4-methylphenyl)ureido)indolin-2-one

In 3.8 l of methanol was dissolved 176 g of isatin while heating, and a solution of 100 g of O-methylhydroxylamine hydrochloride and 136 g of sodium acetate trihydrate in 400 ml of water was added thereto. The resulting mixture was stirred at room temperature for 10 minutes, followed by concentration. Water was added to the residue, and the mixture was extracted with ethyl acetate. The organic layer was washed with saturated aqueous sodium hydrogencarbonate, dried over anhydrous sodium sulfate, and concentrated to give 192 g (91%) of 3-methoxyiminoindolin-2-one. The resulting crude product was used in the subsequent reaction without being purified.

NMR (CDCl$_3$) δ: 9.36 (br, 1H), 7.94 (d, J=7.6 Hz, 1H), 7.34 (dt, J=1.3, 7.6 Hz, 1H), 7.05 (dt, J=1.0, 7.6 Hz, 1H), 6.92 (d, J=7.6 Hz, 1H), 4.31 (s, 3H).

To a suspension of sodium hydride (prepared by washing 50 g of 60% oily sodium hydride with hexane) in 1 l of N,N-dimethylformamide was added dropwise a solution of 176 g of 3-methoxyiminoindolin-2-one in 3 l of N,N-dimethylformamide at 0° C. in a nitrogen stream. To the mixture were added 1 l of N,N-dimethylformamide and 330 ml of bromoacetaldehyde diethyl acetal, and the mixture was heated to 70° C., at which it was stirred for 45 hours. The reaction mixture was concentrated, and the concentrate was diluted with ethyl acetate and washed with an aqueous solution of sodium chloride. The organic layer was dried over anhydrous sodium sulfate and concentrated to give 284 g (97%) of 1-(2,2-diethoxyethyl)-3-methoxyiminoindolin-2-one.

NMR (CDCl$_3$) δ: 7.93 (d, J=7.8 Hz, 1H), 7.36 (dt, J=1.5, 7.8 Hz, 1H), 7.08–7.00 (m, 2H), 4.70 (t, J=5.4 Hz, 1H), 4.29 (s, 3H), 3.85 (d, J=5.4 Hz, 2H), 3.79–3.43 (m, 4H), 1.14 (t, J=7.3 Hz, 6H).

To a solution of 0.51 g of 1-(2,2-diethoxyethyl)-3-methoxyiminoindolin-2-one in 30 ml of ethanol were added 50 mg of 5% Pd/C and 1 ml of 2N hydrochloric acid, and the resulting suspension was stirred at room temperature for 18 hours under a hydrogen atmosphere. The reaction mixture was filtered through Cerite, and the filtrate was concentrated. The residue was suspended in 30 ml of toluene, and 0.25 ml of triethylamine and 0.27 ml of p-tolyl isocyanate were added thereto, followed by stirring at room temperature for 1 hour. The reaction mixture was concentrated and washed with water to give 0.55 g of the title compound.

NMR (DMSO-d$_6$) δ: 8.63 (s, 1H), 7.33–7.16 (m, 4H), 7.12–7.16 (m, 4H), 5.05 (d, J=7.4 Hz, 1H), 4.77–4.63 (m, 1H), 3.84 (dd, J=5.7, 14.6 Hz, 1H), 3.77–3.40 (m, 5H), 2.22 (s, 3H), 1.08 (t, J=7.4 Hz, 3H), 1.06 (t, J=7.4 Hz, 3H).

Example 196

(+)-3-(p-Bromobenzyloxy)carbonylmethyl-1-(2,2-diethoxyethyl)-3-(N'-(4-methylphenyl)ureido)indolin-2-one In 10 ml of dimethyl sulfoxide was dissolved 0.336 g of (+)-1-(2,2-diethoxyethyl)-3-hydroxycarbonylmethyl-3-(N'-(4-methylphenyl)ureido)indolin-2-one. To the solution were added successively 0.108 g of 4-dimethylaminopyridine, 0.170 g of 1-ethyl-3-(3-dimethylaminopropyl)carbodiimide hydrochloride and 0.166 g of 4-bromobenzyl alcohol. The resulting mixture was stirred for 18 hours, followed by concentration. The concentrate was diluted with ethyl ether, washed successively with dilute hydrochloric acid and a saturated aqueous solution of sodium hydrogencarbonate. The organic layer was dried over anhydrous sodium sulfate, and concentrated. The crude product was purified by silica gel column chromatography (hexane/ethyl acetate=2/1) to give 0.219 g (48%) of the title compound as a white powder.

NMR (CDCl$_3$) δ: 7.45 (d, J=8.8 Hz, 2H), 7.30–6.80 (m, 10H), 6.71 (s, 1H), 6.60 (s, 1H), 5.05 (d, J=12.7 Hz, 1H), 5.00 (d, J=12.7 Hz, 1H), 4.73 (dd, J=4.9, 5.9 Hz, 1H), 3.93 (dd, J=5.9, 14.6 Hz, 1H), 3.83–3.30 (m, 5H), 2.97 (d, J=15.1 Hz, 1H), 2.65 (d, J=15.1 Hz, 1H), 2.28 (s, 3H), 1.15 (t, J=7.3 Hz, 3H), 1.10 (t, J=7.3 Hz, 3H).

Example 197

3-(+)-1-(2,2-Diethoxyethyl)-3-(N'-(4-methylphenyl)ureido)-3-((1R-1-methylpropoxy)carbonylmethyl)indolin-2-one The title compound was prepared in the same manner as in Example 196, except for using R-2-butanol as a reactant in place of 4-bromobenzyl alcohol used in Example 196.

NMR (CDCl$_3$) δ: 7.30–7.20 (m, 2H), 7.13–6.92 (m, 6H), 6.89 (s, 1H), 6.79 (s, 1H), 4.87–4.70 (m, 2H), 3.95 (dd, J=5.9, 14.1 Hz, 1H), 3.86–3.46 (m, 5H), 2.95 (d, J=15.1 Hz, 1H), 2.56 (d, J=15.1 z, 1H), 2.26 (s, 3H), 1.55–1.37 (m, 2H), 1.21–1.00 (m, 9H), 0.81 (t, J=8.1 Hz, 3H).

Example 198

(+)-1-Formylmethyl-3-(4-methylphenyl) aminocarbonylmethyl-3-(N'-(4-methylphenyl) ureido)indolin-2-one To a solution of 0.227 g of (+)-1-(2,2-diethoxyethyl)-3-(4-methylphenyl)aminocarbonylmethyl-3-(N'-(4-methylphenyl)ureido)indolin-2-one in 5 ml of acetone was added 5 ml of 6N hydrochloric acid, followed by heating under reflux for 10 minutes. The reaction mixture was concentrated, and the residue was diluted with ethyl acetate and washed twice with an aqueous solution of sodium chloride. The organic layer was dried over anhydrous magnesium sulfate and concentrated to give 0.189 g of the title compound as a crude product.

NMR (CDCl$_3$) δ: 9.59 (s, 1H), 8.12 (s, 1H), 7.42 (s, 1H), 7.31–6.84 (m, 12H), 6.57 (d, J=7.6 Hz, 1H), 4.62 (d, J=18.8 Hz, 1H), 4.29 (d, J=18.8 Hz, 1H), 2.90 (d, J=15.9 Hz, 1H), 2.58 (d, J=15.9 Hz, 1H), 2.25 (s, 3H), 2.18 (s, 3H).

Example 199

(+)-1-Formylmethyl-3-hydroxycarbonylmethyl-3-(N'-(4-methylphenyl)ureido)indolin-2-one The title compound was prepared in the same manner as in Example 198, except for starting with (+)-1-(2,2-diethoxyethyl)-3-hydroxycarbonylmethyl-3-(N'-(4-methylphenyl)ureido)indolin-2-one in place of (+)-1-(2,2-diethoxyethyl)-3-(4-methylphenyl)aminocarbonylmethyl-3-(N'-(4-methylphenyl)ureido)indolin-2-one used in Example 198.

NMR (DMSO-d$_6$) δ: 9.61 (s, 1H), 8.95 (s, 1H), 7.33–6.94 (m, 10H), 4.68 (d, J=18.5 Hz, 1H), 4.54 (d, J=18.5 Hz, 1H), 2.87 (d, J=15.8 Hz, 1H), 2.56 (d, J=15.8 Hz, 1H), 2.17 (s, 3H).

Example 200

3-(+)-1-Formylmethyl-3-(L-menthoxy) carbonylmethyl-3-(N'-(4-methylphenyl)ureido) indolin-2-one The title compound was prepared in the same manner as in Example 198, except for starting with (+)-1-(2,2-diethoxyethyl)-3-(L-menthoxy)carbonylmethyl-3-(N'-(4-methylphenyl)ureido)indolin-2-one in place of (+)-1-(2,2-diethoxyethyl)-3-(4-methylphenyl)aminocarbonylmethyl-3-(N'-(4-methylphenyl)ureido)indolin-2-one used in Example 198.

NMR (CDCl$_3$) δ: 9.72 (s, 1H), 7.33–6.68 (m, 10H), 4.75–4.61 (m, 2H), 4.47 (d, J=17.8 Hz, 1H), 2.99 (d, J=15.4 Hz, 1H), 2.63 (d, J=15.4 Hz, 1H), 2.26 (s, 3H), 1.92–1.84 (br, 1H), 1.71–1.59 (br, 3H), 1.43–1.38 (br, 1H), 1.30–1.14 (br, 4H), 0.89 (d, J=6.6 Hz, 3H), 0.82 (d, J=6.9 Hz, 3H), 0.64 (d, J=6.9 Hz, 3H).

Example 201

(+)-1-(2-Hydroxyiminoethyl)-3-(4-methylphenyl) aminocarbonylmethyl-3-(N'-(4-methylphenyl) ureido)indolin-2-one In 1 ml of methanol was dissolved 0.050 g of (+)-1-formylmethyl-3-(4-methylphenyl)aminocarbonylmethyl-3-(N'-(4-methylphenyl)ureido)indolin-2-one, and a solution of 0.021 g of hydroxylamine hydrochloride and 0.021 g of sodium acetate in 1 ml of water was added thereto. The resulting mixture was stirred at room temperature for 1 hour and concentrated. Water was added to the residue, and the mixture was extracted with ethyl acetate. The organic layer was washed with saturated aqueous sodium hydrogencarbonate, dried over anhydrous sodium sulfate, and concentrated. The residue was purified by silica gel column chromatography (dichloromethane/ethyl acetate=1/1) to give 0.045 g of the title compound.

Rf=0.18 (dichloromethane/ethyl acetate=2/1)

NMR (CDCl$_3$-DMSO-d$_6$) δ: 10.09 (br, 0.5H), 9.62 (br, 0.5H), 8.69 (br, 0.5H), 7.57 (br, 0.5H), 7.43–7.38 (m, 1H), 7.30–7.14 (m, 5H), 7.06–6.77 (m, 9H), 4.71–4.52 (m, 1.5H), 4.30–4.18 (m, 0.5H), 2.89 (d, J=14.5 Hz, 0.5H), 2.85 (d, J=14.5 Hz, 0.5H), 2.51–2.40 (m, 1H), 2.26 (s, 3H), 2.19 (s, 3H).

Structural formulae of the compounds prepared in the foregoing Examples are shown in Tables A and B below.

TEST EXAMPLE 1

Gastrin Receptor Binding Test in Guinea Pig Gastric Glands Preparation of Gastric Glands Guinea pig gastric glands were prepared according to the method of Chang, et al., *Biochem. Biophys. Res. Commun.*, 134, 895 (1986). The gastric mucosa of a Hartley male guinea pig was peeled off. After washing, the mucosa was minced with scissors in buffer A (Eagle's MEM containing 2 mM L-glutamine and 25 mM HEPES; pH 7.4). After washing, the minced tissue was incubated in buffer A containing 0.025% collagenase, 0.01% soy bean trypsin inhibitor, and 0.1% BSA at 37° C. for 60 minutes under 95% 0$_2$ and 5% CO$_2$. The gastric glands were isolated from the tissue with a pipette, washed twice with buffer A, and filtered through a mesh. Then, the gastric glands were obtained by centrifugation.

Binding Test

Guinea pig gastric glands were resuspended in buffer B (Hank's solution containing 10 mM HEPES and 0.2% BSA; pH 7.4) (10 ml of buffer B per guinea pig).

To 200 μl of the suspension containing the resuspended isolated gastric glands were added 20 pl of $^{125}$I-gastrin I human (final concentration: 22.5 pM). Then, 10 μl of a test compound or a solvent (for total binding) or 10 μM Pentagastrin (for nonspecific binding), and buffer B was added there to make a total volume of 1 ml. The reaction mixture was incubated at 25° C. for 45 minutes and then centrifuged at 12000 g. The supernatant was removed by suction, and the radioactivity of the isolated gastric glands was measured with a gamma-counter.

The specific binding of gastrin to gastrin receptors was obtained from a difference between the total binding and the nonspecific binding. The IC$_{50}$ of the test compound in inhibition of specific binding was calculated.

The results obtained are shown in Table C.

TEST EXAMPLE 2

Inhibitory Activity on Gastric Acid Secretion in Pyrolus Ligated Rats

Sprague-Dawley male rats weighing about 200 g were deprived of food for 24 hours while allowed water ad libitum. The abdomen was opened under anesthesia with ethyl ether, the pyrolus ligated, and the abdomen closed. The rats were deprived of food and water for 4 hours until they were surcrified with ethyl ether. The stomach was removed, and gastric juice was collected and measured. The gastric juice was centrifuged at 3000 rpm, and the supernatant was titrated up to pH 7.0 with 0.1N NaOH solution to obtain the acidity of the gastric juice. The amount of the gastric acid output was calculated by multiplying the gastric juice volume by the acidity, and the percent inhibition of acid secretion was obtained according to the following equation. A test compound, suspended in a 3% gum arabic solution, was administered intraduodenally at a dose of 2 ml/kg immediately after the pyrolus ligation.

Inhibition (%)=[(Average amount of gastric acid output in control group–Average amount of gastric acid output in test group)/ Average amount of gastric acid secreted in test group]×100

The results obtained are shown in Table C.

TEST EXAMPLE 3

CCK-B Receptor Binding Test in Rat Cerebral Cortex

A rat cortical membrane fraction was prepared in accordance with the method of Chang, et al., *Proc. Natl. Acad. Sci., U.S.A.*, 83, 4923 (1986). Sprague-Dawley male rats were sucrified and the brains were removed and immersed in a 50 mM Tris-HCl buffer (pH 7.4) under ice-cooling, and the cortex was dissected. Cerebral cortex was minced in the same buffer, and homogenized with Polytron. The homogenate was centrifuged at 2,500 g, and the supernatant was further centrifuged at 50,000 g. The pellet was resuspended in a reaction buffer solution (10 mM HEPES, 5 mM $MgCl_2$, 1 mM EGTA, 130 mM NaCl; pH 6.5).

Binding Test

To 150 μl of the resulting rat cerebral cortex suspension were added 20 μl of $^{125}$1-CCK-8 sulfated (final concentration: 15 pM) and 10 μl of a test compound or a solvent (for total binding) or 1 pM CCK-8 sulfated (for nonspecific binding), and the reaction buffer solution was added there to make 1 ml. The reaction mixture was incubated at 25° C. for 120 minutes, followed by filtration through a GF/B filter (produced by Whatman). The radioactivity of the membrane fraction adsorbed onto the filter was measured with a gamma-counter.

The specific binding to CCK-B receptors was obtained from a difference between the total binding and the nonspecific binding. The $IC_{50}$ of the test compound in inhibition of specific binding was calculated.

The results obtained are shown in Table D.

As is apparent from Table C, it was confirmed that the compound of the present invention exhibits excellent gastrin receptor antagonism as well as inhibitory effect on gastric acid secretion.

As is apparent from Table D, it was confirmed that the compound of the present invention exhibits excellent antagonism against CCK-B receptors.

TABLE A-1

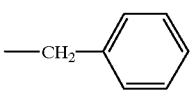

| Ex. No. | $(R_1)n$ | $R_2$ | X | $R_3$ | Y | $R_4$ |
|---|---|---|---|---|---|---|
| 1 | — | —CH$_2$—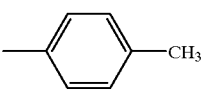 | NH | 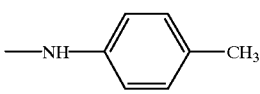—CH$_3$ | NH | —NH—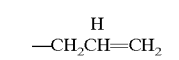—CH$_3$ |
| 2 | 5-NO$_2$ | H | " | " | " | " |
| 3 | — | —CH$_2$CH=CH$_2$ | " | " | " | " |
| 4 | — | —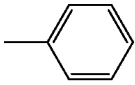 | " | " | " | " |
| 5 | — | —CH$_2$CH(OCH$_3$)$_2$ | " | " | " | " |
| 6 | — | —CH$_2$CH(OC$_3$H$_7$-n)$_2$ | " | " | " | " |
| 7 | — | —CH$_2$CH(OCH$_3$)(OC$_2$H$_5$) | " | " | " | " |
| 8 | — | H | " | " | " | " |
| 9 | — | H | " | — | " | —NH— |

TABLE A-1-continued
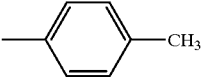
| Ex. No. | $(R_1)n$ | $R_2$ | X | $R_3$ | Y | $R_4$ |
|---|---|---|---|---|---|---|
| 10 | — | —$CH_2CH(OC_2H_5)_2$ | " | 4-CH₃-C₆H₄— | " | —NH—C₆H₄-4-CH₃ |
| 11 | — | " | " | 4-OCH₃-C₆H₄— | " | —NH—C₆H₄-4-OCH₃ |
| 12 | — | " | " | 4-COOCH₃-C₆H₄— | " | —NH—C₆H₄-4-COOCH₃ |
| 13 | — | " | " | 4-CN-C₆H₄— | " | —NH—C₆H₄-4-CN |
| 14 | — | " | " | 4-F-C₆H₄— | " | —NH—C₆H₄-4-F |
| 15 | — | " | " | 3-F-C₆H₄— | " | —NH—C₆H₄-3-F |
| 16 | — | " | " | 4-NO₂-C₆H₄— | " | —NH—C₆H₄-4-NO₂ |
| 17 | — | " | " | 4-CF₃-C₆H₄— | " | —NH—C₆H₄-4-CF₃ |
| 18 | — | " | " | 2-F-C₆H₄— | " | —NH—C₆H₄-2-F |
| 19 | — | " | " | 2-CN-C₆H₄— | " | —NH—C₆H₄-2-CN |

TABLE A-1-continued

[Structure: indolin-2-one core with (R₁)n on benzene ring (positions 4,5,6,7), N1-R₂, C3 substituted with X-C(=O)-NHR₃ and Y-C(=O)-R₄]

| Ex. No. | (R₁)n | R₂ | X | R₃ | Y | R₄ |
|---|---|---|---|---|---|---|
| 20 | — | " | " | 4-Br-phenyl | " | —NH—(4-Br-phenyl) |

TABLE A-2

[Structure: indolin-2-one core with (R₁)n on benzene ring (positions 4,5,6,7), N1-R₂, C3 substituted with X-C(=O)-NHR₃ and Y-C(=O)-R₄]

| Ex. No. | (R₁)n | R₂ | X | R₃ | Y | R₄ |
|---|---|---|---|---|---|---|
| 21 | — | —CH₂CH(OC₂H₅)₂ | NH | 3-Br-phenyl | NH | —NH—(3-Br-phenyl) |
| 22 | — | H | CH₂ | 4-CH₃-phenyl | CH₂ | —NH—(4-CH₃-phenyl) |
| 23 | — | —CH₂—phenyl | " | " | " | " |
| 24 | — | CH₃ | " | " | " | " |
| 25 | — | —CH₂CO—phenyl | " | " | " | " |
| 26 | — | —CH₂-(2-pyridyl) | " | " | " | " |
| 27 | — | —CH₂—phenyl | O | " | " | " |
| 53a | — | —CH₂COOC₂H₅ | NH | " | " | OC₂H₅ |
| 53b | — | H | " | " | " | " |

TABLE A-2-continued

| Ex. No. | (R₁)n | R₂ | X | R₃ | Y | R₄ |
|---|---|---|---|---|---|---|
| 54a | — | —CH₂CO-phenyl | " | " | " | phenyl |
| 54b | — | H | " | " | " | " |
| 55 | — | " | " | " | " | OH |
| 56 | — | —CH₂COOH | " | " | " | " |
| 57 | — | H | " | " | " | —NH-C₆H₄-CH₃ (p) |
| 58 | — | " | " | " | " | N-methylpiperazinyl |
| 59 | — | " | " | " | " | piperidinyl |
| 60 | — | " | CH₂ | " | NH | —CH₂-C₆H₄-CH₃ (p) |
| 61 | — | —CH₂-phenyl | " | " | " | CH₃ |
| 62 | — | " | " | " | " | —NH-C₆H₄-CH₃ (p) |
| 63 | — | —CH₂CO-phenyl | NH | " | CH₂ | " |

TABLE A-3
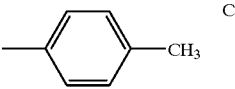
| Ex. No. | (R₁)n | R₂ | X | R₃ | Y | R₄ |
|---|---|---|---|---|---|---|
| 64 | — | —CH₂COOC₂H₅ | NH | 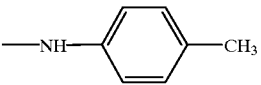 -CH₃ | CH₂ | —NH- 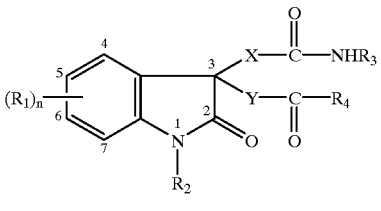 -CH₃ |
| 65 | — | —CH₂- 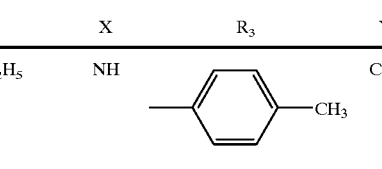 (2-pyridyl) | " | " | " | " |
| 66 | — | —CH₂CH₂- 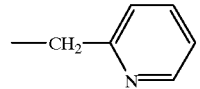 | " | " | " | " |
| 67 | — | CH₃ | " | " | " | " |
| 68 | — | —CH₂-  (4-pyridyl) | " | " | " | " |
| 69 | — | —CH₂OCH₃ | " | " | " | " |
| 70 | — | —CH₂CH(C₃H₇-n)₂ | " | " | " | " |
| 71 | — | —CH₂CH(OC₂H₅)₂ | " | " | " | " |
| 72 | 7-CH₃ | H | " | " | " | " |
| 73 | — | 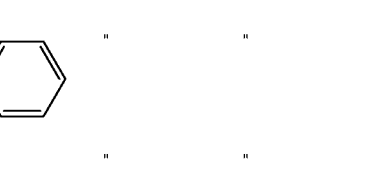 (phenyl) | " | " | " | " |
| 74 | 5-CH₃ | —CH₂CH(OC₂H₅)₂ | " | " | " | " |
| 75 | 5-F | " | " | " | " | " |
| 76 | 5-OCH₃ | " | " | " | " | " |
| 77 | 5-Br | " | " | " | " | " |
| 78 | — | " | " | 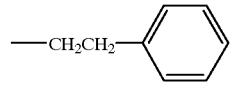 -Cl | " | " |
| 79 | — | " | " |  -OCH₃ | " | " |
| 80 | — | " | " | 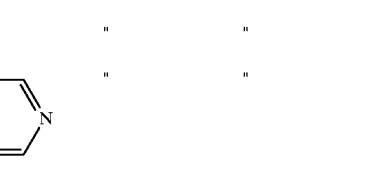 (cyclohexyl) | " | " |
| 81 | — | " | " | 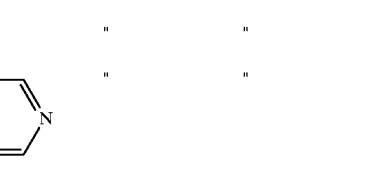 -CH₃ (3-methylphenyl) | " | " |

TABLE A-3-continued

Structure: Indolin-2-one with (R₁)ₙ on benzene ring (positions 4,5,6,7), N1-R₂, C3 substituted with X-C(=O)-NHR₃ and Y-C(=O)-R₄.

| Ex. No. | (R₁)n | R₂ | X | R₃ | Y | R₄ |
|---|---|---|---|---|---|---|
| 82 | — | " | " | 4-F-C₆H₄- | " | " |
| 83 | — | " | " | 2-Cl-C₆H₄- | " | " |

TABLE A-4

Structure: Indolin-2-one with (R₁)ₙ on benzene ring (positions 4,5,6,7), N1-R₂, C3 substituted with X-C(=O)-NHR₃ and Y-C(=O)-R₄.

| Ex. No. | (R₁)n | R₂ | X | R₃ | Y | R₄ |
|---|---|---|---|---|---|---|
| 84 | — | —CH₂CH(OC₂H₅)₂ | NH | C₆H₅- | CH₂ | —NH-C₆H₄-CH₃ (4-) |
| 85 | — | " | " | 3-OCH₃-C₆H₄- | " | " |
| 86 | — | " | " | C₂H₅ | " | " |
| 87 | — | " | " | 4-COOC₂H₅-C₆H₄- | " | " |
| 88 | — | " | " | 2-CH₃-C₆H₄- | " | " |
| 89 | — | " | " | 3-Cl-C₆H₄- | " | " |

TABLE A-4-continued

| Ex. No. | (R₁)n | R₂ | X | R₃ | Y | R₄ |
|---|---|---|---|---|---|---|
| 90 | — | " | " | 2-CH₃O-C₆H₄- | " | " |
| 91 | — | " | " | 4-NO₂-C₆H₄- | " | " |
| 92 | — | " | " | 4-CN-C₆H₄- | " | " |
| 93 | — | " | " | 3-CF₃-C₆H₄- | " | " |
| 94 | — | " | " | 3-F-C₆H₄- | " | " |
| 95 | — | " | " | 4-CF₃-C₆H₄- | " | " |
| 96 | — | —CH₂CH(OC₃H₇-n)₂ | " | 4-CH₃-C₆H₄- | " | " |
| 97 | — | —CH₂CHO | " | " | " | " |
| 98 | — | —CH₂-(1,3-dioxolan-2-yl) | " | " | " | " |
| 99 | — | —CH₂CH(OCH₂C₆H₅)₂ | " | " | " | " |
| 100 | — | —CH₂CH(OCH₃)₂ | " | " | " | " |

TABLE A-4-continued
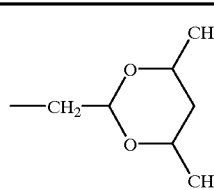
| Ex. No. | (R₁)n | R₂ | X | R₃ | Y | R₄ |
|---|---|---|---|---|---|---|
| 101 | — | 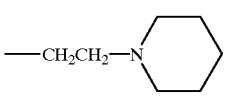 | " | " | " | " |
| 102 | — | —CH₂CH₂NHCH₃·NCl | " | " | " | " |
| 103 | — | 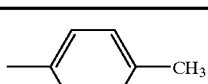 | " | " | " | " |
TABLE A-5
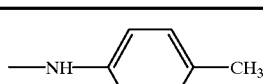
| Ex. No. | (R₁)n | R₂ | X | R₃ | Y | R₄ |
|---|---|---|---|---|---|---|
| 104 | — | —CH₂CH₂N(CH₃)₂ | NH | 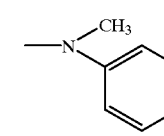 | CH₂ | 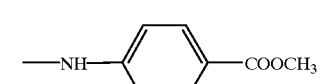 |
| 105 | — | —CH₂CH(SCH₃)₂ | " | " | " | " |
| 106 | — | —CH₂CH(SC₂H₅)₂ | " | " | " | " |
| 107 | — | —CH₂CH(OC₂H₅)₂ | " | " | " | OC₂H₅ |
| 108 | — | " | " | " | " | OH |
| 109 | — | " | " | " | " | 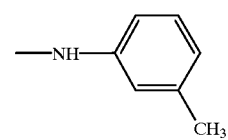 |
| 110 | — | " | " | " | " | —NH—C₆H₄—COOCH₃ |
| 111 | — | " | " | " | " | —NH—C₆H₄—CH₃ (meta) |

TABLE A-5-continued
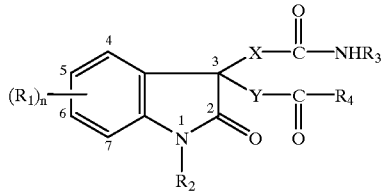
| Ex. No. | (R₁)n | R₂ | X | R₃ | Y | R₄ |
|---|---|---|---|---|---|---|
| 112 | — | " | " | " | " | 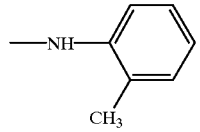 —NH—C₆H₄—CH₃ (o) |
| 113 | — | " | " | " | " | —NHC₃H₇-n |
| 114 | — | " | " | " | " |  —NH—C₆H₄—Cl (p) |
| 115 | — | " | " | " | " | 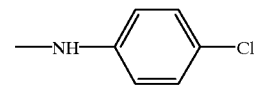 —NH—C₆H₄—OCH₃ (p) |
| 116 | — | " | " | " | " | —NH(CH₂)₃COOC₂H₅ |
| 117 | — | " | " | " | " | —NHOCH₃ |
| 118 | — | " | " | " | " | 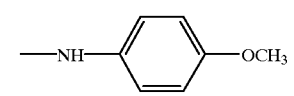 —NH—C₆H₄—CH₂COOCH₃ |
| 119 | — | " | " | " | " | —NHCH₂CH(OC₂H₅)₂ |
| 120 | — | " | " | " | " | 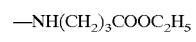 —NH—C₆H₄—C₆H₁₃ |
| 121 | — | " | " | " | " | 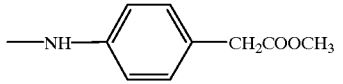 —NH—C₆H₄—NO₂ |
| 122 | — | " | " | " | " | 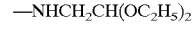 —NH—C₆H₄—C₆H₁₃ |
| 123 | — | " | " | " | " | 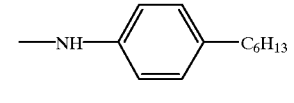 —NH—C₆H₄—Cl (m) |

TABLE A-6

| Ex. No. | (R₁)n | R₂ | X | R₃ | Y | R₄ |
|---|---|---|---|---|---|---|
| 124 | — | —CH₂CH(OC₂H₅)₂ | NH | 4-CH₃-C₆H₄- | CH₂ | —NH—C₆H₄—F (4-F) |
| 125 | — | " | " | " | " | —NH—C₆H₄—NH₂ (4-NH₂) |
| 126 | — | " | " | " | " | —NHCH₂—C₆H₅ |
| 127 | — | " | " | " | " | —NH—C₆H₄—OH (4-OH) |
| 128 | — | " | " | " | " | —NH—C₆H₄—CF₃ (4-CF₃) |
| 129 | — | " | " | " | " | —NH—C₆H₄—OCH₃ (3-OCH₃) |
| 130 | — | " | " | " | " | —NH—C₆H₄—N(CH₃)₂ (4-) |
| 131 | — | " | " | " | " | —NH—C₆H₄—N(CH₃)(COCF₃) (4-) |
| 132 | — | " | " | " | " | —NH-(2-pyrimidinyl) |
| 133 | — | " | " | " | " | —NH—C₆H₅ |
| 134 | — | " | " | " | " | —NH—C₆H₄—N(C₂H₅)₂ (4-) |

TABLE A-6-continued

| Ex. No. | (R₁)n | R₂ | X | R₃ | Y | R₄ |
|---|---|---|---|---|---|---|
| 135 | — | " | " | " | " | —NH—C₆H₄—NHCOCF₃ (para) |
| 136 | — | " | " | " | " | —NH—(5-indolinyl with N-COCF₃) |
| 137 | — | " | " | " | " | —NH—(5-indolyl) |
| 138 | — | " | " | " | " | —NH—(5-methylpyridin-2-yl) |
| 139 | — | " | " | " | " | —NH—(2-chlorophenyl) |
| 140 | — | " | " | " | " | —NH—(pyridin-4-yl) |
| 141 | — | " | " | " | " | —NH—(2-methoxyphenyl) |
| 142 | — | " | " | " | " | —NH—(2-hydroxy-4-methylphenyl) |
| 143 | — | " | " | " | " | —NH—(6-methoxypyridin-3-yl) |

TABLE A-7
| Ex. No. | (R₁)n | R₂ | X | R₃ | Y | R₄ |
|---|---|---|---|---|---|---|
| 144 | — | —CH₂CH(OC₂H₅)₂ | NH | 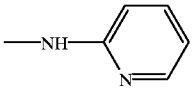 4-CH₃-C₆H₄— | CH₂ |  —NH-(2-pyridyl) |
| 145 | — | " | " | " | " |  —NH-(3-pyridyl) |
| 146 | — | " | " | 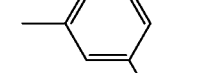 3-OCH₃-C₆H₄— | " | —OC₂H₅ |
| 147 | — | " | " | " | " | —OH |
| 148 | — | " | " | " | " |  —NH-C₆H₄-4-OCH₃ |
| 149 | — | " | " | " | " | 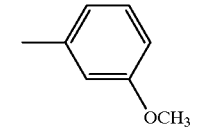 —NH-C₆H₄-4-Cl |
| 150 | — | " | " | " | " | 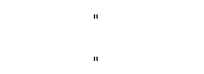 —NH-C₆H₄-2-CH₃ |
| 151 | — | " | " | " | " | 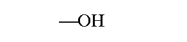 —NH-C₆H₄-3-OCH₃ |
| 152 | — | " | " | " | " |  —NH-C₆H₄-3-CH₃ |
| 153 | — | " | " | " | " |  —NH-C₆H₄-2-OCH₃ |
| 154 | — | " | " | " | " |  —NH-C₆H₄-4-F |

TABLE A-7-continued
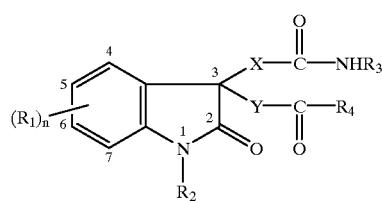
| Ex. No. | (R₁)n | R₂ | X | R₃ | Y | R₄ |
|---|---|---|---|---|---|---|
| 155 | — | " | " | " | " | —NHC₃H₇-n |
| 156 | — | " | " | " | " | —NH—C₆H₄—N(CH₃)₂ |
| 157 | — | " | " | " | " | —NH—C₆H₄—COOCH₃ |
| 158 | — | " | " | " | " | —NH-(5-methylpyridin-2-yl) |
| 159 | — | —CH₂CHO | " | " | " | —NH—C₆H₄—CH₃ |
| 160 | — | —CH₂CH₂N(CH₃)₂ | " | " | " | " |
| 161 | — | —CH₂CH(OC₂H₅)₂ | " | —C₆H₄—CH₃ | " | —NH—C₆H₄—NHCH₃ |
| 162 | — | " | " | " | " | —NH-(indolin-5-yl) |
| 163 | — | " | " | " | " | —NH—C₆H₄—COOH |
TABLE A-8
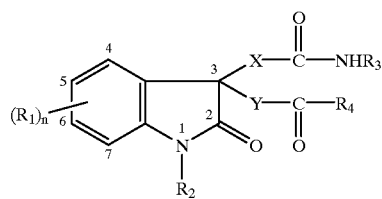
| Ex. No. | (R₁)n | R₂ | X | R₃ | Y | R₄ |
|---|---|---|---|---|---|---|
| 164 | — | —CH₂CH(OC₂H₅)₂ | NH | —C₆H₄—CH₃ | CH₂ | —NH—C₆H₄—CH₂COOH |

TABLE A-8-continued

| Ex. No. | (R₁)n | R₂ | X | R₃ | Y | R₄ |
|---|---|---|---|---|---|---|
| 165 | — | " | CH₂ | " | NH | —NH—C₆H₄—COOH (para) |
| 166 | — | " | " | " | " | —NH—C₆H₄—NH₂ (para) |
| 167 | — | " | " | " | " | —NH—C₆H₄—N(CH₃)₂ (para) |
| 168 | — | " | NH | —C₆H₄—Cl (para) | CH₂ | —NH—C₆H₄—Cl (para) |
| 169 | — | " | " | —C₆H₄—OCH₃ (para) | " | " |
| 170 | — | " | " | —C₆H₄—F (para) | " | —NH—C₆H₄—F (para) |
| 171 | — | " | " | —C₆H₄—CH₃ (para) | " | —O—(L-Menthyl) |
| 172 | — | " | " | " | " | " |
| 173 | — | " | " | —C₆H₃(CH₃)(OCH₃) | " | —O—(D-Menthyl) |
| 174 | — | " | " | —C₆H₄—CH₃ (para) | " | —NH—C₆H₄—CH₃ (para) |
| 175 | — | " | " | " | " | " |
| 176 | — | " | " | " | " | —NH—C₆H₄—I (para) |
| 177 | — | " | " | " | " | —OCH₂CH₂Br |
| 178 | — | " | " | " | " | —OCH₂CH₂I |

TABLE A-8-continued

Structure: indoline-2-one with (R₁)ₙ on positions 4-7 of benzene ring, N1-R₂, C3 substituted with X-C(=O)-NHR₃ and Y-C(=O)-R₄

| Ex. No. | (R₁)n | R₂ | X | R₃ | Y | R₄ |
|---|---|---|---|---|---|---|
| 179 | — | " | " | " | " | —NH—(2-pyridyl-5-CH₃) |
| 180 | — | " | " | " | " | —NH—C₆H₄—N(CH₃)₂ (para) |
| 181 | — | " | " | " | " | —NH—(5-pyridyl-6-OCH₃) |
| 182 | — | " | " | " | " | —NH—(2-pyridyl-5-CH₃) |
| 183 | — | " | " | " | " | —NH—C₆H₄—N(CH₃)₂ (para) |

TABLE A-9

Structure: indoline-2-one with (R₁)ₙ on positions 4-7 of benzene ring, N1-R₂, C3 substituted with X-C(=O)-NHR₃ and Y-C(=O)-R₄

| Ex. No. | (R₁)n | R₂ | X | R₃ | Y | R₄ |
|---|---|---|---|---|---|---|
| 184 | — | —CH₂CH(OC₂H₅)₂ | NH | 4-CH₃-C₆H₄— | CH₂ | —NH—(5-pyridyl-6-OCH₃) |
| 185 | — | " | " | 3-OCH₃-C₆H₄— | " | —O—(L-Menthyl) |
| 186 | — | " | " | " | " | " |
| 187 | — | " | " | " | " | —O—(D-Menthyl) |
| 188 | — | " | " | " | " | —NH—C₆H₄—CH₃ |

TABLE A-9-continued
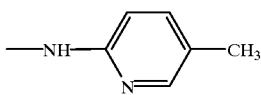
| Ex. No. | (R₁)n | R₂ | X | R₃ | Y | R₄ |
|---------|-------|-----|-----|-----|-----|-----|
| 189 | — | " | " | " | " | " |
| 190 | — | " | " | " | " | —NH—<pyridine-CH₃> |
| 191 | — | " | " | " | " | —NH—<phenyl>—N(CH₃)₂ |
| 192 | — | " | " | " | " | —NH—<pyridine-CH₃> |
| 193 | — | " | " | " | " | —NH—<phenyl>—N(CH₃)₂ |
| 194 | — | " | " | " | " | " |
| 196 | — | " | " | —<phenyl>—CH₃ | " | —OCH₂—<phenyl>—Br |
| 197 | — | " | " | " | " | —O—CH(C₂H₅)CH₃ |
| 198 | — | —CH₂CHO | " | " | " | —NH—<phenyl>—CH₃ |
| 199 | — | " | " | " | " | —OH |
| 200 | — | " | " | " | " | —O—(L-Menthyl) |
| 201 | — | —CH₂CH=NOH | " | " | " | —NH—<phenyl>—CH₃ |

TABLE B-1
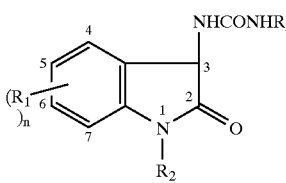
| Ex. No. | (R₂)n | R₂ | R₃ |
|---|---|---|---|
| 28 | — | —CH₂CH(OC₂H₅)₂ | 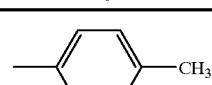 -CH₃ (para) |
| 29 | — | —CH₂-phenyl | " |
| 30 | — | phenyl | " |
| 31 | 5-CH₃ | —CH₂CH(OC₂H₅)₂ | " |
| 32 | 5-Br | " | " |
| 33 | — | " |  -Cl (para) |
| 34 | — | " | 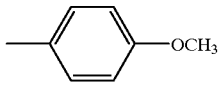 -OCH₃ (para) |
| 35 | — | " | 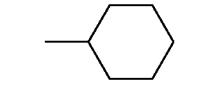 cyclohexyl |
| 36 | — | " | 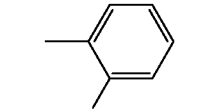 -Cl (ortho) |
| 37 | — | " | 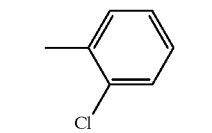 -Cl (ortho) |
| 38 | — | " | 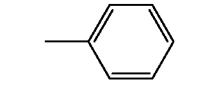 phenyl |
| 39 | — | " | 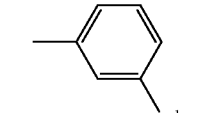 -OCH₃ (meta) |
| 40 | — | " | —C₂H₅ |

TABLE B-2
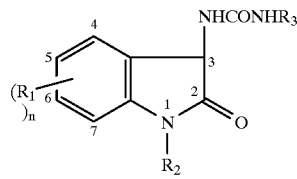
| Ex. No. | (R₂)n | R₂ | R₃ |
|---|---|---|---|
| 41 | — | —CH₂CH(OC₂H₅)₂ | 4-COOC₂H₅-C₆H₄— |
| 42 | — | " | 3,5-(CH₃)₂-C₆H₃— |
| 43 | 5-F | " | 4-CH₃-C₆H₄— |
| 44 | 5-OCH₃ | " | " |
| 45 | — | " | 2-CH₃-C₆H₄— |
| 46 | — | " | 3-Cl-C₆H₄— |
| 47 | — | " | 2-CH₃O-C₆H₄— |
| 48 | — | " | 4-NO₂-C₆H₄— |
| 49 | — | " | 4-CN-C₆H₄— |
| 50 | — | " | 3-CF₃-C₆H₄— |
TABLE B-2-continued
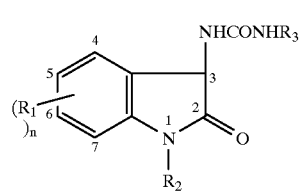
| Ex. No. | (R₂)n | R₂ | R₃ |
|---|---|---|---|
| 51 | — | " | 3-F-C₆H₄— |
| 52 | — | " | 4-CF₃-C₆H₄— |
| 195 | — | " | 4-CH₃-C₆H₄— |
TABLE C
| Test Compound (Example No.) | Gastric Receptor Binding Test (Test Example 1) IC$_{50}$ (nM) | Gastric Acid Secretion Inhibition (%) (Test Example 2) 10 mg/kg, i.d. |
|---|---|---|
| 10 | 2.5 | 59 |
| 14 | 2.2 | 49 |
| 71 | 1.1 | 48 |
| 79 | 1.9 | 47 |
| 81 | 1.6 | 59 |
| 82 | 6.2 | 56 |
| 84 | 3.4 | 68 |
| 85 | 1.2 | 72 |
| 89 | 5.8 | 65 |
| 92 | 4.3 | 57 |
| 94 | 3.5 | 70 |
| 111 | 5.1 | 69 |
| 114 | 2.4 | 56 |
| 122 | 2.9 | 62 |
| 124 | 5.3 | 54 |
| 125 | 2.5 | 54 |
| 129 | 3.6 | 71 |
| 130 | 4.9 | 71 |
| 131 | 23 | 65 |
| 132 | 8.9 | 52 |
| 138 | 2.2 | 69 |
| 143 | 1.5 | 64 |
| 148 | 1.1 | 63 |
| 149 | 0.93 | 69 |
| 151 | 2.9 | 62 |
| 152 | 2.1 | 64 |
| 154 | 1.0 | 59 |
| 156 | 6.5 | 69 |
| 158 | 1.4 | 66 |
| 168 | 2.6 | 61 |
| 169 | 1.9 | 52 |

TABLE C-continued

| Test Compound (Example No.) | Gastric Receptor Binding Test (Test Example 1) IC$_{50}$ (nM) | Gastric Acid Secretion Inhibition (%) (Test Example 2) 10 mg/kg, i.d. |
|---|---|---|
| 170 | 5.1 | 63 |
| 174 | 0.54 | 70 |
| 179 | 1.6 | 63 |
| 180 | 4.6 | 73 |
| 181 | 2.2 | 69 |
| 188 | 0.35 | 76 (3 mg/kg) |
| 190 | 0.68 | 70 |
| 191 | 5.5 | 78 |

TABLE D

| Compound No. (Example No.) | CCK-B Receptor Binding Test (Test Example 3) IC$_{50}$ (nM) | Compound No. (Example No.) | CCK-B Receptor Binding Test (Test Example 3) IC$_{50}$ (nM) |
|---|---|---|---|
| 62 | 1.2 | 129 | 0.39 |
| 65 | 0.76 | 130 | 2.3 |
| 66 | 0.76 | 180 | 0.36 |
| 71 | 1.2 | 92 | 0.90 |
| 174 | 0.42 | 143 | 1.9 |
| 7 | 0.07 | 181 | 0.78 |
| 111 | 0.35 | 156 | 2.8 |
| 114 | 0.64 | 191 | 0.45 |
| 138 | 0.50 | 158 | 0.56 |
| 179 | 0.14 | 190 | 0.10 |
| 122 | 0.18 | | |

Industrial Applicability

The compounds according to the present invention exhibit selective antagonism against gastrin receptors without causing side effects attributed to CCK-A receptor antagonism and are useful for the treatment and prevention of diseases of digestive organs, such as peptic ulcers, gastritis, reflux esophagitis, and Zollinger-Ellison syndrome. The compounds are also useful for the treatment of tumours originating in the gastrointestinal system and which also antagonizes selectively against CCK-B receptors and are useful for the treatment of CCK-related disorders in the appetite control system, enhancement and prolongation of analgesia through opiate or non-opiate, induction of anesthesia or analgesia, and the treatment and prevention of symptoms of psychotic disorders, including anxiety and panic disorders.

What is claimed is:
1. A compound represented by formula (II):

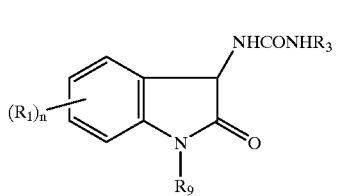

(II)

wherein
R$_1$ represents a halogen atom; a lower alkyl group; a lower alkoxy group; a hydroxyl group; a nitro group; a trifluoromethyl group; a lower alkylthio group; a carbonyl group which is substituted by a hydrogen atom, a lower alkyl group, a carbocylic aryl group having 6–14 carbon atoms, lower alkoxy group or an amino group; a carboxyl group; a mercapto group; or a substituted or unsubstituted amino group;

R$_3$ represents a substituted or unsubstituted pyridyl group;

n represents an integer of from 0 to 4; and

R$_9$ represents a group represented by formula (III):

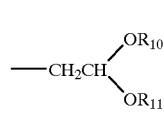

(III)

wherein R$_{10}$ and R$_{11}$ each represent a substituted or unsubstituted lower alkyl group having 1–6 carbon atoms, or a group represented by formula (IV):

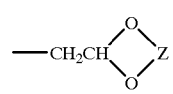

(IV)

wherein Z represents a substituted or unsubstituted lower alkylene group having 1–8 carbon atoms, or a salt thereof or an optically active isomer thereof wherein the substituents in the definition of R1, R3, R10, R11 and Z represent a halogen atom; a lower alkyl group having 1–6 carbon atoms; a C3–C8 cycloalkyl group; a C6–C14 aryl group; a hydroxyl group; a lower alkoxy group having 1–6 carbon atoms; a C6–C14 aryloxy group; a lower alkylthio group; 'CH(OR')$_2$, wherein R' represents a lower alkyl group having 1–6 carbon atoms; a lower alkylcarbonyl group; a C6–C14 arylcarbonyl group; a carboxyl group; a lower alkoxycarbonyl group; an amino group which may be substituted with one to two methyl groups, an ethyl group or a trifluoromethylcarbonyl group; an imino group; —CR"(SR')$_2$, wherein R' and R" represent a lower alkyl group having 1–6 carbon atoms; a nitro group; a nitrile group; or a trifluoromethyl group.

* * * * *

UNITED STATES PATENT AND TRADEMARK OFFICE
CERTIFICATE OF CORRECTION

PATENT NO. : 6,127,544

DATED : October 3, 2000

INVENTOR(S): ESAKI, Toru; EMURA, Takashi; and HOSHINO, Eiichi

It is certified that error appears in the above-identified patent and that said Letters Patent is hereby corrected as shown below:

Please change [62] "Division of application No. 08/963,547, Nov. 3, 1997, Pat. No. 5,932,511 which is a continuation of application No. 08/448,579, filed as application No. PCT/JP94/00235, Feb. 17, 1994, abandoned" to --Division of Application No. 08/963,547, filed Nov. 3, 997, (U.S. Pat. No. 5,952,511), which is a continuation application of Application No. 08/448,579, filed June 6, 1995 (abandoned), which is the §371 national application of PCT International application PCT/JP/00235, Feb. 17, 1994.--

Signed and Sealed this

Eighth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,127,544  
DATED : October 3, 2000  
INVENTOR(S) : Esaki, Toru; Emura, Takashi; and Hoshino, Eiichi Page 1 of 1

It is certified that error appears in the above-identified patent and that said Letters Patent is hereby corrected as shown below:

Please change item [62] "Division of application No. 08/963,547, Nov. 3, 1997, Pat. No. 5,932,511 which is a continuation of application No. 08/448,579, filed as application No. PCT/JP94/00235, Feb. 17, 1994, abandoned" to -- Division of Application No. 08/963,547, filed Nov. 3, 1997, (U.S. Pat. No. 5,952,511), which is a continuation application of Application No. 08/448,579, filed June 6, 1995 (abandoned), which is the §371 national application of PCT International application PCT/JP94/00235, Feb. 17, 1994. --

Signed and Sealed this

Twenty-third Day of October, 2001

Attest:

*Nicholas P. Godici*

NICHOLAS P. GODICI  
*Attesting Officer*  *Acting Director of the United States Patent and Trademark Office*